US009108948B2

(12) United States Patent
Liu et al.

(10) Patent No.: US 9,108,948 B2
(45) Date of Patent: *Aug. 18, 2015

(54) CYCLOPROPYL AMINE DERIVATIVES

(75) Inventors: Huaqing Liu, Buffalo Grove, IL (US);
Lawrence A. Black, Libertyville, IL (US); Youssef L. Bennani, Boston, MA (US); Marlon D. Cowart, Round Lake Beach, IL (US); Zhenping Tian, San Francisco, CA (US); Paul J. Brackemeyer, Arlington Heights, IL (US)

(73) Assignee: AbbVie Inc., North Chicago, IL (US)

( * ) Notice: Subject to any disclaimer, the term of this patent is extended or adjusted under 35 U.S.C. 154(b) by 972 days.

This patent is subject to a terminal disclaimer.

(21) Appl. No.: 11/956,816

(22) Filed: Dec. 14, 2007

(65) Prior Publication Data
US 2008/0242653 A1  Oct. 2, 2008

Related U.S. Application Data

(63) Continuation-in-part of application No. 11/766,987, filed on Jun. 22, 2007.

(60) Provisional application No. 60/815,934, filed on Jun. 23, 2006.

(51) Int. Cl.
| A61K 31/50 | (2006.01) |
|---|---|
| A61K 31/501 | (2006.01) |
| C07D 401/02 | (2006.01) |
| C07D 237/04 | (2006.01) |
| C07D 401/12 | (2006.01) |
| C07D 207/06 | (2006.01) |
| C07D 207/08 | (2006.01) |
| C07D 207/12 | (2006.01) |
| C07D 213/82 | (2006.01) |
| C07D 295/14 | (2006.01) |
| C07D 295/155 | (2006.01) |
| C07D 401/10 | (2006.01) |
| C07D 403/10 | (2006.01) |
| C07D 403/12 | (2006.01) |
| C07D 417/10 | (2006.01) |
| C07D 417/12 | (2006.01) |
| C07D 495/04 | (2006.01) |

(52) U.S. Cl.
CPC .......... *C07D 401/12* (2013.01); *C07D 207/06* (2013.01); *C07D 207/08* (2013.01); *C07D 207/12* (2013.01); *C07D 213/82* (2013.01); *C07D 295/14* (2013.01); *C07D 295/155* (2013.01); *C07D 401/10* (2013.01); *C07D 403/10* (2013.01); *C07D 403/12* (2013.01); *C07D 417/10* (2013.01); *C07D 417/12* (2013.01); *C07D 495/04* (2013.01)

(58) Field of Classification Search
None
See application file for complete search history.

(56) References Cited

U.S. PATENT DOCUMENTS

| 4,507,318 | A | 3/1985 | Coussee et al. |
|---|---|---|---|
| 5,086,054 | A | 2/1992 | Parish |
| 6,048,876 | A | 4/2000 | Annoura et al. |
| 6,166,023 | A | 12/2000 | Schindler et al. |
| 6,235,791 | B1 | 5/2001 | Breliere et al. |
| 6,515,013 | B2 | 2/2003 | Bennani et al. |
| 6,620,839 | B2 | 9/2003 | Bennani et al. |
| 6,838,466 | B2 | 1/2005 | Zhu et al. |
| 6,969,730 | B2 | 11/2005 | Cowart et al. |
| 7,094,790 | B2 | 8/2006 | Cowart et al. |
| 7,098,222 | B2 | 8/2006 | Altenbach et al. |
| 7,153,889 | B2 | 12/2006 | Altenbach et al. |
| 7,205,316 | B2 | 4/2007 | Altenbach et al. |
| 7,345,034 | B2 | 3/2008 | Zhao et al. |

(Continued)

FOREIGN PATENT DOCUMENTS

| CA | 2734800 A1 | 2/2010 |
|---|---|---|
| DE | 10153345 A1 | 5/2003 |

(Continued)

OTHER PUBLICATIONS

Airaksinen, M.S, et al., "Histamine Neurons in Human Hypothalamus: Anatomy in Normal and Alzheimer Diseased Brains", Neuroscience, 44: 465-481 (1998).

Arrang, J-M., "Auto-inhibition of brain histamine release mediated by a novel class ($H_3$) of histamine receptor", Nature, 302: 832-837 (1983).

Arrang, J-M., "Highly potent and selective ligands for histamine $H_3$-receptors", Nature, 327: 117-123 (1987).

(Continued)

*Primary Examiner* — Noble Jarrell
(74) *Attorney, Agent, or Firm* — Lisa V. Mueller; Michael Best & Friedrich LLP

(57) ABSTRACT

Compounds of formula (I)

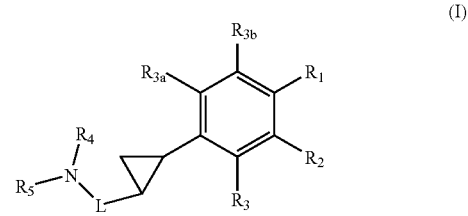

wherein $R_1$, $R_2$, $R_3$, $R_{3a}$, $R_{3b}$, $R_4$, and $R_5$ are defined in the description, are useful in treating conditions or disorders prevented by or ameliorated by histamine-3 receptor ligands. Also disclosed are pharmaceutical compositions comprising the histamine-3 receptor ligands, methods for using such compounds and compositions, and a process for preparing compounds within the scope of formula (I).

9 Claims, 6 Drawing Sheets

(56) References Cited

U.S. PATENT DOCUMENTS

| | | | |
|---|---|---|---|
| 7,358,263 B2 | 4/2008 | Cowart et al. | |
| 7,381,537 B2 | 6/2008 | Demuth et al. | |
| 7,462,599 B2 | 12/2008 | Schilling et al. | |
| 7,576,110 B2 | 8/2009 | Cowart et al. | |
| 7,696,193 B2 | 4/2010 | Sehmi et al. | |
| 7,732,162 B2 | 6/2010 | Hoffman et al. | |
| 7,799,773 B2 | 9/2010 | Bamford et al. | |
| 2002/0052383 A1 | 5/2002 | Bakthavatchalam et al. | |
| 2002/0169188 A1 | 11/2002 | Cowart et al. | |
| 2003/0119796 A1 | 6/2003 | Strony | |
| 2004/0224954 A1 | 11/2004 | Sattlegger et al. | |
| 2004/0224980 A1 | 11/2004 | Sattlegger et al. | |
| 2005/0171181 A1 | 8/2005 | Wager et al. | |
| 2005/0182045 A1 | 8/2005 | Nagase et al. | |
| 2005/0245529 A1 | 11/2005 | Stenkamp et al. | |
| 2006/0007413 A1 | 1/2006 | Nanba | |
| 2006/0040918 A1 | 2/2006 | Bamford et al. | |
| 2006/0074103 A1 | 4/2006 | Corte et al. | |
| 2007/0066588 A1 | 3/2007 | Cowart et al. | |
| 2007/0066644 A1 | 3/2007 | De Lera Ruiz et al. | |
| 2007/0066821 A1 | 3/2007 | Allison et al. | |
| 2007/0078133 A1 | 4/2007 | Liu et al. | |
| 2007/0208005 A1 | 9/2007 | Parr et al. | |
| 2007/0299056 A1 | 12/2007 | Bamford et al. | |
| 2008/0021081 A1* | 1/2008 | Liu et al. | 514/385 |
| 2008/0027041 A1 | 1/2008 | Hudkins et al. | |
| 2008/0139589 A1 | 6/2008 | Kanatani et al. | |
| 2008/0176925 A1 | 7/2008 | Butler et al. | |
| 2008/0242653 A1 | 10/2008 | Liu et al. | |
| 2008/0286810 A1 | 11/2008 | Demuth et al. | |
| 2009/0036425 A1 | 2/2009 | Dow et al. | |
| 2009/0068699 A1 | 3/2009 | Schilling et al. | |
| 2009/0075938 A1 | 3/2009 | Wynne et al. | |
| 2009/0076020 A1 | 3/2009 | Arnold et al. | |
| 2009/0137587 A1 | 5/2009 | Naya et al. | |
| 2009/0192168 A1 | 7/2009 | Muci et al. | |
| 2010/0016344 A1 | 1/2010 | Wakefield et al. | |
| 2010/0040575 A1 | 2/2010 | Hoffmann et al. | |
| 2010/0204205 A1 | 8/2010 | Barak et al. | |
| 2010/0216812 A1 | 8/2010 | Griffin | |
| 2010/0227876 A1 | 9/2010 | Rech | |
| 2010/0249144 A1 | 9/2010 | Demong et al. | |
| 2010/0267714 A1 | 10/2010 | Jorgensen et al. | |
| 2010/0273778 A1 | 10/2010 | Cowart et al. | |
| 2010/0286160 A1 | 11/2010 | Gilbert et al. | |
| 2010/0292188 A1 | 11/2010 | Denonne et al. | |
| 2011/0009430 A1 | 1/2011 | Moran et al. | |
| 2011/0098300 A1 | 4/2011 | Celanire et al. | |
| 2011/0195932 A1 | 8/2011 | Wynne et al. | |
| 2012/0071651 A1 | 3/2012 | Ku et al. | |

FOREIGN PATENT DOCUMENTS

| | | |
|---|---|---|
| DE | 10153347 A1 | 5/2003 |
| EP | 0251466 | 1/1988 |
| EP | 259977 A2 | 3/1988 |
| EP | 0188887 | 5/1991 |
| EP | 0668270 A2 | 8/1995 |
| EP | 0982300 | 3/2000 |
| EP | 1321169 A1 | 6/2003 |
| EP | 1675578 A2 | 7/2006 |
| EP | 1961416 A1 | 8/2008 |
| EP | 2117540 A1 | 11/2009 |
| EP | 2195293 A2 | 6/2010 |
| EP | 2206496 A1 | 7/2010 |
| EP | 2238144 A1 | 10/2010 |
| EP | 2253615 A1 | 11/2010 |
| EP | 2289498 A1 | 3/2011 |
| EP | 2300426 A1 | 3/2011 |
| ES | 1595881 A1 | 11/2005 |
| FR | 2856596 | 6/2003 |
| GB | 1086191 | 10/1967 |
| GB | 2210364 | 6/1989 |
| JP | 2000047358 A | 2/2000 |
| JP | 2002236340 A | 8/2002 |
| JP | 2004131497 | 4/2004 |
| JP | 2005170934 A | 6/2005 |
| JP | 2005281223 A | 10/2005 |
| NL | 6412766 | 5/1965 |
| WO | 9415928 A1 | 7/1994 |
| WO | 9520588 A1 | 8/1995 |
| WO | 0044728 | 3/2000 |
| WO | WO0042023 A1 | 7/2000 |
| WO | WO0063208 A1 | 10/2000 |
| WO | WO0064884 A1 | 11/2000 |
| WO | 0063208 B1 | 12/2000 |
| WO | 0213821 | 2/2002 |
| WO | WO0244128 A2 | 6/2002 |
| WO | 02074758 A2 | 9/2002 |
| WO | WO03066604 A2 | 8/2003 |
| WO | WO03099276 A1 | 12/2003 |
| WO | WO03104235 A1 | 12/2003 |
| WO | WO2004026305 A1 | 4/2004 |
| WO | WO2004035556 A1 | 4/2004 |
| WO | 2004043458 A1 | 5/2004 |
| WO | WO2004037801 A1 | 5/2004 |
| WO | WO2004037813 A1 | 5/2004 |
| WO | WO2004041776 A2 | 5/2004 |
| WO | 2005000315 | 6/2004 |
| WO | WO2004046110 | 6/2004 |
| WO | WO2004056369 A1 | 7/2004 |
| WO | WO2004098625 A2 | 11/2004 |
| WO | WO2004099199 A1 | 11/2004 |
| WO | WO2004101546 A1 | 11/2004 |
| WO | WO2005009471 A1 | 2/2005 |
| WO | WO2005009976 A1 | 2/2005 |
| WO | WO2005018045 A1 | 2/2005 |
| WO | WO2005032468 A2 | 4/2005 |
| WO | WO2005058837 A1 | 6/2005 |
| WO | WO2005072740 A2 | 8/2005 |
| WO | WO2005080361 A1 | 9/2005 |
| WO | WO2005087746 A1 | 9/2005 |
| WO | 2005103032 | 11/2005 |
| WO | 2005108384 | 11/2005 |
| WO | WO2005123723 A1 | 12/2005 |
| WO | 2006004937 | 1/2006 |
| WO | WO2006018260 A1 | 2/2006 |
| WO | WO2006029906 A1 | 3/2006 |
| WO | WO2006040192 A1 | 4/2006 |
| WO | 2006103537 | 5/2006 |
| WO | WO2006061193 A1 | 6/2006 |
| WO | WO2006072596 A1 | 7/2006 |
| WO | WO2006085692 A1 | 8/2006 |
| WO | WO2006090142 A1 | 8/2006 |
| WO | WO2006097691 A1 | 9/2006 |
| WO | 2006103546 | 10/2006 |
| WO | WO2006090142 C2 | 11/2006 |
| WO | WO2006123020 A1 | 11/2006 |
| WO | WO2006124687 A1 | 11/2006 |
| WO | 2006132914 | 12/2006 |
| WO | WO2006132424 | 12/2006 |
| WO | WO2007003604 A2 | 1/2007 |
| WO | WO2007004735 A1 | 1/2007 |
| WO | 2006132914 A3 | 3/2007 |
| WO | WO2007024004 A1 | 3/2007 |
| WO | WO2007025144 A1 | 3/2007 |
| WO | WO2007025596 A1 | 3/2007 |
| WO | WO2007038074 A1 | 4/2007 |
| WO | WO2007048595 A1 | 5/2007 |
| WO | WO2007052124 A1 | 5/2007 |
| WO | WO2007126957 A2 | 11/2007 |
| WO | 2007150010 | 12/2007 |
| WO | WO2007137968 A1 | 12/2007 |
| WO | WO2008064310 A2 | 5/2008 |
| WO | WO2008064317 A1 | 5/2008 |
| WO | WO2008064318 A1 | 5/2008 |
| WO | WO2008067257 A2 | 6/2008 |
| WO | WO2008104590 A2 | 9/2008 |
| WO | WO2008151156 A1 | 12/2008 |
| WO | WO2009024823 A2 | 2/2009 |
| WO | WO2009030716 A1 | 3/2009 |
| WO | WO2009039431 A2 | 3/2009 |
| WO | WO2008104590 A3 | 7/2009 |

(56) References Cited

FOREIGN PATENT DOCUMENTS

| WO | WO2009081195 A1 | 7/2009 |
|----|----|----|
| WO | WO2009085945 A1 | 7/2009 |
| WO | WO2009092764 A1 | 7/2009 |
| WO | WO2009100120 A2 | 8/2009 |
| WO | WO2009100294 A2 | 8/2009 |
| WO | WO2009115874 A2 | 9/2009 |
| WO | WO2009100120 A3 | 10/2009 |
| WO | WO2009124553 A2 | 10/2009 |
| WO | WO2009100294 A3 | 11/2009 |
| WO | WO2009147149 A1 | 12/2009 |
| WO | WO2009151991 A1 | 12/2009 |
| WO | WO2010007382 A1 | 1/2010 |
| WO | WO2010007382 A8 | 3/2010 |
| WO | WO2010071822 A1 | 6/2010 |
| WO | WO2009039431 A3 | 7/2010 |
| WO | WO2010080757 A2 | 7/2010 |
| WO | WO2010129242 A2 | 11/2010 |
| WO | WO2010129242 A3 | 12/2010 |
| WO | WO2011083314 A1 | 7/2011 |
| WO | WO2011083315 A1 | 7/2011 |
| WO | WO2011083316 A1 | 7/2011 |

OTHER PUBLICATIONS

Arrang, J.-M., "Histamine $H_3$ receptor binding sites in rat brain membranes: modulations by guanine nucleotides and divalent cations", European Journal of Pharmacology—Molecular Pharmacology Section, 188: 219-227 (1990).

Barbier, A.J. and Bradbury, M.J., "Histaminergic Control of Sleep-Wake Cycles: Recent Therapeutic Advances for Sleep and Wake Disorders", CNS and Neurological Disorders-Drug Targets, 5: 31-43 (2007).

Barbier, A.J., et al., "Acute wake-promoting actions of JNJ-5207852, a novel, diamine-based $H_3$ antagonist", British Journal of Pharmacology, 143: 649-661 (2004).

Bernaerts, P., et al., "Histamine $H_3$ antagonist thioperamide dose-dependently enhances memory consolidation and reverses amnesia induced by dizocilpine or scopolamine in a one-trial inhibitory avoidance task in mice", Behavioural Brain Research, 154: 211-219 (2004).

Bjenning, C., et al., "Peripherally administered ciproxifan elevates hypothalamic histamine levels and potently reduces food intake in the Sprague Dawley rat", Abstracts, Intl. Sendai Histamine Symposium, Sendai, Japan, #P39, (Nov. 2000).

Browman, Kaitlin E., et al., "Enhancement of prepulse inhibition of startle in mice by the $H_3$ receptor antagonists thioperamide and ciproxifan", Behavioural Brain Research, 153(1): 69-76 (2004).

Burger, A., et al., "2-(4-Imidazolyl) cyclopropylamine", J. Med. Chem. 13: 33-35 (1970).

Celanaire, et al., Drug Discovery Today "Histamine $H_3$ receptor antagonists reach out for the clinic" 10:1613-1627 (2005).

Charette, A.B., "(2S,3S)-(+)-(3-Phenylcyclopropyl)Methanol", Org. Syntheses, Coll., 76: 86-96 (1999).

Chen, et al., "Effects of histamine on MK-801-induced memory deficits in radial maze performance in rats", Brain Research, 839:186-189 (1999).

Chen, Z., et al., "Pharmacological effects of carcinine on histaminergic neurons in the brain", British J. of Pharmacology, 143: 573-580 (2004).

Clapham, J., Kilpatrick, G.J., "Thioperamide, the selective histamine $H_3$ receptor antagonist, attenuates stimulant-induced locomotor activity in the mouse", European Journal of Pharmacology, 259(2): 107-114 (1994).

Cowart, et al., "4-(2-[2-(2(R)- Methylpyrrolidin-1-y1) ethyl]benzofuran-5yl) benzonitrile and Related 2-Aminoethylbenzofuran $H_3$ Receptor Antagonists Potently Enhance Cognition and Attention", J. Med. Chem., 48:38-55 (2005).

DeAlmeida and Izaquierdo, "Memory Facilitation by Histamine", Arch. In. Pharmacodyn, vol. 283: 193-198 (1986).

Delaunois, A., et al., "Modulation of acetylocholine, capsaicin and substance P effects by histamine $H_3$ receptors in isolated perfused rabbit lungs", European J. of Pharmacology, 277: 243-250 (1995).

Dimitriadou, et al., "Functional relationship between mast cells and C-sensitive nerve fibres evidenced by histamine $H_3$-receptor modulation in rat lung and spleen", Clinical Science, 87: 151-163 (1994).

Dumery and Blozovski, "Development of amygdaloid cholinergic mediation of passive avoidance learning in the rat", Exp. Brain Res., 67; 61-69 (1987).

Dvorak, C., et al., "4-Phenoxypiperidines: Potent, Conformationally Restricted, non-Imidazole Histamine $H_3$ Antagonists", Journal of Medicinal Chemistry, 48: 2229-2238 (2005).

Esbenshade, et al., "Pharmacological Properties of ABT-239 [4-(2-{2-[(2R)-2-Methylpyrrolidinyl]ethyl}-benzofuran-5-yl)benzonitrile]: 1. Potent and Selective Histamine $H_3$ Receptor Antagonist with Drug-Like Properties", Journal of Pharmacology and Experimental Therapeutics, 313: 165-175 (2005).

Esbenshade, T., et al., "Pharmacological and behavioral properties of A-349821, a selective and potent human histamine $H_3$ receptor antagonist", Biochemical Pharmacology, 68: 933-945 (2004).

Fitzsimons, C.H., et al., "Histamine receptors signaling in epidermal tumor cell lines with H-ras gene alternations", Inflammation Res. 47:(Supp 1): S50-S51 (1998).

Fox, G.B., et al."Effects of histamine $H_3$ receptor ligands GT-2331 and ciproxifan in a repeated acquisition avoidance response in the spontaneously hypertensive rat pup", Behavioral Brain Research, 131: 151-161 (2002).

Fox, G.B., et al., "Two Novel and Selective Nonimidazole $H_3$ Receptor Antagonists A-304121 and A-317920: II. In Vivo Behavioral and Neurophysiological Characterization", Journal of Pharmacology and Experimental Therapeutics, 305(3): 897-908 (2003).

Fox, G.B., "Identification of novel $H_3$ receptor ($H_3R$) antagonists with cognition enhancing properties in rats", Inflammation Research, 52(1): S31-S32 (2003).

Fox, G.B., et al. "Pharmacological Properties of ABT—239 [4-(2-{2-[(2R)-2-Methy;pyrrolidinyl]ethyl]-benzofuran-5-y1) benzonitrile]: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics, 313: 176-190 (2005).

Furniss, Hannaford, Smith, and Tatchell, "Vogel's Textbook of Practical Organic Chemistry", $5^{th}$ Ed. (1989), Longman Scientific & Technical, Essex CM20 2JE, England (Table of Contents).

Glase, S.A., et al., "Attention deficit hyperactivity disorder: Pathophysiology and Design of New Treatments", Annual Reports in Medicinal Chemistry, 37: 11-20 (2002).

Haas, et al., "Subcortical modulation of synaptic plasticity in the hippocampus", Behavioural Brain Research, 66 : 41-44 (1995).

Halpern, M.T., "GT-2331", Current Opinion in Central and Peripheral Nervous System Investigational Drugs, 1: 524-527 (1999).

Hancock, A.A. "Antiobesity effects of A-331440, a novel non-imidazole histamine $H_3$ receptor antagonist", European Journal of Pharmacology, 487:183-197 (2004).

Hancock, A.A., et al., "Histamine $H_3$ antagonists in models of obesity", Inflamm. Res. 53 (1): S47-S48 (2004).

Harada, C., et al. "Inhibitory effect of iodophenpropit, a selective histamine $H_3$ antagonist, on amygdaloid kindled seizures", Brain Research Bulletin, 63: 143-146 (2004).

Harada, C., et al., "Intracerebroventricular Administration of Histamine $H_3$ Receptor Antagonists Decreases Seizures in Ray Models of Epilepsia", *Meth. Find Exp. Clin. Pharmacol.*, 26(4):263-270 (2004).

Hriscu, Anisoara et al., "Experimental evaluation of the analgesic efficacy of some antihistamines as proof of the histaminergic receptor involvement in pain", Farmacia, 49(2): 23-30 (2001).

Huang, Y.-W., et al, "Effect of the histamine $H_3$—antagonist clobenpropit on spatial memory deficits induced by MK-801 as evaluated by radial maze in Sprague-Dawley rats", Behavioural Brain Research, 151:287-293 (2004).

Itoh, E., et al., "Thioperamide, A histamine $H_3$ receptor antagonist, powerfully suppresses peptide YY-induced food intake in rats", Biol. Psych. 45(4):475-481 (1999).

(56) References Cited

OTHER PUBLICATIONS

IUPAC 1974 Recommendations for Section E, Fundamental Strereochemistry in Pure Appl. Chem., 45:13-30 (1976).
Jantzen and Robison, Modern Pharmacueticals p. 596 (1996).
Komater, V.A., et al, "$H_3$ receptor blockade by thioperamide enhances cognition in rats without inducing locomotor sensitization", Psychopharmacology (Berlin, Germany) 167(4): 363-372 (2003).
Krueger, et al., "G Protein-Dependent Pharmacology of Histamine $H_3$ Receptor Ligands: Evidence for heterogeneous Active State Receptor Conformations", Journal of Pharmacology and Experimental Therapeutics, 314: 271-281 (2005).
Leurs, R., Vollinga, R.C., et al., "The medicinal chemistry and therapeutic potential of ligands of the histamine $H_3$ receptor", Progress in Drug Research, 45: 107-165 (1995).
Leurs and Timmerman, "The histamine $H_3$-receptor: A target for developing new drugs", Prog. Drug. Res., 39:127-165 (1992).
Leurs and Timmerman, ed. "The History of $H_3$ Receptor: a Target for New Drugs", vol. 30, Elsevier, (1998).
Leurs, R., "Histamine Homologues Discriminating between Two Functional $H_3$ Receptor Assays. Evidence for $H_3$ Receptor Heterogeneity?", The Journal of Pharmacology and Experimental Therapeutics, 276:1009-1015 (1996).
Ligneau, et al., "Neurochemical and Behavioral Effects of Ciproxifan, A Potent Histamine $H_3$-Receptor Antagonist", Journal of Pharmacology and Experimental Therapeutics, 287:658-666 (1998).
Lin et al., "Involvement of histaminergic neurons in arousal mechanisms demonstrated with $H_3$-receptor ligands in the cat ", Brain Res., 523:325-330 (1990).
Lozada, et al., "Plasticity of histamine $H_3$ receptor expression and binding in the vestibular nuclei after labyrinthectomy in rat", BioMedCentral Neuroscience, 5:32 (2004).
Malmberg-Aiello, Petra; et al, "Role of histamine in rodent antinociception", British Journal of Pharmacology 111(4): 1269-1279 (1994).
Mazurkiewicz-Kwilecki and Nsonwah, "Changes in the regional brain histamine and histidine levels in postmortem brains of Alzheimer patients", Can. J. Physiol. Pharmacol., 67: 75-78 (1989).
McLeod, R.L., et al., "Combined histamine $H_1$ and $H_3$ receptor blockade produces nasal decongestion in an experimental model of nasal congestion", Am. J. Rhinol. 13: 391-399 (1999).
McLeod, Robbie L., et al., Progress in Respiratory Research, (in New Drugs for Asthma, Allergy and COPD), 31:133-136 (2001).
Medhurst, et al. "Structually novel histamine $H_3$ receptor antagonists GSK207040 and GSK334429 improve scopolamine-induced memory impairment and capsaicin-induced secondary allodynia in rats," Biochemical Pharmacology 73:1182-1194 (2007).
Medhurst, et al. "GSK189254, a Novel $H_3$ Receptor Antagonist That Binds to Histamine $H_3$ Receptors in Alzheimer's Disease Brain and Improves Cognitive Performance in Preclinical Models", Journal of Pharmacology & Experimental Therapeutics 321:1032-1045 2007.
Meguro, et al., "Effects of Thioperamide, a Histamine $H_3$ Antagonist, on the Step-Through Passive Avoidance Response amd Histidone Decarboxylase Activity in Senescence-Accelerated Mice" Pharmacology, Biochemistry and Behavior, 50(3): 321-325 (1995).
Monti, et al., "Sleep and Waking during Acute Histamine $H_3$ Agonist BP 2.94 or $H_3$ Antagonist Carboperamide (MR 16155) Administration in Rats", Neuropsycholopharmacology 15:31-35 (1996).
Morriset, S., et al., "Atypical Neuroleptics Enhance Histamine Turnover in Brain via 5-Hydroxytryptamine $_{2A}$ Receptor Blockade", Journal of Pharmacology and Experimental Therapeutics, 288:590-596 (1999).
Murakami, K., AQ-0145, a Newly Developed Histamine $H_3$ Antagonist, Decreased Seizure Susceptibility of electrically Induced Convulsions in Mice, Meth. Find. Exp. Clin. Pharmacol., 17(C):70-73 (1995).
O'Neill, et al., "Pharmacological Evaluation of an In Vivo Model of Vestibular Dysfunction in the Rat", Methods and Findings in Clinical Pharmacology, 21(4):285-289 (1999).
Onodera, K., et al., "Improvement by FUB 181, a novel histamine $H_3$-recptor antagonist, of learning and memory in the elevated plus-maze test in mice", Nauyn-Schmiedebergs' Arch. Pharmacol., 357:508-513 (1998).
Onodera, Kenji, et al., "Neuropharmacology of the Histaminergic Neuron System in the Brain and its Relationship with Behavioral Disorders", Progress in Neurobiology, 42:685-702 (1994).
Pan, et al., "Histaminergic Ligands Attenuate Barrel Rotation in Rats Following Unilateral Labyrinthectomy", Methods and Findings in Clinical Pharmacology, 20(9): 771-777 (1998).
Panula, P., et al., "Neuronal Histamine Deficit in Alzheimer's disease", Neuroscience, 82:993-997 (1998).
Passani, et al., "Central histaminergic system and cognition", Neuroscience and Biobehavioral Reviews, 24: 107-113 (2000).
Penning, T.D., et al.,"Structure-Activity Relationship Studies on 1-[2-(4-Phenylphenoxy) ethyl]pyrrolidine (SC-22716), a Potent Inhibitor of Leukotriene $A_4$ ($LTA_4$) Hydrolase" J. Med. Chem. 43: 721-735 (2000).
Perez-Garcia, C., et al., "Effects of histamine $H_3$ receptor ligands in experimental models of anxiety and depression", Psychopharmacology (Berlin), 142(2) : 215-220 (1999).
Prast, Helmut, et al., "Histaminergic neurons facilitate social memory in rats", Brain Research, 734:316-318 (1996).
Poste, George, Lipid Vesicles as Carriers for Introducing Biologically Active Materials into Cells, Chapter 4, pp. 33, et al. Prescott, Ed., "Methods in Cell Biology", vol. XIV, Academic Press, New York, NY (1976).
Pu, Yu-Ming, et al., "A Facile and Scaleable Synthesis of ABT-239, a Benzofuranoid $H_3$ Antagonist", Organic Process Research & Development, 9 :45-50 (2005).
Rodrigues, A. A., et al., "Interaction of clozapine with the histamine $H_3$ receptor in rat brain", British Journal of Pharmacology, 114(8) : 1523-1524 (1995).
Sakai, et al., Effects of Thioperamide, a Histamine $H_3$ Receptor Antagonist, on Locomotor Activity and Brain Histamine Content, et al., Life Sciences, 48 : 2397-2404 (1991).
Sakata, T., et al. "Hypothalamic neuronal histamine modulates ad libitum feeding by rats", Brain Research, 537(1-2): 303-306 (1990).
Sanchez-Lemus, E., et al., "Histamine $H_3$ receptor activation inhibits dopamine $D_1$ receptor-induced cAMP accumulation in rat striatal slices", Neuroscience Letters, 364 :179-184 (2004).
Schwartz, et al., "Histamine—Chapter 35", Psychopharmacology, The $4^{th}$ Generation of Progress. Bloom and Kupfer (eds). Raven Press, New York, pp. 397-405, (1995).
Schweitzer, J.B., and Holcomb, H.H., "Drugs under investigation for attention deficit hyperactivity disorder", Current Opinion in Investigational Drugs, 2:1207-1211 (2002).
Shaywitz, B.A., et al.,"Dopaminergic but not noradrenergic mediation of hyperactivity and performance deficits in the developing rat pup", Psychopharmacology, 82: 73-77 (1984).
Szelag, Adam, "Role of histamine $H_3$ receptors in the proliferation of neoplastic cells in vitro", Med. Sci. Monitor 4(50) : 747-755 (1998).
Tedford, Clark E., et al., "Pharmacological Characterization of GT-2016, a Non-Thiourea-Containing Histamine $H_3$ Receptor Antagonist: In Vitro and In Vivo Studies", J. Pharmacol. and Exp. Ther., 275: 598-604 (1995).
Tozer, Matthew & Kalindjian, S. B.; Histamine $H_3$ receptor antagonists, Expert Opinion on Therapeutic Patents, 10(7): 1045-1055 (2000).
Vohora, D., et al., Thioperamide, a Selective Histamine $H_3$ Receptor Antagonist, Protects against PTZ-Induced Seizures in Mice, Life Sciences, 66: 297-301 (2000).
Wada, Hiroshi, et al., "Is the histaminergic neuron system a regulatory center for whole-brain activity?", Trends in Neuroscience, 14: 415-421 (1991).
Wang, Yuguang, et al., "Design and Synthesis of Ether Analogues as Potent and Selective $M_2$ Muscarinic Receptor Antagonists", Bioorg.& Med. Chem. Lett., 11: 891-894 (2001).
Yates, Stephen, et al., "Effects of a novel histamine $H_3$ receptor antagonist, GT-2394, on food intake and weight gain in Sprague-Dawley rats", Abstracts, Society for Neuroscience, 10 :219 (2000).

(56) References Cited

OTHER PUBLICATIONS

Yates, Stephen, et al., "Identification and Pharmacological Characterization of a Series of New 1H-4-Substituted-Imidazoyl Histamine $H_3$ Receptor Ligands", Journal of Pharmacology and Experimental Therap., 289: 1151-1159 (1999).
Yawata, et al.,"Role of histaminergic neurons in development of epileptic seizures in EL mice", Molecular Brain Research, 132 : 13-17 (2004).
Yokoyama, et al., "Effect of thioperamide, a histamine $H_3$ receptor antagonist, on electrically induced convulstions in mice", Eur. J. Pharmacol., 234: 129-133 (1993).
Yokoyama, et al., "Clobenpropit (VUF-9153), a new histamine $H_3$ receptor antagonist, inhibits electrically induced convulsions in mice", Eur. J. Pharmacol. 260 :23-28 (1994).
Yokoyama, H. and K. Linuma, "Histamine and Seizures", CNS Drugs, 5(5) :321-330, (1996).
International Search Report for PCT/US2008/085622 mailed on Jun. 8, 2009.
International Search Report for PCT/US2007/071849 mailed on Jan. 15, 2008.
Njar, V., "High-Yields Synthesis of Novel Imidazoles and Triazoles from Alcohols and Phenols," Synthesis, 2000, vol. 14, pp. 2019-2028.
Office Action mailed Jan. 7, 2011 for U.S. Appl. No. 11/766,987, filed Jun. 22, 2007.
Office Action mailed Sep. 8, 2008 for U.S. Appl. No. 11/766,987, filed Jun. 22, 2007.
Office Action mailed Jan. 9, 2009 for U.S. Appl. No. 11/766,987, filed Jun. 22, 2007.
Office Action mailed Oct. 19, 2009 for U.S. Appl. No. 11/766,987, filed Jun. 22, 2007.
International Search Report for application No. PCT/US2007/071849, Mailed on Jan. 29, 2008, 5 pages.
Roche E., "Bioreversible Carriers in Drug Design, American Pharmaceutical Association and Pergamon Press Table of Contents," 1987.
Tedford, et al., "Cognition and Locomotor Activity in the Developing Rat: Comparisons of Histamine H3 Receptor Antagonists and ADHD Therapeutics," Soc. Neurosci. Abstr., vol. 22, pp. 22, 1996.
International Preliminary Report on Patentability and Written Opinion for Application No. PCT/US2007/071849, mailed on Jan. 6, 2009, 7 pages.
International Preliminary Report on Patentability and Written Opinion for Application No. PCT/US2008/085622, mailed on Jun. 15, 2010, 7 pages.
International Search Report for Application No. PCT/DK2003/000071, mailed on Jul. 29, 2003, 10 pages.
International Search Report for Application No. PCT/EP2006/063753, mailed on Apr. 27, 2007, 11 pages.
Njar, "High-Yields Synthesis of Novel Imidazoles and Triazoles form Alcohols and Phenols," Synthesis, 2000, pp. 2019-2028.
Office Action mailed Oct. 7, 2010 for U.S. Appl. No. 11/956,816, filed Dec. 14, 2007.
Office Action mailed Mar. 22, 2010 for U.S. Appl. No. 11/956,816, filed Dec. 14, 2007.
Roche E.B., ed., Bioreversible Carries in Drug Design Theory and Application, Pergamon Press, 1987, Table of Contents.
Berlin, et al., "Recent Advances in the Development of Histamine $H_3$ Antagonists" Expert Opinion in the Therapeutic Patents, 2007, vol. 17 (6), pp. 675-687.
Collins, et al., "Emerging Therapies for Neuropathic Pain," Expert Opinion on Emerging Drugs, 2005, vol. 10 (1), pp. 95-108.
Cowart, et al., "Pharmacological Characterization of A-960656, a Histamine $H_3$, Receptor Antagonist with Efficacy in Animal Models of Osteoarthritis and Neuropathic Pain," European Journal of Pharmacology, 2012, vol. 684 (1-3), pp. 87-94.
Dray, et al., "Pharmacology of Chronic Pain," Trends in Pharmacological Sciences, 1994, vol. 15 (6), pp. 190-197.
Dray, et al., "Arthritis Pain. Future Targets to Control Osteoarthritis Pain," Arthritis Research and Therapy, 2007, vol. 9 (3), pp. 212.
Dworkin, R., "An Overview of Neuropathic Pain: Syndromes, Symptoms, Signs, and Several Mechanisms," Clinical journal of Pain, 2002, vol. 18 (6), pp, 343-349.
Esbenshade, et al., "The Histamine $H_3$ Receptor: An Attractive Target for the Treatment of Cognitive Disorders," British Journal of Pharmacology, 2008, vol. 154 (6), pp. 1166-1181.
Fernihough, et al. "Pain Related Behaviour in Two Models of Osteoarthritis in the Rat Knee," Pain, 2004, vol. 112 (1-2), pp. 83-93.
International Search Report for Application No. PCT/US2011/051603, mailed on Dec. 5, 2011, 5 pages.
Joshi, et al., "Animal Models of Pain for Drug Discovery," Expert Opinion on Drug Discovery, 2006, vol. 1 (4), pp. 341-352.
Kallemeyn, et al., ChemInform, 2011, vol. 42 (26), 1 page.
Kallemeyn, et al., "Asymmetric Synthesis of Di-and Trisubstituted Cyclopropanes Through an Intramolecular Ring Closure," Synlett, 2011, vol. 4, pp. 535-538.
Mulhern, et al., "Asymmetric Synthesis of Di-and Trisubstituted Cyclopropanes Through an Intramolecular Ring Closure," Poster and Abstract, Aug. 24, 2010.
Rubin, B., "Management of Osteoarthritic Knee Pain," Journal of the American Osteopathic Association, 2005, vol. 105 (9 Suppl. 4), pp. S23-S28.
Sander, et al., "Histamine $H_3$ Receptor Antagonists Go to Clinics," Biological & Pharmaceutical Bulletin, 2008, vol. 31 (12), pp. 2163-2181.
Smith, et al., "Neuropathic Pain and the Electrophysiology and Pharmacology of Nerve Injury," Drug Development Research, 2001, vol. 54 (3), pp. 140-153.
Vinik A, et al., "Diabetic Neuropathies," The Medical Clinics of North America, 2004, vol. 88 (4), pp. 947-999.
Witkin, et al., "Selective Histamine $H_3$ Receptor Antagonists for the Treatment of Cognitive Deficiencies and Other Disorders of the Central Nervous System," Pharmacology and Therapeutics, 2004, vol. 103 (1), pp. 1-20.
Zhang, et al,, "Trans-1-[(2-Phenylcyclopropyl)methyl]-4-arylpiperazines: Mixed Dopamine D(2)/D(4) Receptor Antagonists as Potential Antipsychotic Agents," Journal of Medicinal Chemistry, 2000, vol. 43 (21), pp. 3923-3932.
Office Action mailed Aug. 8, 2011 for U.S. Appl. No. 11/766,987.
Berlin, et al., "Histamine $H_3$ Receptor as a Drug Discovery Target," Journal of Medicinal Chemistry, 2011, vol. 54 (1), pp. 26-53.
Blandina, et al., "Histamine Neuronal System as a Therapeutic Target for the Treatment of Cognitive Disorders," Future Neurology, 2010, vol. 5 (4), pp. 543-555.
Esbenshade, et al., "Histamine $H_3$ Receptor Antagonists: Preclinical Promise for Treating Obesity and Cognitive Disorders" Molecular Interventions, 2006, vol. 6 (2), pp. 77-88.
Foley A.G., et al., "$H_3$ Receptor Antagonism Enhances NCAM PSA-Mediated Plasticity and Improves Memory Consolidation in Odor Discrimination and Delayed Match-to-Position Paradigms," Neuropsychopharmacology, 2009, vol. 34 (12), pp. 2585-2600.
Hsieh, et al., "The Histamine $H_3$ Receptor as a Potential Antinociceptive Target: Effects of Selective $H_3$ Antagonists in Several Preclinical Pain Models and the Involvement of Noradrenergic Systems," Global Pharmaceutical Research & Development, 2009, Abbott Laboratories, Abbott Park, IL 60064.
Leurs R., et al., "En Route to New Blockbuster Anti-Histamines: Surveying the Offspring of the Expanding Histamine Receptor Family," Trends in Pharmacological Sciences, 2011, vol. 32 (4), pp. 250-257.
Medhurst S.J., et al., "Novel Histamine $H_3$ Receptor Antagonists GSK189254 and GSK334429 are Efficacious in Surgically-Induced and Virally-Induced Rat Models of Neuropathic Pain," Pain, 2008, vol. 138 (1), pp. 61-69.
International Search Report for PCT/US2008/085862 mailed Jun. 8, 2009.
International Search Report for PCT/US2007/071849 mailed Jan. 29, 2008.
Bomann M.D., et al., "A Mild, Pyridine-Borane-Based Reductive Amination Protocol," Journal of Organic Chemistry, 1995, vol. 60, pp. 5995-5996.
Boureau F., et al., "The IPSO Study: Ibuprofen, Paracetamol Study in Osteoarthritis. A Randomised Comparative Clinical Study Compar-

(56) References Cited

OTHER PUBLICATIONS ing the Efficacy and Safety of Ibuprofen and Paracetamol Analgesic Treatment of Osteoarthritis of the Knee or Hip," Annals of the Rheumatic Diseases, 2004, vol. 63 (9), pp. 1028-1034.

Brady W.T., et al., "Halogenated Ketenes. V. Cycloadditions of Dichloroketene to Olefins," Journal of Organic Chemistry, 1967, vol. 32, pp. 3703-3705.

Damasio A.R., "Alzheimer's Disease and Related Dementias" in: Cecil Textbook of Medicine, 20th Edition, Bennett J. C., et al., eds., W.B. Saunders Company, 1996, pp. 1992-1996.

Dehmlow E.V., et al., "Stereoselektive Synthese von 3-substituierten Cyclobutanolen and Folgeprodukten," Chemische Berichte, 1993, vol. 126, pp. 2759-2763.

Falmagne J.B., et al., "Cyclobutanone and Cyclobutenone Derivative by Reaction of Tertiary Amides with Alkenes or Alkynes," Angewandte Chemie International Edition, 1981, vol. 20 (10), pp. 879-880.

FDA Mulls Drug to Slow Late-Stage Alzheimer's [online], [retrieved on Sep. 23, 2003]. Retrieved from the Internet:< URL: http://www.cnn.com/2003/HEALTH/conditions/09/24/alzheimers.drug.ap/indexhtml>.

Ghosez L., et al., "Intramolecular Cycloadditions of Keteniminium Salts. A Novel Apporach Toward Prostaglandins," Tetrahedron Letters, 1986, vol. 27 (43), pp. 5211-5214.

Higuchi T., et al., eds., Pro-drugs as Novels Delivery Systems, vol. 14, ACS Symposium Series, 1975, Table of Contents.

Houge C., et al., "Models for Asymmetric [2+2] Cycloadditions," Journal of American Chemical Society, 1982, vol. 104, pp. 2920-2921.

International Preliminary Report on Patentability and Written Opinion for Application No. PCT/US2010/032488, mailed on Nov. 1, 2011, 6 pages.

International Search Report for Application No. PCT/US2006/021257, mailed on Dec. 15, 2006, 3 pages.

Invitation to Pay Additional Fees for Application No. PCT/US2010/032488, mailed Jun. 30, 2010, 7 pages.

Kamei C., et al., "Influence of Certain $H_1$-Blockers on the Step-Through Active Avoidance Response in Rats," Psychopharmacology, 1990, vol. 102 (3), pp. 312-318.

Kamei C., et al., "Participation of Histamine in the Step-Through Active Avoidance Response and Its Inhibition by $H_1$-Blockers," Japan Journal of Pharmacology, 1991, vol. 57 (4), pp. 473-482.

Kauffmann T., et al., "Home Aldehydselektivitat Bei Carbonylolefinierungen MIT Titan- Und Chrom-Reagenzien," Tetrahedron Letters, 1981, vol. 22 (50), pp. 5031-5034.

Krepski L.R., et al., "An Improved Procedure for the Addition of Dichloroketene to Unreactive Olefins," Journal of Organic Chemistry, 1978, vol. 43 (14), pp. 2879-2882.

Lamberti C., et al., "Antidepressant-like Effects of Endogenous Histamine and of Two Histamine H 1 Receptor Agonists in the Mouse Forced Swim Test," British Journal of Pharmacology, 1998, vol. 123 (7), pp. 1331-1336.

Layzer R.B., "Degenerative Diseases of the Nervous System" in: Cecil Textbook of Medicine, 20th Edition, Bennett J.C., et al., eds., W.B. Saunders Company, 1996, pp. 2050-2057.

Li S.W., et al., "A Novel Methylenation Method of Aldehydes Mediated by Dibutyl Telluride," Chemische Berichte, 1990, vol. 123, pp. 1441-1442.

Marko I., et al., "Intramolecular [2+2] Cycloadditions of Ketenes and Keteniminium Salts to Olefins," Journal of the American Chemical Society, 1985, vol. 107, pp. 2192-2194.

Monti J.M., et al., "Effects of Selective Activation or Blockade of the Histamine $H_3$ Receptor on Sleep And Wakefulness," Journal of Pharmacology, 1991, vol. 205, pp. 283-287.

Pelter A., et al., "Reductive Aminations of Ketones and Aldehydes using Borane-Pyridine," Journal of the Chemical Society, 1984, vol. 4, pp. 717-720.

Prodrug [online], [retrieved on Mar. 26, 2007]. Retrieved from the Internet:< URL: http://en.wikipedia.org/wiki/Prodrug>.

Shah C., et al., "Novel Human Histamine H3 Receptor Antagonists," Bioorganic & Medicinal Chemistry Letters, 2002, vol. 12 (22), pp. 3309-3312.

Srivastava R.R., et al., "4-Dihydroxyborylphenyl Analogues of 1-Aminocyclobutanecarboxylic Acids: Potential Boron Neutron Capture Therapy Agents," Journal of Organic Chemistry, 1999, vol. 64, pp. 8495-8500.

\* cited by examiner

CYCLOPROPYL AMINE DERIVATIVES

This is a continuation-in-part of U.S. patent application Ser. No. 11/766,987, filed on Jun. 22, 2007, now U.S. Pat. No. 8,829,041, which claims priority to U.S. Provisional Patent Application No. 60/815,934, filed on Jun. 23, 2006, both of which are hereby incorporated by reference.

BACKGROUND OF THE INVENTION

1. Technical Field

The invention relates to cyclopropyl amine compounds, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302: 832-837 (1983)), where it regulates the release of neurotransmitters in both the central nervous system and peripheral organs, particularly the lungs, cardiovascular system and gastrointestinal tract. $H_3$ receptors are thought to be located presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, inverse agonist, agonist, or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

Figure 1:
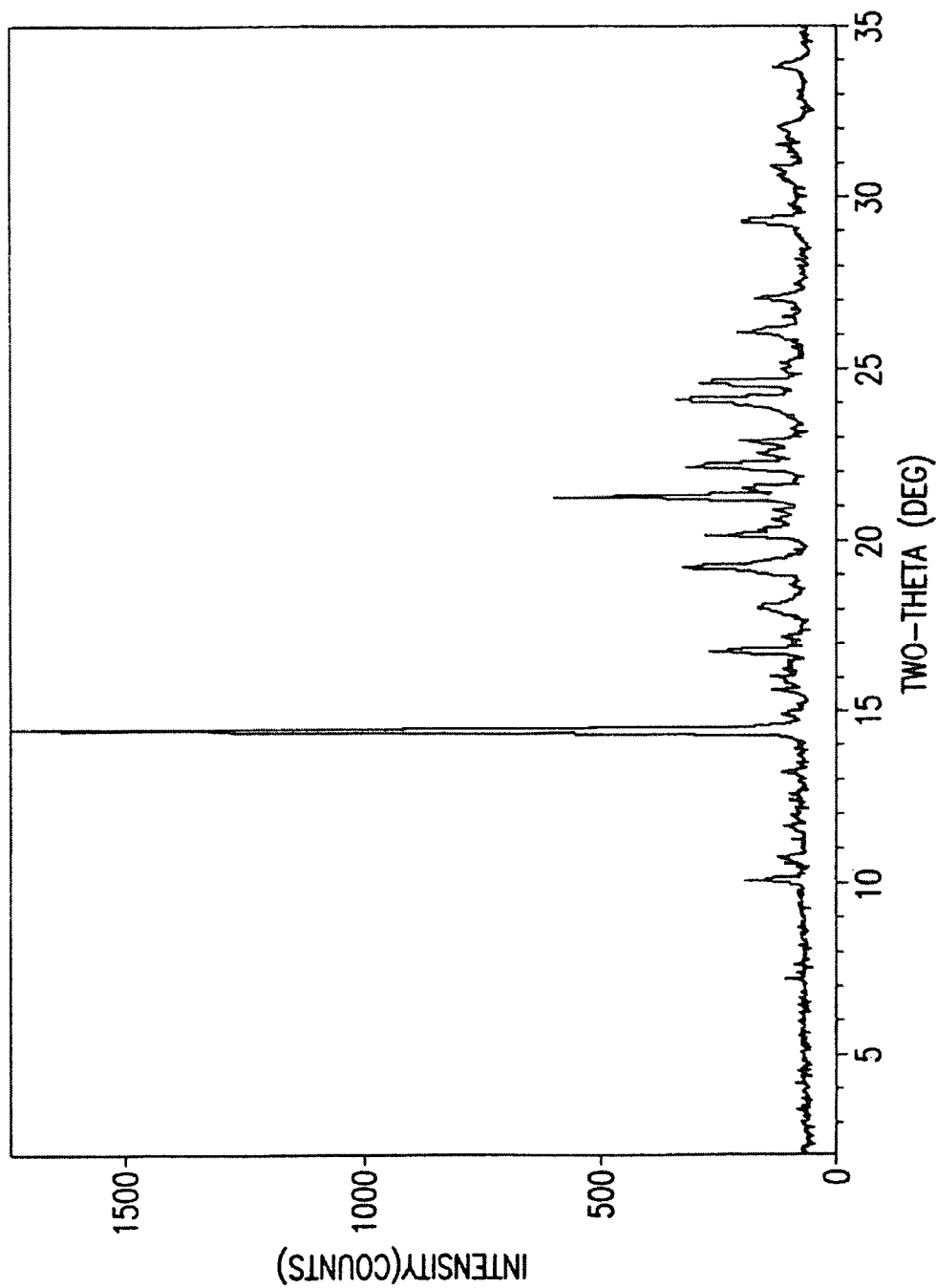
FIG. 1 is a powder X-ray diffraction pattern of 2-{4-[(1S,2S)-2-((S)-2-Methyl-pyrrolidin-1-ylmethyl)-cyclopropyl]-phenyl}-2H-pyridazin-3-one L-bitartrate monohydrate.

The invention is directed to cyclopropyl amines and, more particularly, bicyclic- and tricyclic-substituted cyclopropyl amine derivatives. Accordingly, one aspect of the invention relates to compounds of formula (I):

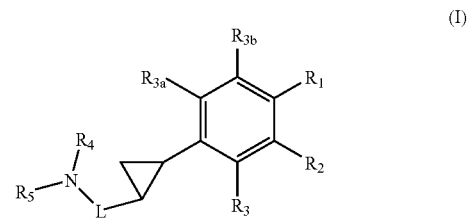

or a pharmaceutically acceptable salt, ester, amide, or prodrug thereof, wherein:

one of $R_1$ and $R_2$ is a group of the formula $-L_2-R_{6a}-L_3-R_{6b}$;

the other of $R_1$ and $R_2$ is selected from hydrogen, alkyl, alkoxy, halogen, cyano, and thioalkoxy;

$R_3$, $R_{3a}$, and $R_{3b}$ are each independently selected from the group consisting of hydrogen, alkyl, trifluoroalkyl, trifluoroalkoxy, alkoxy, halogen, cyano, and thioalkoxy $R_4$ and $R_5$ are each independently selected from alkyl, fluoroalkyl, hydroxyalkyl, alkoxyalkyl, and cycloalkyl, or $R_4$ and $R_5$ taken together with the nitrogen atom to which each is attached form a non-aromatic ring of the formula:

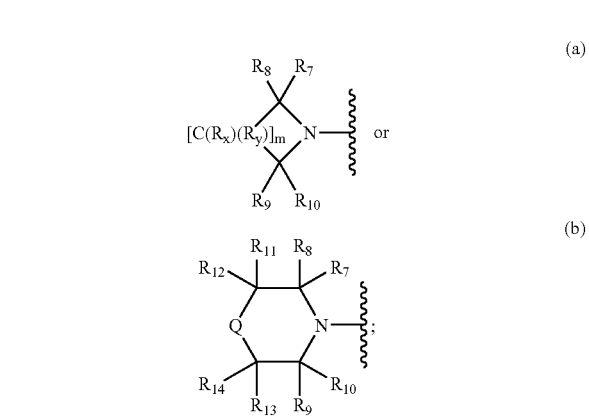

$R_7$, $R_8$, $R_9$, and $R_{10}$ at each occurrence are each independently selected from hydrogen, hydroxyalkyl, fluoroalkyl, cycloalkyl, and alkyl;

$R_{11}$, $R_{12}$, $R_{13}$, and $R_{14}$ are each independently selected from hydrogen, hydroxyalkyl, alkyl, and fluoroalkyl;

$R_{6a}$ is selected from a 5- to 6-membered heteroaryl ring, cyanophenyl, an 8- to 12-membered bicyclic heteroaryl ring, and a 4- to 12-membered heterocyclic ring;

$R_{6b}$ is selected from hydrogen, a 5- to 6-membered heteroaryl ring, an aryl ring, an 8- to 12-membered bicyclic heteroaryl ring, and a 4- to 12-membered heterocyclic ring;

Q is selected from O and S;

L is —[C($R_{16}$)($R_{17}$)]$_k$;

$L_2$ is selected from a bond, alkylene, —O—, —C(=O)—, —S—, —NH—, —N($R_{16}$)C(=O)—, —C(=O)N($R_{16}$), and —N(alkyl)-;

$L_3$ is selected from a bond, alkylene, —O—, —C(=O)—, —S—, —N($R_{16}$)C(=O)—, —C(=O)N($R_{16}$), and —N($R_{15}$)—;

$R_{15}$ is selected from hydrogen, alkyl, acyl, alkoxycarbonyl, amido, and formyl;

$R_{16}$ and $R_{17}$ at each occurrence are independently selected from hydrogen and alkyl;

$R_x$ and $R_y$ at each occurrence are independently selected from hydrogen, hydroxy, alkyl, alkoxy, alkylamino, fluoro, and dialkylamino;

k is 1, 2, or 3; and m is an integer from 1 to 5.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to particular salts of some compounds, processes for preparing such compounds and salts, and compositions comprising the same. Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to memory and cognition processes, neurological processes, cardiovascular function, and body weight. Accordingly, the compounds and compositions of the invention are useful as a medicament for treating or preventing $H_3$ receptor modulated diseases.

Processes for making compounds of the invention also are contemplated.

The compounds, compositions comprising the compounds, methods for making the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylene" means a divalent group derived from a straight or branched chain hydrocarbon of from 1 to 10 carbon atoms. Representative examples of alkylene include, but are not limited to, —$CH_2$—, —CH($CH_3$)—, —C($CH_3$)$_2$—, —$CH_2CH_2$—, —$CH_2CH_2CH_2$—, —$CH_2CH_2CH_2CH_2$—, and —$CH_2CH(CH_3)CH_2$—.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means a —NH$_2$ group.

The term "aryl" as used herein means a monocyclic hydrocarbon aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, NR$_A$R$_B$, and (NR$_A$R$_B$)sulfonyl.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group, which may be protected as an ester group —CO$_2$-alkyl.

The term "cyano" as used herein means a —CN group.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, oxo, thioalkoxy, and —NR$_A$R$_B$.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkoxy" as used herein means at least one fluoroalkyl group, as defined herein, appended to the parent molecular moiety through an oxygen group, as defined herein. Representative examples of fluoroalkyl include, but are not limited to, trifluoromethoxy (CF$_3$O), and difluoromethoxy (CHF$_2$O).

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety, or to L$_2$ or L$_3$, wherein L$_2$ and L$_3$ are defined in formula (I), through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, thieno[3,2-b]pyridinyl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$_A$R$_B$, and (NR$_A$R$_B$)carbonyl. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "heterocyclic ring" and "heterocycle", as used herein, refer to a 4- to 12-membered monocyclic or bicyclic ring containing one, two, three, four, or five heteroatoms independently selected from the group consisting of nitrogen, oxygen, and sulfur and also containing either at least one carbon atom attached to four other atoms or one carbon atom substituted with an oxo group and attached to two other atoms. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The heterocycles of the invention are substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —NR$_A$R$_B$, and (NR$_A$R$_B$)sulfonyl.

Additional examples of heterocycles include, but are not limited to, azetidin-2-one, azepan-2-one, isoindolin-1,3-dione, (Z)-1H-benzo[e][1,4]diazepin-5(4H)-one, pyridazin-3 (2H)-one, pyridin-2(1H)-one, pyrimidin-2(1H)-one, pyrimidin-2,4(1H,3H)-dione, pyrrolidin-2-one, benzo[d]thiazol-2 (3H)-one, pyridin-4(1H)-one, imidazolidin-2-one, 1H-imidazol-2(3H)-one, piperidin-2-one, tetrahydropyrimidin-2(1H)-one, 1H-benzo[d]imidazol-2(3H)-one, [1,2,4] thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, and 1,5-dihydrobenzo[b][1,4]diazepin-2-on-yl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl trifilate, trialkylsilyl halide, trialkylsilyl triflate, aryldialkylsilyltriflate, or an alkylchloroformate, CH$_2$I$_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "—NR$_A$R$_B$" as used herein means two groups, R$_A$ and R$_B$, which are appended to the parent molecular moiety through a nitrogen atom. R$_A$ and R$_B$ are independently selected from hydrogen, alkyl, acyl, and formyl. Representative examples of —NR$_A$R$_B$ include, but are not limited to, amino, dimethylamino, methylamino, acetylamino, and acetylmethylamino.

The term "(NR$_A$R$_B$)alkyl" as used herein means an —NR$_A$R$_B$ group, as defined herein, appended to the parent molecular moiety through an alkyl group, as defined herein. Representative examples of (NR$_A$R$_B$)alkyl include, but are not limited to, 2-(methylamino)ethyl, 2-(dimethylamino) ethyl, 2-(amino)ethyl, 2-(ethylmethylamino)ethyl, and the like.

The term "(NR$_A$R$_B$)carbonyl" as used herein means an —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, (ethylmethylamino) carbonyl, and the like.

The term "(NR$_A$R$_B$)sulfonyl" as used herein means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl and (ethylmethylamino)sulfonyl.

The term "nitro" as used herein means a —NO$_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl trifilate, a dialkyl anhydride, for example as represented by (alkyl-O)$_2$C=O, a diaryl anhydride, for example as represented by (aryl-O)$_2$C=O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

Compounds of the Invention

Compounds of the invention can have the formula (I) as described above.

In compounds of formula (I), one of $R_1$ and $R_2$ is a group of the formula -$L_2$-$R_{6a}$-$L_3$-$R_{6b}$. The other group of $R_1$ and $R_2$ is selected from hydrogen, alkyl, alkoxy, halogen, cyano, and thioalkoxy. Preferably, $R_1$ is -$L_2$-$R_{6a}$-$L_3$-$R_{6b}$ and $R_2$ is selected from hydrogen, alkyl, alkoxy, halogen, cyano, and thioalkoxy. When one of $R_1$ or $R_2$ is -$L_2$-$R_{6a}$-$L_3$-$R_{6b}$, then the other is preferably hydrogen.

$L_2$ is selected from a bond, alkylene, —O—, —C(=O)—, —S—, —NH—, —N($R_{16}$)C(=O)—, —C(=O)N($R_{16}$), and —N(alkyl)-. It is preferred that $L_2$ is a bond.

$L_3$ is selected from a bond, alkylene, —O—, —C(=O)—, —S—, —N($R_{16}$)C(=O)—, —C(=O)N($R_{16}$), and —N($R_{15}$)—, wherein $R_{15}$ is selected from hydrogen, alkyl, acyl, alkoxycarbonyl, amido, and formyl. It is preferred that $L_3$ is a bond.

$R_{6a}$ is selected from a 5- to 6-membered heteroaryl ring, cyanophenyl, an 8- to 12-membered bicyclic heteroaryl ring, and a 4- to 12-membered heterocyclic ring. The 5- to 6-membered heteroaryl ring, 8- to 12-membered bicyclic heteroaryl ring, and 4- to 12-membered heterocyclic ring for $R_{6a}$ can be substituted or unsubstituted.

$R_{6b}$ is selected from hydrogen, a 5- to 6-membered heteroaryl ring, an aryl ring, an 8- to 12-membered bicyclic heteroaryl ring, and a 4- to 12-membered heterocyclic ring. The 5- to 6-membered heteroaryl ring, aryl ring, 8- to 12-membered bicyclic heteroaryl ring, and 4- to 12-membered heterocyclic ring for $R_{6b}$ can be substituted or unsubstituted.

Specific examples of 5- to 6-membered heteroaryl rings suitable for $R_{6a}$ and $R_{6b}$ include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl. Preferred 5- to 6-membered heteroaryl rings are, for example, pyrimidinyl, pyridinyl, and pyrazolyl. Each of the 5- to 6-membered heteroaryl rings is independently unsubstituted or substituted with substituents as described herein, for example as in the Examples or the Definitions.

Examples of 8- to 12-membered bicyclic heteroaryl rings suitable for $R_{6a}$ and $R_{6b}$ include, but are not limited to, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, thieno[3,2-b]pyridinyl, and pyrrolopyrimidinyl. Preferred 8- to 12-membered bicyclic heteroaryl rings are, for example, benzothiazolyl and thieno[3,2-b]pyridinyl. Each of the 8- to 12-membered bicyclic heteroaryl rings is independently unsubstituted or substituted with substituents as described herein, for example as in the Examples or the Definitions.

Examples of 4- to 12-membered heterocyclic rings suitable for $R_{6a}$ and $R_{6b}$ include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, tetrahydropyranyl, [1,3]dioxolanyl, azetidin-2-onyl, azepan-2-onyl, isoindolin-1,3-dionyl, (Z)-1H-benzo[e][1,4]diazepin-5(4H)-onyl, pyridazin-3(2H)-onyl, pyridin-2(1H)-onyl, pyrimidin-2(1H)-onyl, pyrimidin-2,4(1H,3H)-dionyl, pyrrolidin-2-onyl, benzo[d]thiazol-2(3H)-onyl, pyridin-4(1H)-onyl, imidazolidin-2-onyl, 1H-imidazol-2(3H)-onyl, piperidin-2-onyl, tetrahydropyrimidin-2(1H)-onyl, [1,2,4]thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, and 1H-benzo[d]imidazol-2(3H)-onyl. Preferred 4- to 12-membered heterocyclic rings are azetidin-2-onyl, azepan-2-onyl, pyridazin-3(2H)-onyl, pyrrolidin-2-onyl, and piperidin-2-onyl. Each of the heterocyclic rings is independently unsubstituted or substituted with substituents as described herein, for example as in the Examples or the Definitions.

In one preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 5- or 6-membered heteroaryl ring; and $R_2$, $R_3$, $R_{3a}$, $R_{3b}$, $R_4$, $R_5$, and L are as previously described In another preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 8- to 12-membered bicyclic heteroaryl ring; and $R_2$, $R_3$, $R_{3a}$, $R_{3b}$, $R_4$, $R_5$, and L are as previously described herein.

In another preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 4- to 12-membered heterocyclic ring; and $R_2$, $R_3$, $R_{3a}$, $R_{3b}$, $R_4$, $R_5$, and L are as previously described herein.

In another preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is pyridazin-3(2H)-onyl; and $R_2$, $R_3$, $R_{3a}$, $R_{3b}$, $R_4$, $R_5$, and L are as previously described herein.

Each of $R_3$, $R_{3a}$, and $R_{3b}$ are each independently selected from the group consisting of hydrogen, alkyl, trifluoroalkyl, trifluoroalkoxy, alkoxy, halogen, cyano, and thioalkoxy. Preferably, $R_3$, $R_{3a}$, and $R_{3b}$ are hydrogen, or, one of $R_3$, $R_{3a}$, and $R_{3b}$ is halogen and the others are hydrogen. The preferred halogen is fluorine.

$R_4$ and $R_5$ are each independently selected from the group consisting of alkyl, fluoroalkyl, hydroxyalkyl, alkoxyalkyl, and cycloalkyl. Alternatively, $R_4$ and $R_5$ taken together with the nitrogen atom to which each is attached to form a non-aromatic ring of the formula:

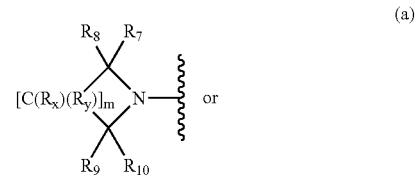

(a)

-continued

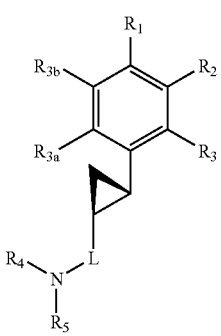

(b)

$R_7$, $R_8$, $R_9$, and $R_{10}$ are each independently selected from hydrogen, hydroxyalkyl, fluoroalkyl, cycloalkyl, and alkyl.

$R_x$ and $R_y$ at each occurrence are independently selected from the group consisting of hydrogen, hydroxy, hydroxyalkyl, alkyl, alkoxy, alkylamino, fluoro, and dialkylamino.

Preferably, at least one carbon in a group of formula (a) is substituted, such that either one of $R_7$, $R_8$, $R_9$, or $R_{10}$, or one of $R_x$ and $R_y$, is other than hydrogen. The preferred substituents for $R_7$, $R_8$, $R_9$, or $R_{10}$, when substituted, are hydroxyalkyl, fluoroalkyl, or alkyl. The preferred alkyl group is more particularly, methyl. The preferred substituents for $R_x$ or $R_y$, when substituted, are alkyl, fluoro, or hydroxy.

Groups of formula (a) are preferred for $R_4$ and $R_5$ when taken together to form a non-aromatic ring. The preferred group for $R_4$ and $R_5$ when taken together with the nitrogen atom to which each is attached to form a group of formula (a) is (2R)-methylpyrrolidine or (2S)-methylpyrrolidine.

$R_{11}$, $R_{12}$, $R_{13}$, and $R_{14}$ are each independently selected from hydrogen, hydroxyalkyl, alkyl, and fluoroalkyl. Preferably, at least three substituents selected from $R_{11}$, $R_{12}$, $R_{13}$, and $R_{14}$ are hydrogen.

Q is selected from O and S. The preferred atom for Q is oxygen.

The preferred group for $R_4$ and $R_5$ when taken together with the nitrogen atom to which each is attached to form a group of formula (b) is morpholinyl.

The variable m is an integer from 1 to 5.

L is $-[C(R_{16})(R_{17})]_k$, wherein $R_{16}$ and $R_{17}$ at each occurrence are independently selected from hydrogen and alkyl, and k is 1, 2 or 3. Preferably, k is 1 or 2.

One embodiment relates to compounds of formula (II):

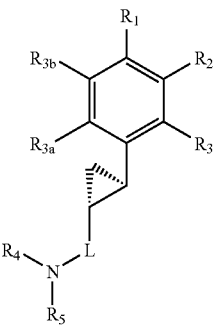

(II)

wherein L, $R_1$, $R_2$, $R_3$, $R_{3a}$, $R_{3b}$, $R_4$, and $R_5$ are as previously described.

In one preferred embodiment of compounds of the invention of formula (II), the group $R_1$ is $-L_2-R_{6a}-L_3-R_{6b}$, wherein $L_2$ is a bond; $R_{6b}$ is hydrogen; $L_3$ is a bond; $R_{6a}$ is selected from a 5- or 6-membered heteroaryl ring, or a 4- to 12-membered heterocyclic ring; $R_4$ and $R_5$, when taken together with the nitrogen atom to which each is attached, form a 4- to 8-membered non-aromatic ring represented by formula (a), and $R_2$, $R_3$, $R_{3a}$, $R_{3b}$, and L are as previously described.

Another embodiment relates to compounds of formula (III):

(III)

wherein L, $R_1$, $R_2$, $R_3$, $R_{3a}$, $R_{3b}$, $R_4$, and $R_5$ are as previously described.

In one preferred embodiment of compounds of the invention of formula (III), the group $R_1$ is $-L_2-R_{6a}-L_3-R_{6b}$, wherein $L_2$ is a bond; $R_{6b}$ is hydrogen; $L_3$ is a bond; $R_{6a}$ is selected from a 5- or 6-membered heteroaryl ring, or a 4- to 12-membered heterocyclic ring; $R_4$ and $R_5$ when taken together with the nitrogen atom to which each is attached to form a 4- to 8-membered non-aromatic ring represented by formula (a), and $R_2$, $R_3$, $R_{3a}$, $R_{3b}$, and L are as previously described.

Specific examples of compounds contemplated as within the scope of the invention include, but are not limited to, the following:

4'-((1S,2S)-2-{[(2S)-2-methylpyrrolidin-1-yl]methyl}cyclopropyl)-1,1'-biphenyl-4-carbonitrile;

4'-((1S,2S)-2-{[(2R)-2-methylpyrrolidin-1-yl]methyl}cyclopropyl)-1,1'-biphenyl-4-carbonitrile;

4'-((1R,2R)-2-{[(2R)-2-methylpyrrolidin-1-yl]methyl}cyclopropyl)-1,1'-biphenyl-4-carbonitrile;

4'-((1R,2R)-2-{[(2S)-2-methylpyrrolidin-1-yl]methyl}cyclopropyl)-1,1'-biphenyl-4-carbonitrile;

4'-{(1S,2S)-2-[(2-methylpyrrolidin-1-yl)methyl]cyclopropyl}-1,1'-biphenyl-4-carbonitrile;

5-[4-((1S,2S)-2-{[(2S)-2-methylpyrrolidin-1-yl]methyl}cyclopropyl)phenyl]pyrimidine;

2-methoxy-5-[4-((1S,2S)-2-{[(2S)-2-methylpyrrolidin-1-yl]methyl}cyclopropyl)phenyl]pyrimidine;

2,6-dimethyl-3-[4-((1S,2S)-2-{[(2R)-2-methylpyrrolidin-1-yl]methyl}cyclopropyl)phenyl]pyridine;

2-methoxy-5-[4-((1S,2S)-2-{[(2R)-2-methylpyrrolidin-1-yl]methyl}cyclopropyl)phenyl]pyridine;

5-[4-((1S,2S)-2-{[(2R)-2-methylpyrrolidin-1-yl]methyl}cyclopropyl)phenyl]pyrimidine;

5-[4-((1R,2R)-2-{[(2S)-2-methylpyrrolidin-1-yl]methyl}cyclopropyl)phenyl]pyrimidine;

5-[4-((1R,2R)-2-{[(2R)-2-methylpyrrolidin-1-yl]methyl}cyclopropyl)phenyl]pyrimidine;

2,4-dimethoxy-5-[4-((1R,2R)-2-{[(2S)-2-methylpyrrolidin-1-yl]methyl}cyclopropyl)phenyl]pyrimidine;

2,4-dimethoxy-5-[4-((1R,2R)-2-{[(2R)-2-methylpyrrolidin-1-yl]methyl}cyclopropyl)phenyl]pyrimidine-2,4-dimethoxy-5-[4-((1S,2S)-2-{[(2R)-2-methylpyrrolidin-1-yl]methyl}cyclopropyl)phenyl]pyrimidine;

2,4-dimethoxy-5-[4-((1S,2S)-2-{[(2S)-2-methylpyrrolidin-1-yl]methyl}cyclopropyl)phenyl]pyrimidine;

2-[4-((1R,2R)-2-{[(2S)-2-methylpyrrolidin-1-yl]
methyl}cyclopropyl)phenyl]pyridazin-3(2H)-one;
2-[4-((1S,2S)-2-{[(2S)-2-methylpyrrolidin-1-yl]
methyl}cyclopropyl)phenyl]pyridazin-3(2H)-one;
2-methyl-5-[4-((1S,2S)-2-{[(2S)-2-methylpyrrolidin-1-yl]
methyl}cyclopropyl)phenyl]-1,3-benzothiazole;
1,3,5-trimethyl-4-[4-((1S,2S)-2-{[(2S)-2-methylpyrrolidin-1-yl]methyl}cyclopropyl)phenyl]-1H-pyrazole;
2,6-dimethyl-3-[4-((1S,2S)-2-{[(2S)-2-methylpyrrolidin-1-yl]methyl}cyclopropyl)phenyl]pyridine;
N-[4-((1S,2S)-2-{[(2S)-2-methylpyrrolidin-1-yl]
methyl}cyclopropyl)phenyl]pyrimidin-5-amine;
4'-((1R,2S)-2-{2-[(2R)-2-methylpyrrolidin-1-yl]
ethyl}cyclopropyl)-1,1'-biphenyl-4-carbonitrile;
4'-((1S,2R)-2-{2-[(2R)-2-methylpyrrolidin-1-yl)methyl]cyclopropyl}-1,1'-biphenyl-4-carbonitrile;
4'-[(trans)-2-(2-pyrrolidin-1-ylethyl)cyclopropyl]-1,1'-biphenyl-4-carbonitrile;
N-[4-((1S,2S)-2-{[(2S)-2-methylpyrrolidin-1-yl]
methyl}cyclopropyl)phenyl]-5-(trifluoromethyl)thieno[3,2-b]pyridine-6-carboxamide;
N-[4-((1S,2S)-2-{[(2S)-2-methylpyrrolidin-1-yl]
methyl}cyclopropyl)phenyl]isonicotinamide;
2-[4-((1S,2S)-2-{[(2R)-2-methylpyrrolidin-1-yl]
methyl}cyclopropyl)phenyl]pyridazin-3(2H)-one;
1-[4-((1S,2S)-2-{[(2R)-2-methylpyrrolidin-1-yl]
methyl}cyclopropyl)phenyl]piperidin-2-one;
1-[4-((1S,2S)-2-{[(2R)-2-methylpyrrolidin-1-yl]
methyl}cyclopropyl)phenyl]azepan-2-one;
1-[4-((1S,2S)-2-{[(2R)-2-methylpyrrolidin-1-yl]
methyl}cyclopropyl)phenyl]pyrrolidin-2-one;
1-[4-((1S,2S)-2-{[(2R)-2-methylpyrrolidin-1-yl]
methyl}cyclopropyl)phenyl]azetidin-2-one;
1-[4-((1S,2S)-2-{[(2S)-2-methylpyrrolidin-1-yl]
methyl}cyclopropyl)phenyl]azetidin-2-one;
1-[4-((1S,2S)-2-{[(2S)-2-methylpyrrolidin-1-yl]
methyl}cyclopropyl)phenyl]azepan-2-one;
1-[4-((1S,2S)-2-{[(2S)-2-methylpyrrolidin-1-yl]
methyl}cyclopropyl)phenyl]piperidin-2-one;
1-[4-((1S,2S)-2-{[(2S)-2-methylpyrrolidin-1-yl]
methyl}cyclopropyl)phenyl]pyrrolidin-2-one;
N-[4-((1S,2S)-2-{[(2S)-2-methylpyrrolidin-1-yl]
methyl}cyclopropyl)phenyl]acetamide; and
N-[4-((1S,2S)-2-{[(2S)-2-methylpyrrolidin-1-yl]
methyl}cyclopropyl)phenyl]-1H-1,2,4-triazole-3-carboxamide.

The following compounds can be made according to the methods and Schemes described herein:
5-(pyrrolidin-1-ylcarbonyl)-2-{4-[(trans)-2-(2-pyrrolidin-1-ylethyl)cyclopropyl]phenyl}pyridine;
4'-{(1S,2R)-2-[2-(2-methylpyrrolidin-1-yl)ethyl]cyclopropyl}-1,1'-biphenyl-4-carbonitrile;
4'-((1S,2R)-2-{2-[(3R)-3-hydroxypyrrolidin-1-yl]
ethyl}cyclopropyl)-1,1'-biphenyl-4-carbonitrile;
4'-((1S,2R)-2-{2-[(2S)-2-(hydroxymethyl)pyrrolidin-1-yl]
ethyl}cyclopropyl)-1,1'-biphenyl-4-carbonitrile;
4'-[(1S,2R)-2-(2-azepan-1-ylethyl)cyclopropyl]-1,1'-biphenyl-4-carbonitrile; and
4'-[(1S,2R)-2-(2-morpholin-4-ylethyl)cyclopropyl]-1,1'-biphenyl-4-carbonitrile.

More preferred embodiments are compounds selected from:
2-methoxy-5-[4-((1S,2S)-2-{[(2S)-2-methylpyrrolidin-1-yl]
methyl}cyclopropyl)phenyl]pyrimidine;
2-[4-((1S,2S)-2-{[(2S)-2-methylpyrrolidin-1-yl]
methyl}cyclopropyl)phenyl]pyridazin-3(2H)-one;
(S)-3-hydroxy-1-(4-((1S,2S)-2-(((S)-2-methylpyrrolidin-1-yl)methyl)cyclopropyl)phenyl)pyrrolidin-2-one;
2-{4-[(1S,2S)-2-((S)-2-Methyl-pyrrolidin-1-ylmethyl)-cyclopropyl]-phenyl}-2H-pyridazin-3-one with (2S,3S)-2,3-dihydroxy-succinic acid; and
2-[4-((1S,2S)-2-{[(2R)-2-methylpyrrolidin-1-yl]
methyl}cyclopropyl)phenyl]pyridazin-3(2H)-one, or salts thereof.

Another more preferred embodiment relates to the compound 2-[4-((1S,2S)-2-{[(2S)-2-methylpyrrolidin-1-yl]
methyl}cyclopropyl)phenyl]pyridazin-3(2H)-one or a salt thereof.

Another more preferred embodiment related to the compound 2-[4-((1S,2S)-2-{[(2S)-2-methylpyrrolidin-1-yl]
methyl}cyclopropyl)phenyl]pyridazin-3(2H)-one and its L-bitartrate monohydrate, L-bitartrate anhydrate, D-bitartrate dihydrate, and D-bitartrate dihydrate.

Compounds of the invention were named by ACD/ChemSketch version 5.01 (developed by Advanced Chemistry Development, Inc., Toronto, ON, Canada) or were given names consistent with ACD nomenclature; alternatively, compounds were assigned names using ChemDraw (Cambridgesoft). The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Salt Properties

Particular salts of compounds of the invention also have been identified and are described herein. More particularly, such salts are 2-{4-[(1S,2S)-2-((S)-2-Methyl-pyrrolidin-1-ylmethyl)-cyclopropyl]-phenyl}-2H-pyridazin-3-one L-bitartrate monohydrate, L-bitartrate anhydrate, D-bitartrate dihydrate, and D-bitartrate anhydrate.

2-{4-[(1S,2S)-2-((S)-2-Methyl-pyrrolidin-1-ylmethyl)-cyclopropyl]-phenyl}-2H-pyridazin-3-one L-bitartrate monohydrate can be identified by characteristic peaks in its powder X-ray diffraction pattern (FIG. 1). One with skill in the art of analytical chemistry would be able to readily identify 2-{4-[(1S,2S)-2-((S)-2-Methyl-pyrrolidin-1-ylmethyl)-cyclopropyl]-phenyl}-2H-pyridazin-3-one L-bitartrate monohydrate solid by as few as one characteristic peak in its powder X-ray diffraction pattern. Two-theta angle positions of characteristic peaks in a powder X-ray diffraction pattern for 2-{4-[(1S,2S)-2-((S)-2-Methyl-pyrrolidin-1-ylmethyl)-cyclopropyl]-phenyl}-2H-pyridazin-3-one L-bitartrate monohydrate are 7.157±0.20, 10.064±0.20, 14.356±0.20, 16.727±0.20, 19.198±0.20, 20.119±0.20, 21.222±0.20, 22.146±0.20, 24.048±0.20, and 24.574±0.20. The solid was also analyzed by thermal gravimetric analysis. The TGA (FIG. 2) shows the dehydration of 2-{4-[(1S,2S)-2-((S)-2-Methyl-pyrrolidin-1-ylmethyl)-cyclopropyl]-phenyl}-2H-pyridazin-3-one L-bitartrate monohydrate.

Figure 3:
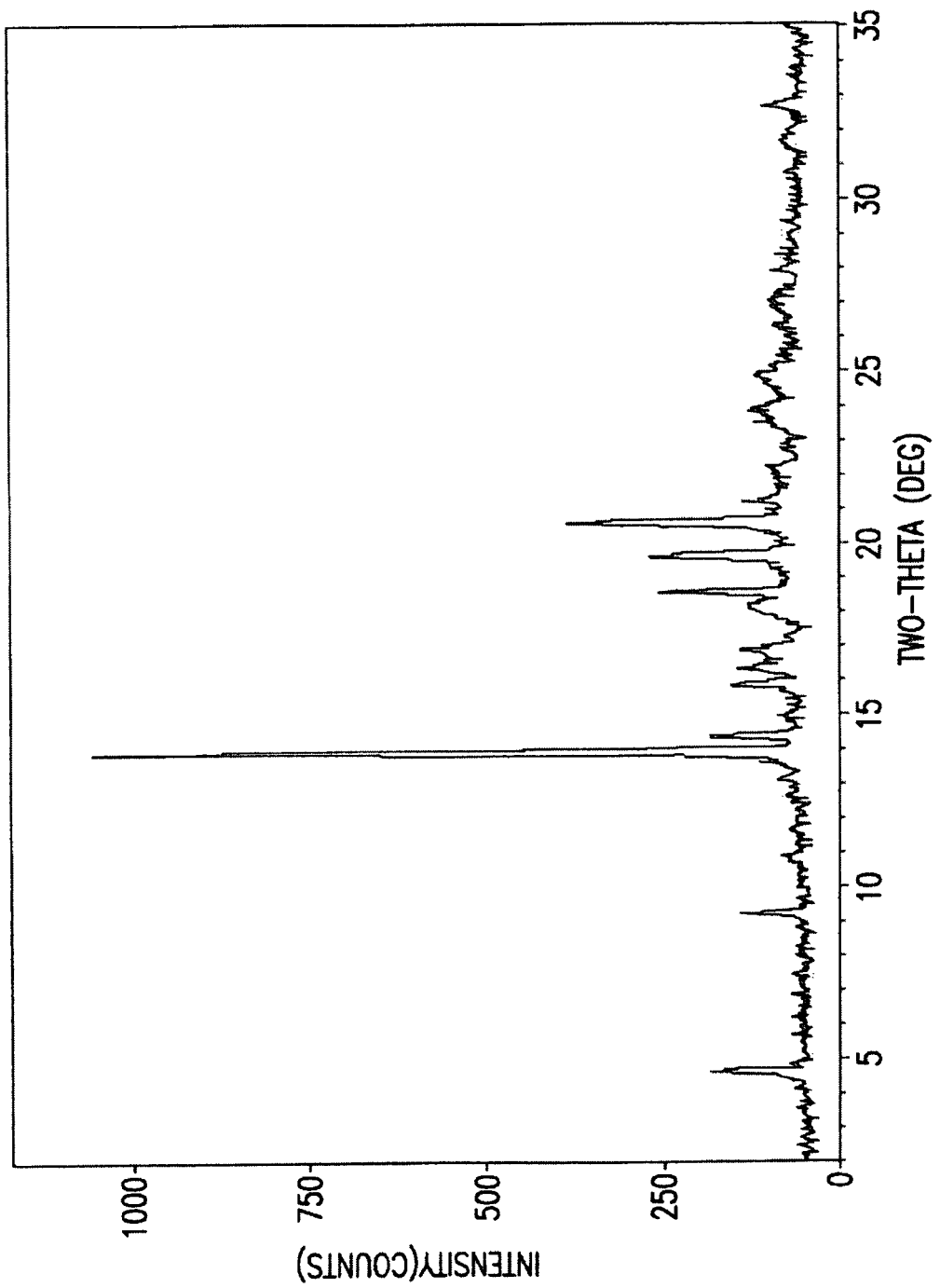
FIG. 3 is a powder X-ray diffraction pattern of 2-{4-[(1S,2S)-2-((S)-2-Methyl-pyrrolidin-1-ylmethyl)-cyclopropyl]-phenyl}-2H-pyridazin-3-one L-bitartrate anhydrate.

2-{4-[(1S,2S)-2-((S)-2-Methyl-pyrrolidin-1-ylmethyl)-cyclopropyl]-phenyl}-2H-pyridazin-3-one L-bitartrate anhydrate can be identified by characteristic peaks in its powder X-ray diffraction pattern (FIG. 3). One with skill in the art of analytical chemistry would be able to readily identify 2-{4-[(1S,2S)-2-((S)-2-Methyl-pyrrolidin-1-ylmethyl)-cyclopropyl]-phenyl}-2H-pyridazin-3-one L-bitartrate monohydrate solid by as few as one characteristic peak in its powder X-ray diffraction pattern. Two-theta angle positions in a powder X-ray diffraction pattern for 2-{4-[(1S,2S)-2-((S)-2-Methyl-pyrrolidin-1-ylmethyl)-cyclopropyl]-phenyl}-2H-pyridazin-3-one L-bitartrate anhydrate are 4.589±0.20, 9.206±0.20, 13.85±0.20, 14.335±0.20, 15.824±0.20, 16.272±0.20, 16.825±0.20, 18.083±0.20, 18.514±0.20, 19.588±0.20, and 20.551±0.20.

Figure 4:
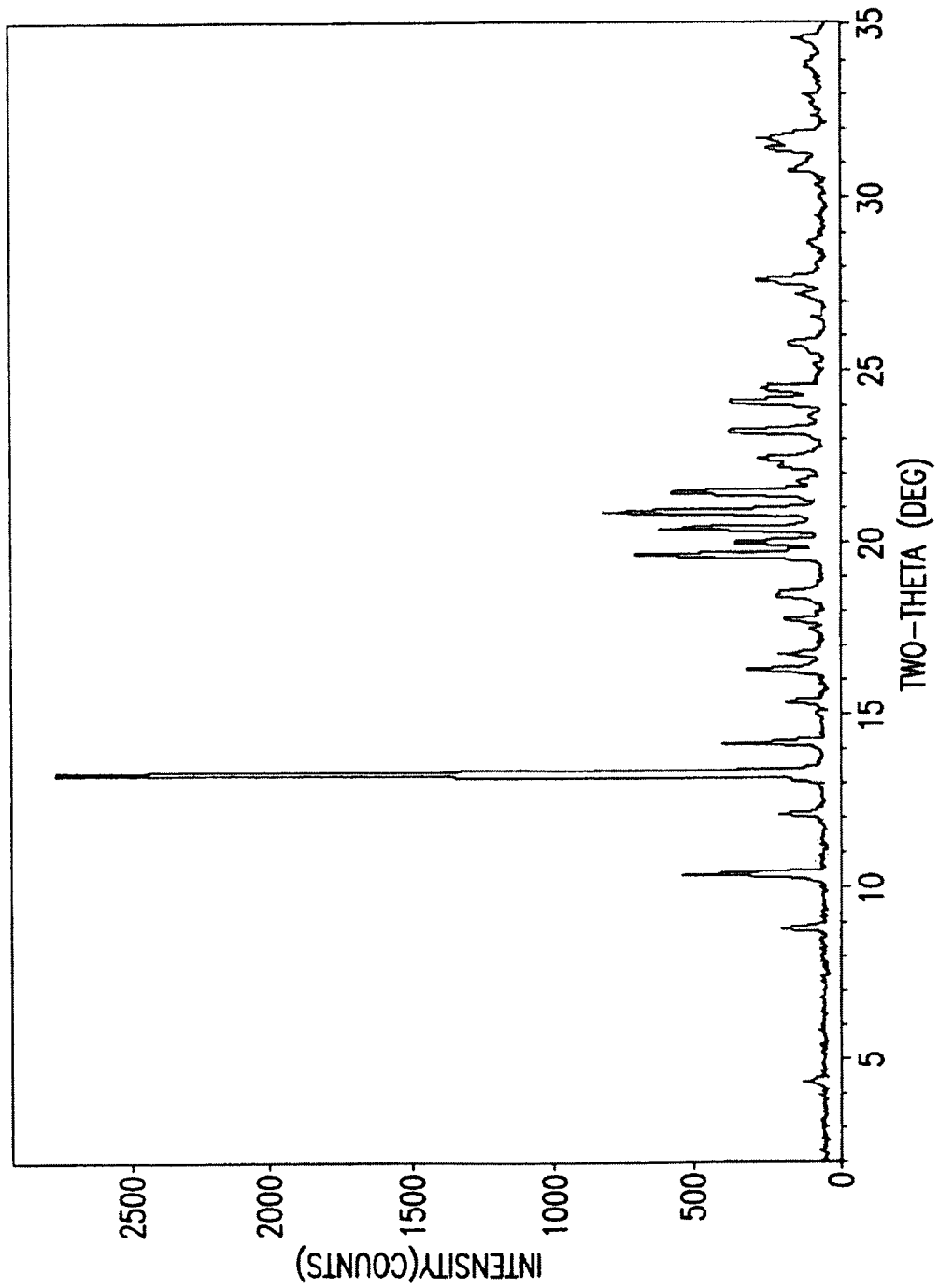
FIG. 4 is a powder X-ray diffraction pattern of 2-{4-[(1S,2S)-2-((S)-2-Methyl-pyrrolidin-1-ylmethyl)-cyclopropyl]-phenyl}-2H-pyridazin-3-one D-bitartrate dihydrate.

2-{4-[(1S,2S)-2-((S)-2-Methyl-pyrrolidin-1-ylmethyl)-cyclopropyl]-phenyl}-2H-pyridazin-3-one D-bitartrate dihydrate can be identified by characteristic peaks in its powder X-ray diffraction pattern (FIG. 4). One with skill in the art of analytical chemistry would be able to readily identify 2-{4-[(1S,2S)-2-((S)-2-Methyl-pyrrolidin-1-ylmethyl)-cyclopropyl]-phenyl}-2H-pyridazin-3-one D-bitartrate dihydrate solid by as few as one characteristic peak in its powder X-ray diffraction pattern. Two-theta angle peak positions in a powder X-ray diffraction pattern for 2-{4-[(1S,2S)-2-((S)-2-Methyl-pyrrolidin-1-ylmethyl)-cyclopropyl]-phenyl}-2H-pyridazin-3-one D-bitartrate dihydrate are 4.387±0.20, 8.788±0.20, 10.326±0.20, 12.056±0.20, 13.192±0.20, 14.089±0.20, 16.194±0.20, 19.502±0.20, 19.877±0.20, 20.271±0.20, 20.736±0.20, 21.313±0.20, 23.103±0.20, and 23.937±0.20, The solid was also analyzed by thermal gravimetric analysis. The TGA (FIG. 5) shows the dehydration of 2-{4-[(1S,2S)-2-((S)-2-Methyl-pyrrolidin-1-ylmethyl)-cyclopropyl]-phenyl}-2H-pyridazin-3-one D-bitartrate dihydrate.

Figure 6:
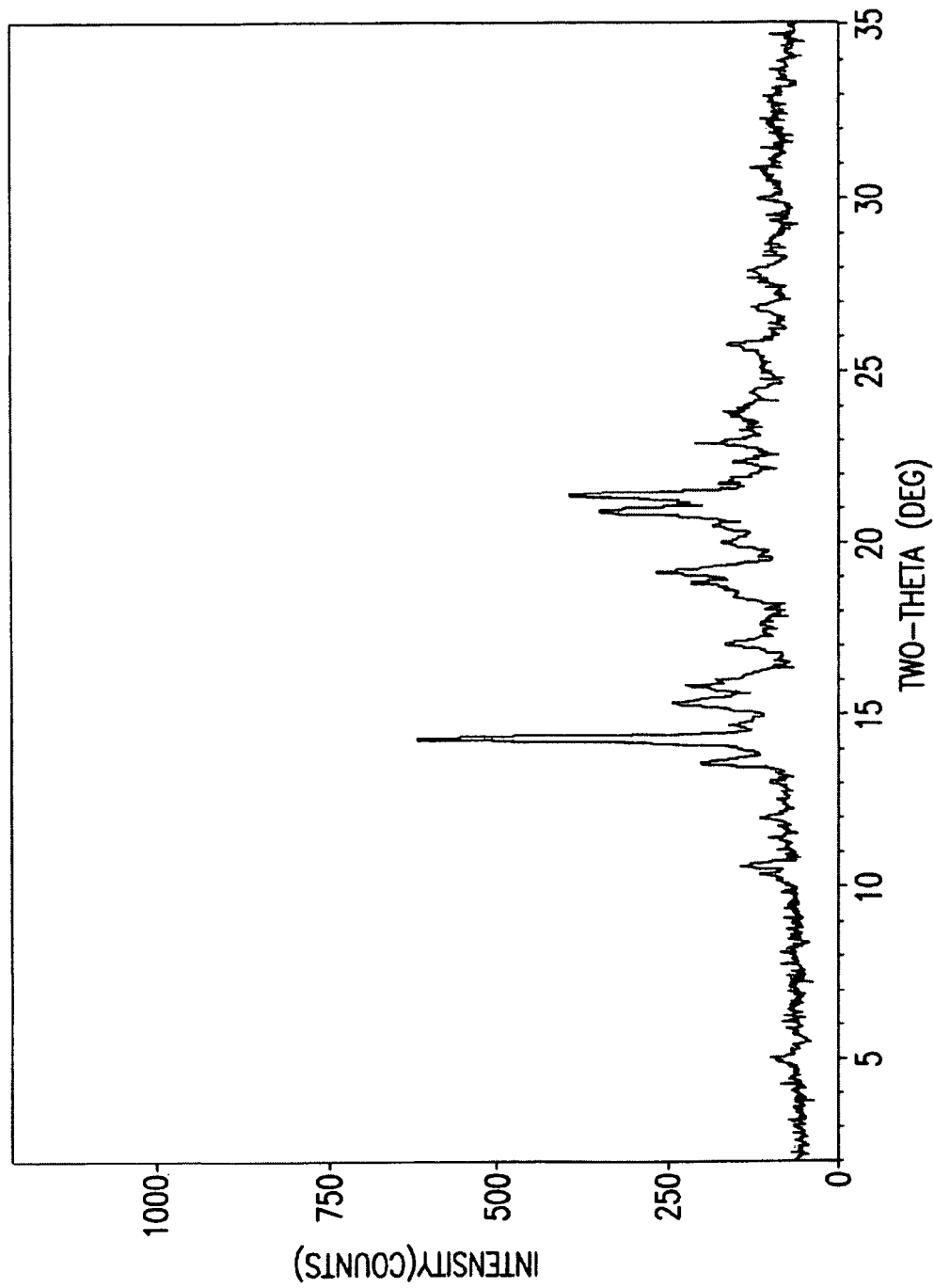
FIG. 6 is a powder X-ray diffraction pattern of 2-{4-[(1S,2S)-2-((S)-2-Methyl-pyrrolidin-1-ylmethyl)-cyclopropyl]-phenyl}-2H-pyridazin-3-one D-bitartrate anhydrate.

2-{4-[(1S,2S)-2-((S)-2-Methyl-pyrrolidin-1-ylmethyl)-cyclopropyl]-phenyl}-2H-pyridazin-3-one D-bitartrate anhydrate can be identified by characteristic peaks in its powder X-ray diffraction pattern (FIG. 6). One with skill in the art of analytical chemistry would be able to readily identify 2-{4-[(1S,2S)-2-((S)-2-Methyl-pyrrolidin-1-ylmethyl)-cyclopropyl]-phenyl}-2H-pyridazin-3-one D-bitartrate anhydrate solid by as few as one characteristic peak in its powder X-ray diffraction pattern. Two-theta angle peak positions in a powder X-ray diffraction pattern for 2-{4-[(1S,2S)-2-((S)-2-Methyl-pyrrolidin-1-ylmethyl)-cyclopropyl]-phenyl}-2H-pyridazin-3-one D-bitartrate anhydrate are 5.004±0.20, 10.590±0.20, 13.548±0.20, 14.219±0.20, 15.279±0.20, 15.723±0.20, 16.990±0.20, 18.723±0.20, 19.052±0.20, 20.827±0.20, 21.293±0.20, and 22.826±0.20.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Ac for acetyl; atm for atmosphere(s); AIBN for 2,2'-azobis(2-methylpropionitrile); BINAP for 2,2'-bis(diphenylphosphino)-1,1'-binaphthyl; Boc for butyloxycarbonyl; Bu for butyl; dba for dibenzylidineactone; DBU for 1,8-diazabicyclo[5.4.0]undec-7-ene; DCM for dichloromethane; DIBAL-H for diisobutylaluminum hydride; DMAP for 4-(N,N-dimethylamino)pyridine; DME for 1,2-dimethoxyethane; DMF for N,N-dimethylformamide; DMSO for dimethylsulfoxide; dppf for 1,1'-bis(diphenylphosphino)ferrocene; EDTA for ethylenediaminetetraacetic acid; Et for ethyl; EtOH for ethanol; EtOAc for ethyl acetate; HPLC for high pressure liquid chromatography; IPA for isopropyl alcohol; IPAC or IPAc for isopropyl acetate; LDA for lithium diisopropylamide; NBS for N-bromosuccinimide; NIS for N-iodosuccinimide; Me for methyl; MeOH for methanol; Ms for methanesulfonyl; MTBE for tert-butyl methyl ether; Pd for palladium; Ph for phenyl; tBu for tert-butyl; TE buffer for a combination Tris and EDTA buffer; TEA for triethylamine; TFA for trifluoroacetic acid; THF for tetrahydrofuran; Tris for 2-amino-2-hydroxymethyl-1,3-propanediol; and Ts for para-toluenesulfonyl; rt for "room temperature" or ambient temperature suitably ranging 15-40° C. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to, Schemes 1-7.

Scheme 1
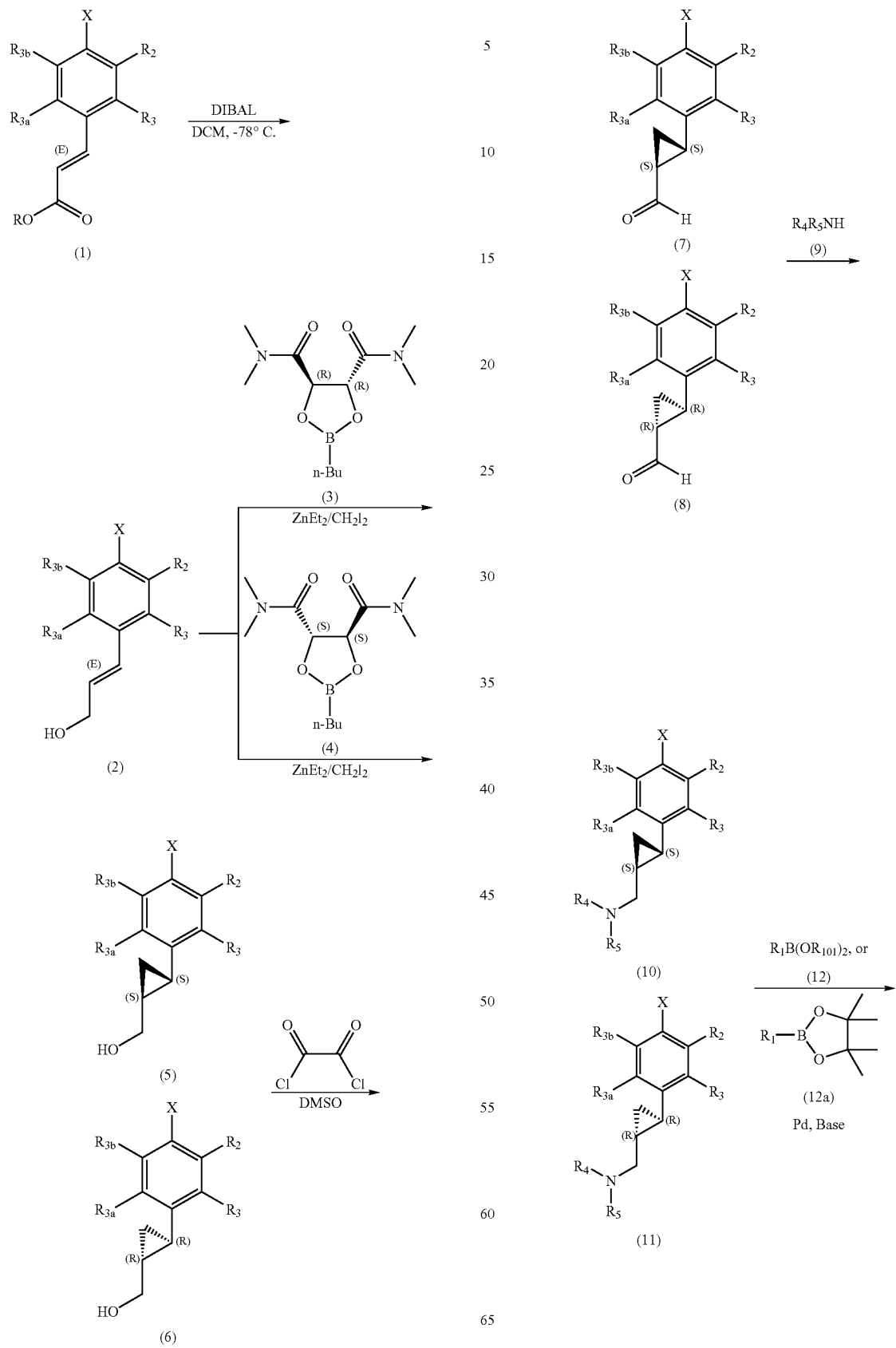

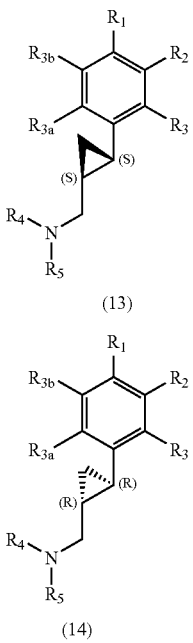

(13)

(14)

Compounds of formulas (13) and (14), wherein $R_3$, $R_{3a}$, $R_{3b}$, $R_4$, and $R_5$ are as defined in formula (I), $R_1$ is -$L_2$-$R_{6a}$-$L_3$-$R_{6b}$, and $R_2$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are as defined in formula (I), can be prepared as described in Scheme 1. Esters of formula (1) wherein R is a lower alkyl, and X is Cl, Br, I, or triflate, purchased or prepared using methodologies known to those of ordinary skills in the art, can be reduced with a reducing agent such as, but not limited to, DIBAL to provide allylic alcohols of formula (2). Allylic alcohols of formula (2) can be converted to cyclopropyl alcohols of formula (5) and (6) following the methodology of A. Charette, J. Org. Chem. 1998. The cyclopropyl alcohols of formulas (5) and (6) can be oxidized via a reaction known as Swern oxidation, by an agent, such as, but not limited to, DMSO and oxalyl chloride to provide aldehydes of formula (7) and (8). References describe this methodology may be found in the following: Tidwell, Thomas T. Organic Reactions (New York) (1990), 39 297-572 and the references cited in the article. Aldehydes of formulas (7) and (8) can be treated with reducing agents such as, but not limited to, sodium cyanoborohydride or sodium triacetoxyborohydride, in the presence of an amine of formula (9), via a reaction known as reductive amination, to provide amines of formula (10) and (11) respectively. References that describe this methodology may be found in the following: M. D. Bomann et al., J. Org. Chem., 60:5995-5960 (1995); A. E. Moormann et al., Synth. Commun., 23:789-795 (1993); and A. Pelter et al., J. Chem. Soc., PT I, 4:717-720 (1984); A. F. Abdel-Magid et al., *J. Org. Chem.* 1996, 61, 3849-3862.

The Suzuki reaction can be used to convert amines of formula (10) and (11) respectively to compounds of formula (13) and (14), wherein $R_3$, $R_{3a}$, $R_{3b}$, $R_4$, and $R_5$ are as defined in formula (I), $R_2$ is hydrogen, alkyl, alkoxy, halogen, cyano, or thioalkoxy, and $R_1$ is -$L_2$-$R_{6a}$-$L_3$-$R_{6b}$, wherein $L_2$ is a bond and $R_{6a}$, and $L_3$ and $R_{6b}$ are as defined in formula (I). In such a Suzuki reaction, amines of formula (13) and (14), wherein X is triflate, I, Br, or Cl can be reacted with boronic acids or boronic esters of formula (12) wherein $R_{101}$ is hydrogen or alkyl, a metal catalyst such as, but not limited to, palladium diacetate or Pd(PPh$_3$)$_4$, optionally with a Pd ligand added such as 2-(dicyclohexylphosphino)biphenyl or tris(2-furyl) phosphine, and a base such as, but not limited to, aqueous 0.2 M $K_3PO_4$ or sodium carbonate.

Alternatively, pinacol borane reagents such as, but not limited to, those represented by formula (12a) can be used in place of boronic acids or esters of formula (12) in the Suzuki reaction. References that describe the preparation and use of such reagents useful in the Suzuki reaction methodology may be found in the following: N. Miyaura et al., Chem. Rev. 95:2457 (1995) and references cited in the article.

There are many aryl, heteroaryl, and heterocyclic boronic acids and boronic acid esters that are available commercially or that can be prepared as described in the scientific literature of synthetic organic chemistry. Examples of boronic acid and boronic acid ester reagents for the synthesis of compounds of formula (I) are provided, but not limited to, reagents shown in Table 1, below, and the following description.

TABLE 1

Examples of Boronic Acid and Boronic Acid Ester Reagents

| Boronic Acid or Boronic Acid Ester | Commercial Source, Chemical Abstracts Number (CAS #), or Literature Reference |
|---|---|
| 2-pyrimidinone-5-boronic acid | CAS #373384-19-1 |
| 2-methoxypyrimidine-5-boronic acid | Frontier Scientific, Inc., Logan, UT, USA |
| 1H-pyrimidine-2,4-dione-5-boronic acid | Specs, Fleminglaan, the Netherlands CAS #70523-22-7; Schinazi, Raymond F.; Prusoff, William H., Synthesis of 5-(dihydroxyboryl)-2'-deoxyuridine and related boron-containing pyrimidines, Journal of Organic Chemistry (1985), 50(6), 841-7. |
| pyridine-3-boronic acid | CAS #1692-25-7, Frontier Scientific, Inc., Logan, UT, USA |
| 2,4-dimethoxypyrimidine-5-boronic acid | CAS #89641-18-9, Frontier Scientific, Inc., Logan, UT, USA |
| 2-methoxy-5-pyridine boronic acid | Digital Specialty Chemicals, Dublin, NH; CAS #163105-89-3; New shelf-stable halo- and alkoxy-substituted pyridylboronic acids and their Suzuki cross-coupling reactions to yield heteroarylpyridines, Parry, Paul R.; Bryce, Martin R.; Tarbit, Brian, Department of Chemistry, Synthesis (2003), (7), 1035-1038; Functionalized Pyridylboronic Acids and Their |

TABLE 1-continued

Examples of Boronic Acid and Boronic Acid Ester Reagents

| Boronic Acid or Boronic Acid Ester | Commercial Source, Chemical Abstracts Number (CAS #), or Literature Reference |
|---|---|
| pyrimidine-5-boronic acid | Suzuki Cross-Coupling Reactions To Yield Novel Heteroarylpyridines, Parry, Paul R.; Wang, Changsheng; Batsanov, Andrei S.; Bryce, Martin R.; Tarbit, Brian, Journal of Organic Chemistry (2002), 67(21), 7541-7543. CAS #109299-78-7, S. Gronowitz, et al., "On the synthesis of various thienyl- and selenienylpyrimidines", Chem. Scr. 26(2): 305-309 (1986). |
| pyrimidine-5-boronic acid, pinacol ester | Umemoto, et al., Angew. Chem. Int. Ed. 40(14): 2620-2622 (2001). |
| 2-methylpyridine-5-boronic acid hydrate | SYNCHEM OHG Heinrich-Plett-Strassse 40; Kassel, D-34132; Germany; CAS #659742-21-9 |
| 2H-Pyran, 3,6-dihydro-4-(4,4,5,5-tetramethyl-1,3,2-dioxaborolan-2-yl) | CAS # 287944-16-5; Murata, Miki; Oyama, Takashi; Watanabe, Shinji; Masuda, Yuzuru, Synthesis of alkenylboronates via palladium-catalyzed borylation of alkenyl triflates (or iodides) with pinacolborane. Synthesis(2000), (6), 778-780. |
| 1(2H)-Pyridinecarboxylic acid, 3,6-dihydro-4-(4,4,5,5-tetramethyl-1,3,2-dioxaborolan-2-yl)-, 1,1-dimethylethyl ester | CAS # 286961-14-6; A versatile synthesis of 4-aryltetrahydropyridines via palladium mediated Suzuki cross-coupling with cyclic vinyl boronates, Eastwood, Paul R., Discovery Chemistry, Aventis Pharma, Essex, UK., Tetrahedron Letters (2000), 41(19), 3705-3708. |
| (5-cyano-3-pyridinyl)-boronic acid | CAS # 497147-93-0; Chemstep Institut du PIN - University Bordeaux 1 351 cours de la liberation Talence Cedex, 33450 France |

Boronic acids or boronic acid esters of formula (12), and (12a) can be prepared from corresponding halides or triflates via either (1) metal exchange with an organo lithium agent followed with addition of alkyl borate or pinacolborate or (2) cross coupling with a reagent such as, but not limited to, bis(pinacolato)diboron (CAS #73183-34-3). References that describe the first methodology may be found in the following: B. T. O'Neill, et al., Organic Letters, 2:4201 (2000); M. D. Sindkhedkar, et al., Tetrahedron, 57:2991 (2001); W. C. Black, et al., J. Med. Chem., 42:1274 (1999); R. L. Letsinger et al., J. Amer. Chem. Soc., 81:498-501 (1959); and F. 1. Carroll et al., J. Med. Chem., 44: 2229-2237 (2001). References that describe the second methodology may be found in the following: T. Ishiyama et al., Tetrahedron, 57:9813-9816 (2001); T. Ishiyama et al., J. Org. Chem., 60:7508-7510 (1995); and Takagi et al., Tetrahedron Letters, 43:5649-5651 (2002).

Another method for preparation of boronic acids and boronic acid esters is the reaction described in O. Baudoin, et al., J. Org. Chem., 65:9268-9271 (2000), in which aryl and heteroaryl halides or triflates are reacted with a dialkyloxyborane such as pinacolborane, in the presence of triethylamine and palladium (II) acetate in dioxane.

Alternatively, utilizing other coupling methods such as Stille coupling, compounds of formulas (13) and (14) wherein $R_3$, $R_{3a}$, $R_{3b}$, $R_4$, and $R_5$ are as defined in formula (I), $R_2$ is hydrogen, alkyl, alkoxy, halogen, cyano or thioalkoxy, and $R_1$ is $-L_2-R_{6a}-L_3-R_{6b}$, wherein $L_2$ is a bond and $R_{6a}$, $L_3$, and $R_{6b}$ are as defined in formula (I), can be prepared from amines of formulas (10) and (11) respectively, by treatment with organostannanes of formula $(R_{102})_3SnR_1$ wherein $R_{102}$ is alkyl or aryl, in the presence of a palladium source such as tris(dibenzylidineacetone)dipalladium (CAS # 52409-22-0) or palladium diacetate, and a ligand such as tri(2-furyl)phosphine (CAS # 5518-52-5) or triphenylarsine. The reaction is generally performed in a solvent such as DMF at a temperature from about 25° C. to about 150° C. Such methods are described, for instance, in J. K. Stille Angew. Chem. Int. Ed. 25:508 (1986) and T. N. Mitchell, Synthesis, 803 (1992).

While many stannanes are commercially available or described in the literature that support the Stille coupling reaction where compounds of formulas (10) and (11) can be transformed to compounds of formulas (13) and (14), respectively, it is also possible to prepare new stannanes from arylhalides, aryltriflates, heteroarylhalides, and heteroaryltriflates by reaction with hexa-alkyl distannanes of formula $((R_{102})_3Sn)_2$ wherein $R_{102}$ is alkyl or aryl, in the presence of a palladium source like $Pd(Ph_3P)_4$. Example of hexa-alkyl distannanes include, but not limited to, hexamethyldistannane (CAS # 661-69-8). Such methods are described, for instance in Krische, et. al., Helvetica Chimica Acta 81(11): 1909-1920 (1998), and in Benaglia, et al., Tetrahedron Letters 38:4737-4740 (1997). These reagents can be reacted with (10) and (11) to afford compounds of formulas (13) and (14) respectively as described under Stille conditions, or for example under the conditions reported by A. F. Littke et al., J. of Amer. Chem. Soc. 124:6343-6348 (2002).

Compounds of formulas (13) and (14) wherein $R_3$, $R_{3a}$, $R_{3b}$, $R_4$, and $R_5$ are as defined in formula (I), $R_2$ is hydrogen, alkyl, alkoxy, halogen, cyano or thioalkoxy, and $R_1$ is $-L_2-R_{6a}-L_3-R_{6b}$, wherein $L_3$ and $R_{6b}$ are as defined in formula (I), $L_2$ is a bond, and $R_{6a}$ is a nitrogen-containing heteroaryl or heterocyclic ring linked to the parent moiety through the nitrogen, can be prepared by heating compounds of formulas (10) and (11) respectively, with heteroaryl or heterocyclic rings of formula H—$R_{6a}L_3R_{6b}$ wherein H is a hydrogen on the nitrogen atom, in the presence of a base such as, but not limited to, sodium t-butoxide or cesium carbonate, a metal catalyst such as, but not limited to copper metal or CuI, palladium diacetate, and optionally with a ligand such as, but not limited to, BINAP or tri-tertbutylphosphine. The reaction can be conducted in a solvent such as, but not limited to, dioxane, toluene or pyridine. References that describe these methods may be found in the following: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174 (2000); F. Y. Kwong et al., Org. Lett., 4:581-584 (2002); A. Klapars et al., J. Amer. Chem. Soc., 123:7727-7729 (2001); B. H. Yang et al., J. Organomet. Chem., 576:125-146 (1999); and A. Kiyomori et al., Tet. Lett., 40:2657-2640 (1999).

Compounds of formulas (13) and (14) wherein $R_3$, $R_{3a}$, $R_{3b}$, $R_4$ and $R_5$ are as defined in formula (I), $R_2$ is hydrogen, alkyl, alkoxy, halogen, cyano, or thioalkoxy, and $R_1$ is -$L_2$-$R_{6a}$-$L_3$-$R_{6b}$, wherein $L_2$ is —NH— or —N(alkyl)-, and $R_{6a}$, $R_{6b}$, and $L_3$ are as defined for a compound of formula (I) can be prepared by heating compounds of formula (10) and (11) respectively, with a compound of formula $H_2N$—$R_{6a}$-$L_3$-$R_{6b}$ or $HN(alkyl)$-$R_{6a}$-$L_3$-$R_{6b}$ with a base such as, but not limited to, sodium t-butoxide or cesium carbonate in the presence of a metal catalyst such as, but not limited to, copper metal or CuI, palladium diacetate, and also optionally with a ligand such as, but not limited to, BINAP, or tri-tert-butylphosphine. The reaction can be performed in a solvent such as dioxane, toluene, or pyridine. References that describe these methodologies may be found in the following: J. Hartwig, et al., Angew. Chem. Int. Ed., 37:2046-2067 (1998); J. P. Wolfe et al., Acc. Chem. Res., 13:805-818 (1998); J. P. Wolfe et al., J. Org. Chem., 65:1158-1174 (2000); F. Y. Kwong et al., Org. Lett., 4:581-584 (2002); and B. H. Yang et al., J. Organomet. Chem., 576:125-146 (1999).

Compounds of formulas (13) and (14) wherein $R_3$, $R_{3a}$, $R_{3b}$, $R_4$ and $R_5$ are as defined in formula (I), $R_2$ is hydrogen, alkyl, alkoxy, halogen, cyano, or thioalkoxy, and $R_1$ is $L_2$-$R_{6a}$-$L_3$-$R_{6b}$, wherein $L_2$ is oxygen and $R_{6a}$, and $L_3$ and $R_{6b}$ are as defined in formula (I) can be prepared by heating compounds of formula (10) and (11) respectively with a compound of formula $HOR_{6a}$-$L_3$-$R_{6b}$ using a base such as, but not limited to, sodium hydride in a solvent such as toluene or N,N-dimethylformamide, in the presence of a metal containing catalyst such as CuI or palladium diacetate. References that describe these methodologies may be found in the following: J. Hartwig et al., Angew. Chem. Int. Ed., 37:2046-2067 (1998); K. E. Torraca et al., J. Amer. Chem. Soc., 123: 10770-10771 (2001); S. Kuwabe et al., J. Amer. Chem. Soc., 123:12202-12206 (2001); K. E. Toracca et al., J. Am. Chem. Soc., 122:12907-12908 (2000); R. Olivera et al., Tet. Lett., 41:4353-4356 (2000); J.-F. Marcoux et al., J. Am. Chem. Soc., 119:10539-10540 (1997); A. Aranyos et al., J. Amer. Chem. Soc., 121:43694378 (1999); T. Satoh et al., Bull. Chem. Soc. Jpn., 71:2239-2246 (1998); J. F. Hartwig, Tetrahedron Lett., 38:2239-2246 (1997); M. Palucki et al., J. Amer. Chem. Soc., 119:3395-3396 (1997); N. Haga et al, J. Org. Chem., 61:735-745 (1996); R. Bates et al., J. Org. Chem., 47:4374-4376 (1982); T. Yamamoto et al., Can. J. Chem., 61:86-91 (1983); A. Aranyos et al., J. Amer. Chem. Soc., 121:4369-4378 (1999); and E. Baston et al., Synth. Commun., 28:2725-2730 (1998).

Compounds of formulas (13) and (14) wherein $R_3$, $R_{3a}$, $R_{3b}$, $R_4$ and $R_5$ are as defined in formula (I), $R_2$ is hydrogen, alkyl, alkoxy, halogen, cyano, orthioalkoxy, and $R_1$ is $L_2$-$R_{6a}$-$L_3$-$R_{6b}$, wherein $L_2$ is sulfur and $R_{6a}$, and $L_3$ and $R_{6b}$ are as defined for a compound of formula (I) can be prepared by heating compounds of formula (10) and (11) respectively with a compound of formula $HSR_{6a}$-$L_3$-$R_{6b}$ in the presence of a base, and with or without a metal catalyst such as CuI or palladium diacetate, in a solvent such as dimethylformamide or toluene. References that describe these methodologies may be found in the following: G. Y. $L_1$ et al., J. Org. Chem., 66:8677-8681 (2001); Y. Wang et al., Bioorg. Med. Chem. Lett., 11:891-894 (2001); G. Liu et al., J. Med. Chem., 44:1202-1210 (2001); G. Y. Li et al., Angew. Chem. Int. Ed., 40:1513-1516 (2001); U. Schopfer et al., Tetrahedron, 57:3069-3074 (2001); and C. Palomo et al., Tet. Lett., 41:1283-1286 (2000); A. Pelter et al., Tet. Lett., 42:8391-8394 (2001); W. Lee et al., J. Org. Chem., 66:474-480 (2001); and A. Toshimitsu et al., Het. Chem., 12:392-397 (2001).

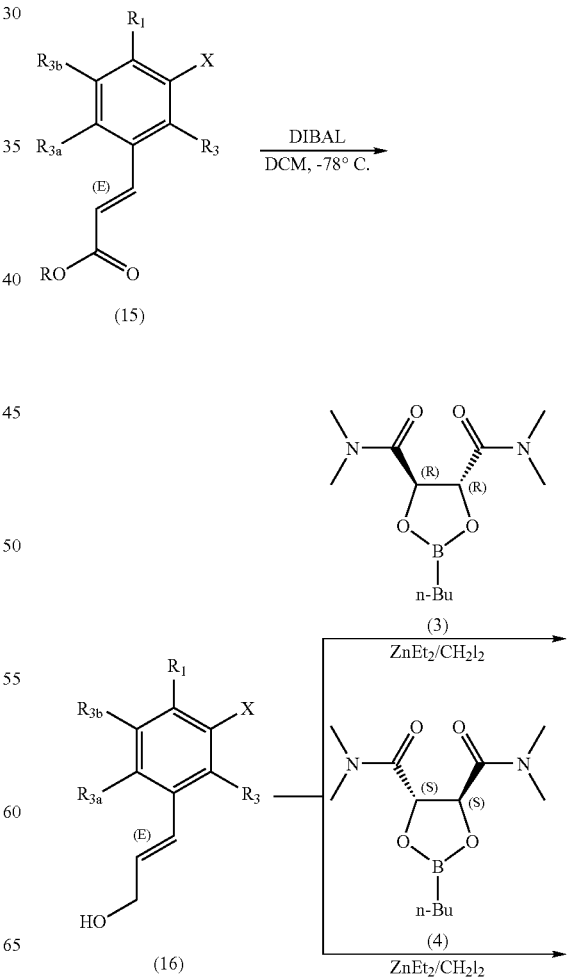

Scheme 2

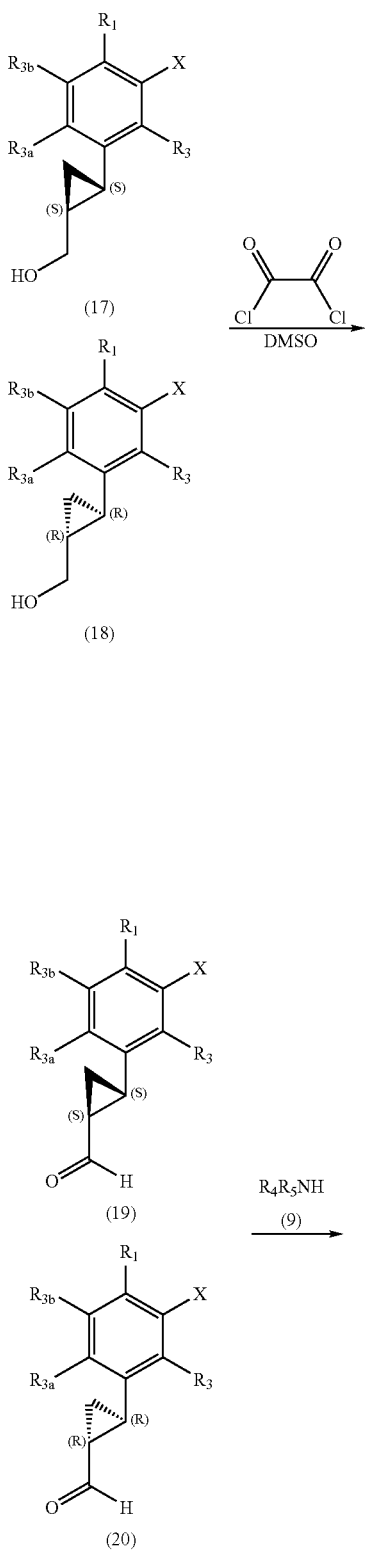
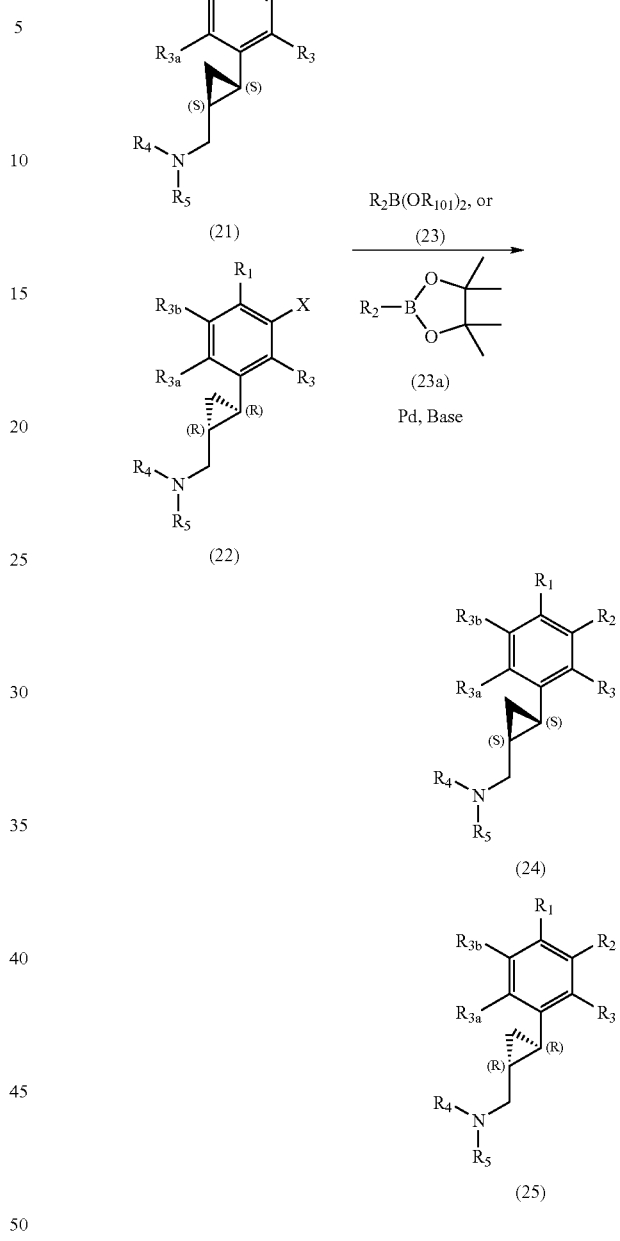

Similarly, compounds of formulas (24) and (25) wherein $R_3$, $R_{3a}$, $R_{3b}$, $R_4$ and $R_5$ are as defined in formula (I), $R_1$ is hydrogen, alkyl, alkoxy, halogen, cyano, or thioalkoxy, and $R_2$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 2, from compounds of formula (15) wherein R is a lower alkyl, X is Cl, Br, I, or triflate, using the reaction conditions that are outlined in Scheme 1, except for substituting boronic acid or esters of formula (23) for (12) and pinacol borane reagents of formula (23a) for (12a) for the Suzuki reactions, and except for substituting organostannes of formula $(R_{102})_3SnR_2$ for $(R_{102})_3SnR_1$ for Stille coupling. References that describe the Suzuki reaction methodology may be found in the following: N. Miyaura et al., Chem. Rev. 95:2457 (1995) and references cited in the article.

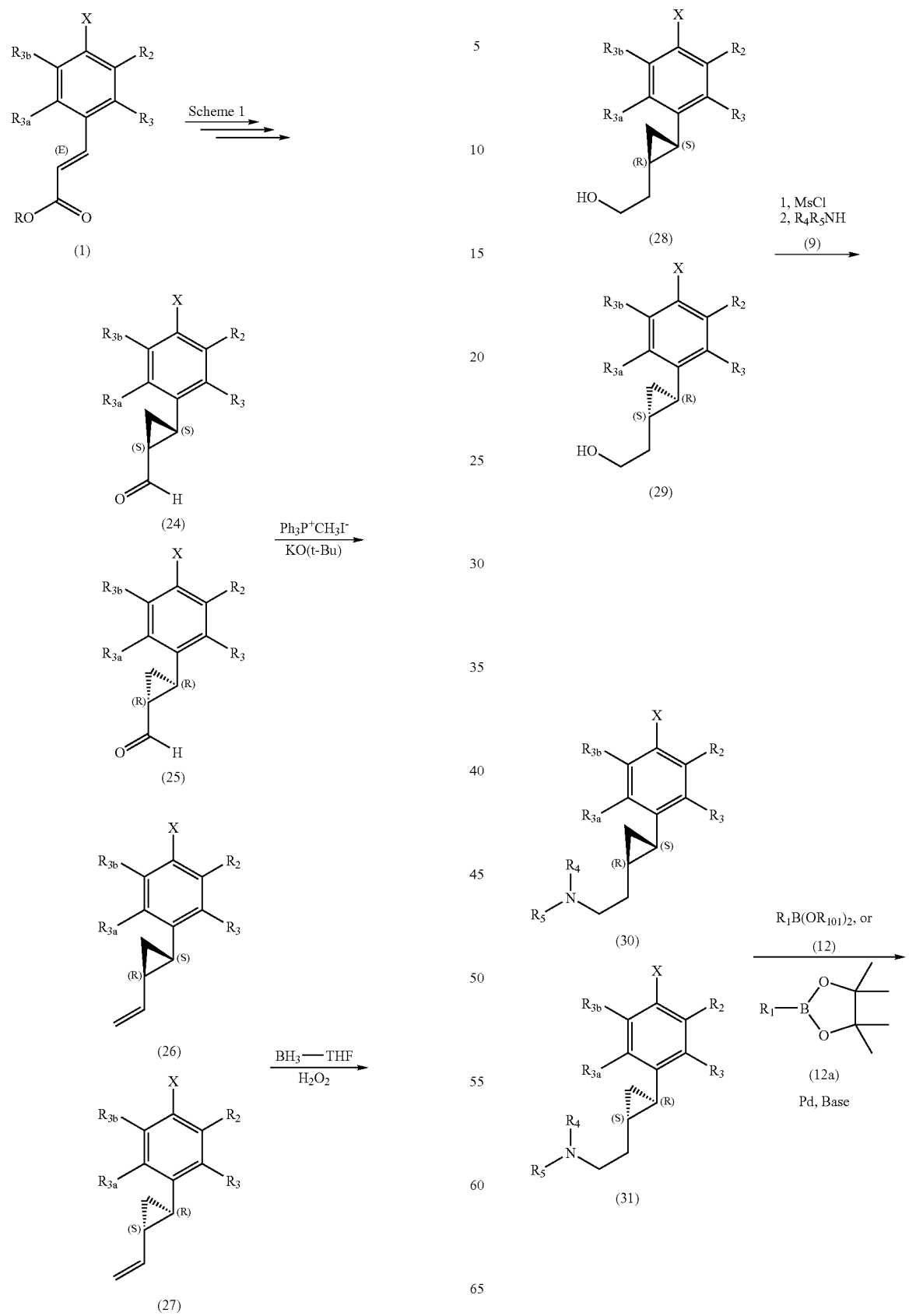

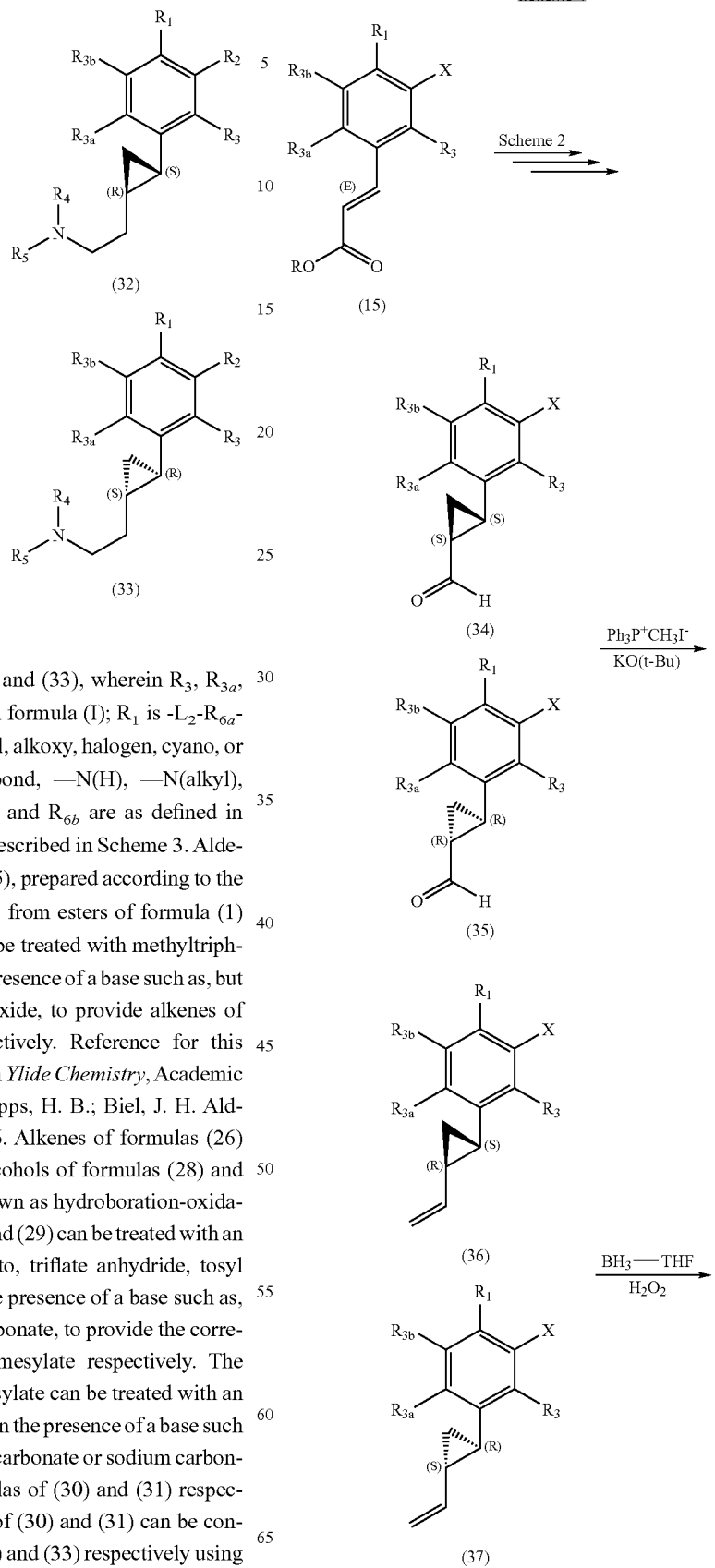

Scheme 4

Compounds of formulas (32) and (33), wherein $R_3$, $R_{3a}$, $R_{3b}$, $R_4$, and $R_5$ are as defined in formula (I); $R_1$ is -$L_2$-$R_{6a}$-$L_3$-$R_{6b}$, and $R_2$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are as defined in formula (I), can be prepared as described in Scheme 3. Aldehydes of formulas of (24) and (25), prepared according to the reaction conditions in Scheme 1 from esters of formula (1) wherein R is a lower alkyl, can be treated with methyltriphenylphosphonium iodide in the presence of a base such as, but not limited to, potassium t-butoxide, to provide alkenes of formulas (26) and (27) respectively. Reference for this method may be found in: Johnson *Ylide Chemistry*, Academic Press: New York, 1966, and Hopps, H. B.; Biel, J. H. Aldrichimica Acta (1969), 2(2), 3-6. Alkenes of formulas (26) and (27) can be converted to alcohols of formulas (28) and (29) via a reaction sequence known as hydroboration-oxidation. Alcohols of formulas (28) and (29) can be treated with an agent such as, but not limited to, triflate anhydride, tosyl chloride, or mesyl chloride in the presence of a base such as, but not limited to, potassium carbonate, to provide the corresponding triflate, tosylate, or mesylate respectively. The resulting triflate, tosylate, or mesylate can be treated with an amine of formula (9), optionally in the presence of a base such as, but not limited to, potassium carbonate or sodium carbonate, to provide amines of formulas of (30) and (31) respectively. Compounds of formulas of (30) and (31) can be converted to amines of formulas (32) and (33) respectively using the reaction conditions described in Scheme 1.

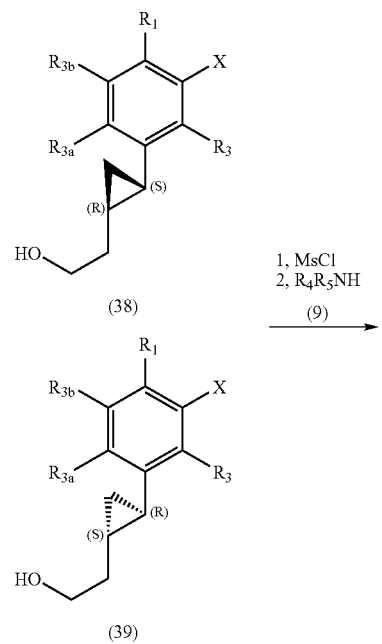

(38)

(39)

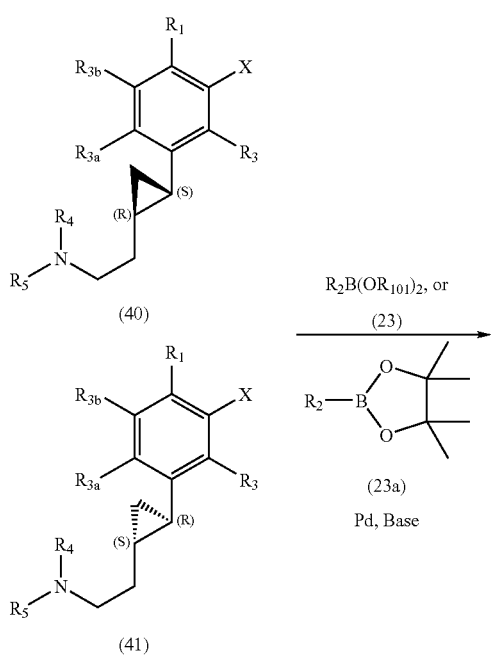

(40)

(41)

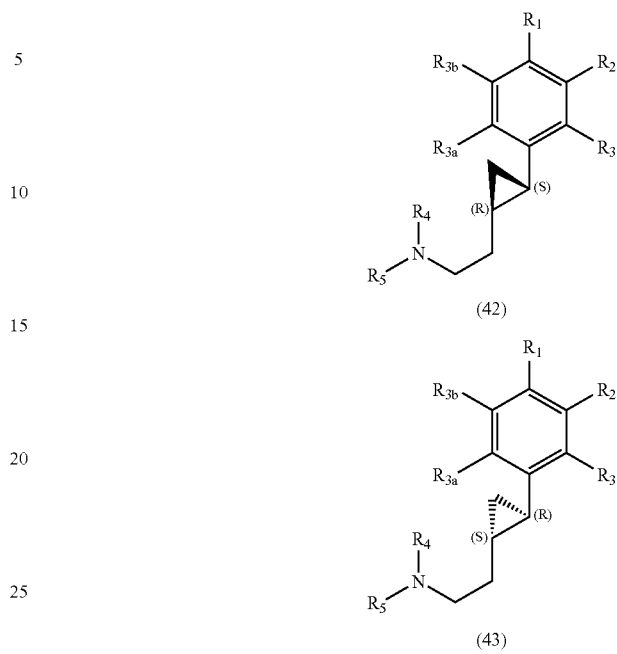

(42)

(43)

Similarly, compounds of formulas (42) and (43), wherein $R_3$, $R_{3a}$, $R_{3b}$, $R_4$, and $R_5$ are as defined in formula (I); $R_2$ is -$L_2$-$R_{6a}$-$L_3$-$R_{6b}$, and $R_1$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are as defined in formula (I), can be prepared as described in Scheme 4. Esters of formula (15) wherein R is a lower alkyl, X is Br, Cl, or I, can be converted to amines of formulas (42) and (43), using the reaction conditions as described in Scheme 3, except for substituting boronic acid or esters of formula (12) for (23) and pinacol borane reagents of formula (12a) for (23a) for the Suzuki reactions, and except for substituting organostannes of formula $(R_{102})_3SnR_2$ for $(R_{102})_3SnR_1$ for Stille coupling.

Scheme 5

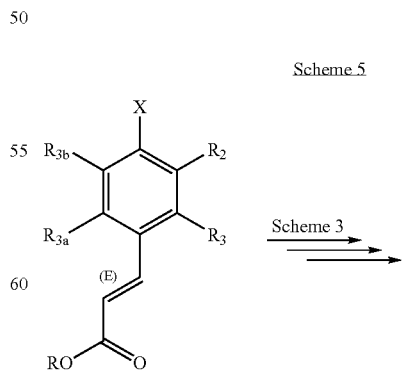

(1)

-continued

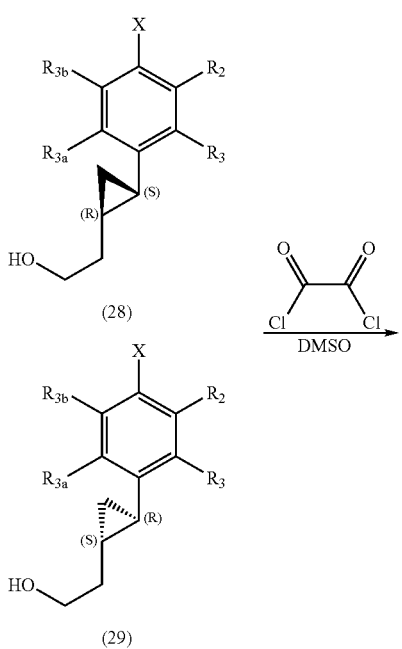

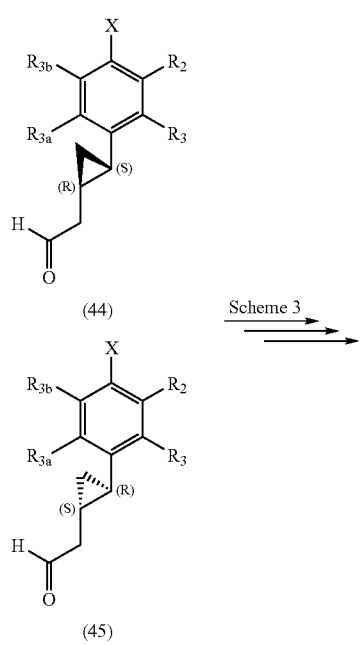

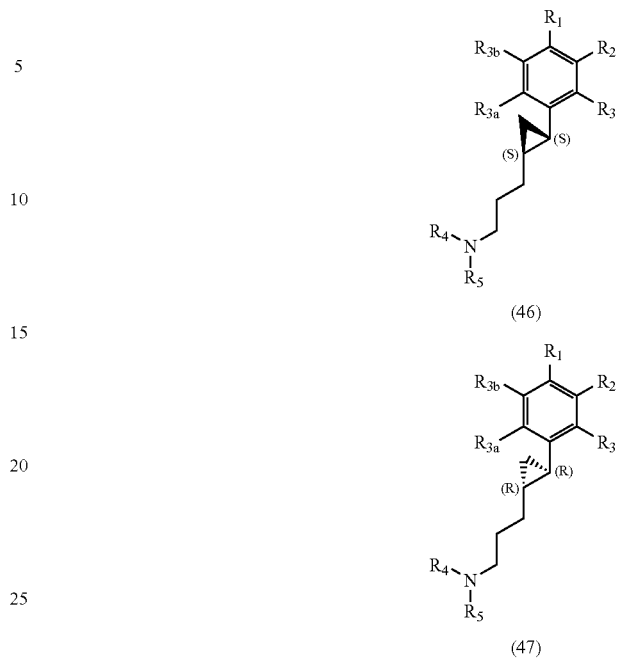

Compounds of formulas (46) and (47), wherein $R_3$, $R_{3a}$, $R_{3b}$, $R_4$, and $R_5$ are as defined in formula (I); $R_2$ is hydrogen, alkyl, alkoxy, halogen, cyano, or thioalkoxy; and $R_1$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 5. Esters of formula (1) wherein R is a lower alkyl, X is Br, Cl, or I, can be converted to alcohols of formulas (28) and (29) according Scheme 3. Alcohols of formulas (28) and (29) can be oxidized via a reaction known as Swern oxidation, by an agent, such as, but not limited to, DMSO and oxalyl chloride in the presence of a base such as triethylamine to provide aldehydes of formulas (44) and (45). Aldehydes of formulas (44) and (45) can be converted to amines of formulas (46) and (47) respectively using the reaction conditions described in Scheme 3 transforming compounds of formulas (24) and (25) to compounds of formulas (32) and (33).

Scheme 6

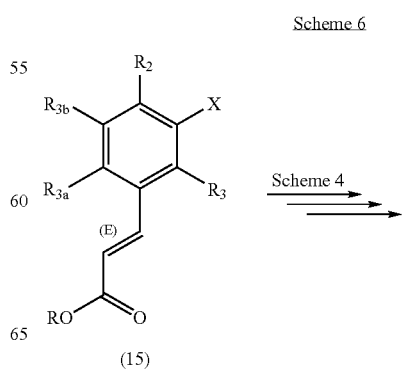

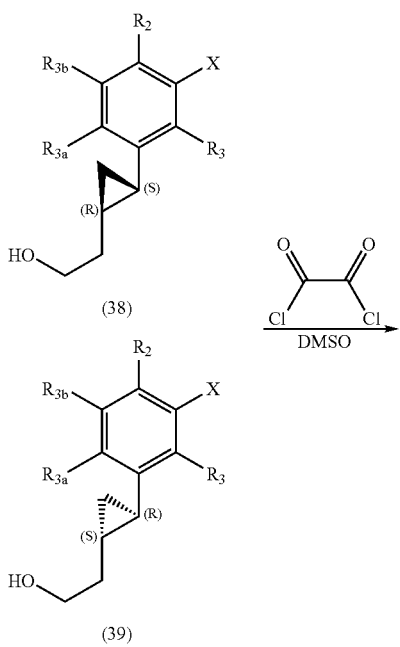

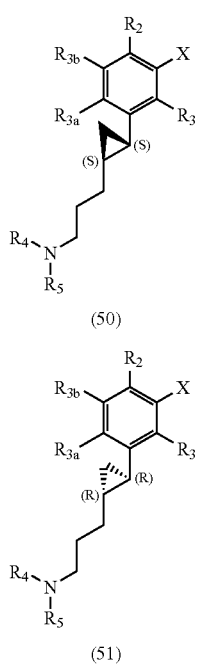

Similarly, compounds of formulas (50) and (51), wherein $R_3$, $R_{3a}$, $R_{3b}$, $R_4$, and $R_5$ are as defined in formula (I); $R_1$ is hydrogen, alkyl, alkoxy, halogen, cyano, or thioalkoxy; and $R_2$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 6. Esters of formula (15) wherein R is a lower alkyl, X is Br, Cl, or I, can be converted to alcohols of formulas (38) and (39) as described in Scheme 4. Alcohols of formulas (38) and (39) can be oxidized via a reaction known as Swern oxidation, by an agent, such as, but not limited to, DMSO and oxalyl chloride to provide aldehydes of formulas (48) and (49) respectively. Aldehydes of formulas (48) and (49) can be converted to amines of formulas (50) and (51), respectively, using the reaction conditions described in Scheme 4 transforming compounds of formulas (38) and (39) to compounds of formulas (42) and (43).

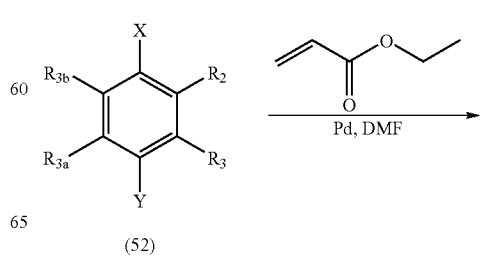

-continued

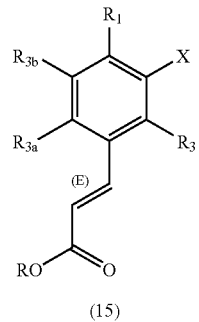

(1)

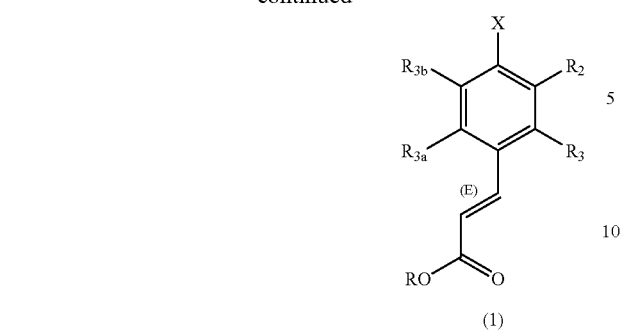

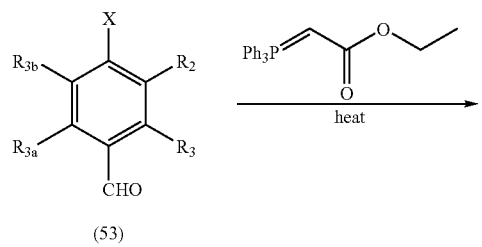

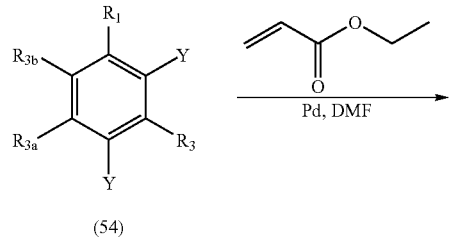

Esters of formula (1) wherein X is I, Br or Cl or hydroxy; R is a lower alkyl; $R_3$, $R_{3a}$, and $R_{3b}$ are as defined in formula (I); and $R_2$ is hydrogen, alkyl, alkoxy, halogen, cyano, or thioalkoxy; can be purchased or prepared as described in Scheme 7. Halides of formula (52), wherein Y is I, Br, or triflate (prepared by the treatment of phenols with triflate anhydride), can be treated with ethyl acrylate in the presence of a palladium source such as dichlorobis(triphenylphosphine)palladium(II) (CAS# 13965-03-2) or tris(dibenzylideneacetone)dipalladium (CAS # 52409-22-0) or palladium diacetate, and a ligand such as tri(2-furyl)phosphine (CAS # 5518-52-5) or triphenyl phosphine, in a solvent such as DMF at 25-150° C. to provide the esters of formula (1).

Alternatively, esters of formula (1) can be prepared through substituted benzaldehydes of formula (53) via the Wittig reaction, which is well-known to those skilled in the art of organic synthesis. References that describe these methods may be found in the following: S. Li et al., Chemische Berichte, 123:1441-1442 (1990); T. Kauffmann et al., Tetrahedron Lett., 22:5031-5034 (1981).

Similarly, esters of formula (15) wherein X is I, Br or Cl or hydroxy; R is a lower alkyl; $R_3$, $R_{3a}$, and $R_{3b}$ are as defined in formula (I); and $R_1$ is hydrogen, alkyl, alkoxy, halogen, cyano, or thioalkoxy; can be purchased or prepared as described in Scheme 7.

The compounds and intermediates of the invention may be isolated and purified by methods well-known to those skilled in the art of organic synthesis.

Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby a desired salt of the compound can be formed by treatment of the compound with an acid. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzensulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, bitartrate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound containing the carboxylic acid group with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart, et al. *J. Med. Chem.* 2005, 48, 38-55; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161; Yates, et al. JPET (1999) 289, 1151-1159 "Identification and Pharmacological Characterization of a Series of New 1H-4-Substituted-Imidazoyl Histamine $H_3$ Receptor Ligands"; Ligneau, et al. Journal of Pharmacology and Experimental Therapeutics (1998), 287, 658-666; Tozer, M. Expert Opinion Therapeutic Patents (2000) 10, 1045; M. T. Halpern, "GT-2331" Current Opinion in Central and Peripheral Nervous System Investigational Drugs (1999) 1, 524-527; Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002); Glase, S. A., et al. "Attention deficit hyperactivity disorder: pathophysiology and design of new treatments." Annual Reports in Medicinal Chemistry (2002), 37 11-20; Schweitzer, J. B., and Holcomb, H. H. "Drugs under investigation for attention-deficit hyperactivity disorder" Current Opinion in Investigative Drugs (2002) 3, 1207.

The ability of the compounds of the invention, including, but not limited to, those specified in the examples, to treat dementia, and diseases with deficits of memory and learning, may be demonstrated by "Two novel and selective nonimidazole $H_3$ receptor antagonists A-304121 and A-317920: II. In vivo behavioral and neurophysiological characterization." Fox, G. B., et al. Journal of pharmacology and experimental therapeutics (2003 June), 305(3), 897-908; "Identification of novel $H_3$ receptor ($H_3R$) antagonist with cognition enhancing properties in rats." Fox, G. B.; Inflammation Research (2003), 52(Suppl. 1), S31-S32; Bernaerts, P., et al. "Histamine $H_3$ antagonist thioperamide dose-dependently enhances memory consolidation and reverses amnesia induced by dizocilpine or scopolamine in a one-trial inhibitory avoidance task in mice" Behavioural Brain Research 154 (2004) 211-219; Onodera, et al. Nauyn-Schmiedebergs' Arch. Pharmacol. (1998), 357, 508-513; Prast, et al. Brain Research (1996) 734, 316-318; Chen, et al. Brain Research (1999) 839, 186-189 "Effects of histamine on MK-801-induced memory deficits in radial maze performance in rats"; Passani, et al. "Central histaminergic system and cognition" Neuroscience and Biobehavioral Reviews (2000) 24, 107-113.

The ability of the compounds of the invention, including, but not limited to, those specified in the examples, to treat schizophrenia, cognitive deficits of schizophrenia, and cognitive deficits, may be demonstrated by Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190 and by "Enhancement of prepulse inhibition of startle in mice by the $H_3$ receptor antagonists thioperamide and ciproxifan." Browman, Kaitlin E., et al. Behavioural Brain Research (2004), 153(1), 69-76; "$H_3$ receptor blockade by thioperamide enhances cognition in rats without inducing locomotor sensitization."; Komater, V. A., et al. Psychopharmacology (Berlin, Germany) (2003), 167(4), 363-372; A A Rodrigues, F P Jansen, R Leurs, H Timmerman and G D Prell "Interaction of clozapine with the histamine $H_3$ receptor in rat brain" British Journal of Pharmacology (1995), 114(8), pp. 1523-1524; Passani, et al. "Central histaminergic system and cognition" Neuroscience and Biobehavioral Reviews (2000) 24, 107-113; Morriset, S., et al. "Atypical Neuroleptics Enhance Histamine Turnover in Brain Via 5-Hydroxytryptamine$_{2A}$ Receptor Blockade" Journal of Pharmacology and Experimental Therapeutics (1999) 288, 590-596.

The ability of the compounds of the invention, including, but not limited to, those specified in the examples, to treat dysfunction in psychiatric disorders, Alzheimer's disease, and mild cognitive impairment may be demonstrated by Meguro, et al. Pharmacology, Biochemistry and Behavior (1995) 50(3), 321-325; Esbenshade, T., et al. "Pharmacological and behavioral properties of A-349821, a selective and potent human histamine H3 receptor antagonist" Biochemical Pharmacology 68 (2004) 933-945; Huang, Y.-W., et al. "Effect of the histamine H3-antagonist clobenpropit on spatial memory deficits induced by MK-801 as evaluated by radial maze in Sprague-Dawley rats" Behavioural Brain Research 151 (2004) 287-293; Mazurkiewicz-Kwilecki and Nsonwah, Can. J. Physiol. Pharmacol. (1989) 67, 75-78; P. Panula, et al., Neuroscience (1997) 82, 993-997; Haas, et al., Behav. Brain Res. (1995) 66, 41-44; De Almeida and Izquierdo, Arch. Int. Pharmacodyn. (1986), 283, 193-198; Kamei et al., Psychopharmacology, (1990) 102, p. 312-318; Kamei and Sakata, Jpn. J. Pharmacol. (1991), 57, 437-482; Schwartz et al., Psychopharmacology, The Fourth Generation of Progress. Bloom and Kupfer (eds). Raven Press, New York, (1995) 397; and Wada, et al., Trends in Neurosci. (1991) 14, p. 415.

The ability of the compounds of the invention, including, but not limited to, those specified in the examples, to treat epilepsy, and seizures, may be demonstrated by Harada, C., et al. "Inhibitory effect of iodophenpropit, a selective histamine H3 antagonist, on amygdaloid kindled seizures" Brain Research Bulletin (2004) 63: 143-146; as well as by Yokoyama, et al., Eur. J. Pharmacol. (1993) 234: 129-133; Yokoyama, et al. European Journal of Pharmacology (1994) 260: 23; Yokoyama and Iinuma, CNS Drugs (1996) δ: 321; Vohora, Life Sciences (2000) 66: 297-301; Onodera et al., Prog. Neurobiol. (1994) 42: 685; Chen, Z., et al. "Pharmacological effects of carcinine on histaminergic neurons in the brain" British Journal of Pharmacology (2004) 143, 573-580; R. Leurs, R. C. Volling a and H. Timmerman, "The medicinal chemistry and therapeutic potential of ligands of the histamine $H_3$ receptor", Progress in Drug Research (1995) 45: 170-165; Leurs and Timmerman, Prog. Drug. Res. (1992) 39: 127; H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995); Yawata, et al. "Role of histaminergic neurons in development of epileptic seizures in EL mice" Molecular Brain Research 132 (2004) 13-17.

The ability of the compounds of the invention, including, but not limited to, those specified in the examples, to treat allergic rhinitis, and asthma, may be demonstrated by McLeod, R. L., Mingo, G. G., Herczku, C., DeGennaro-Culver, F., Kreutner, W., Egan, R. W., Hey, J. A., "Combined histamine H1 and H3 receptor blockade produces nasal decongestion in an experimental model of nasal congestion" Am. J. Rhinol. (1999a) 13: 391-399; McLeod, Robbie L.; Egan, Robert W.; Cuss, Francis M.; Bolser, Donald C.; Hey, John A. (Allergy, Schering-Plough Research Institute, Kenilworth, N.J., USA.) Progress in Respiratory Research (2001), 31 (in *New Drugs for Asthma, Allergy and COPD*): 133-136; A. Delaunois A., et al., "Modulation of acetylcholine, capsaicin and substance P effects by histamine $H_3$ receptors in isolated perfused rabbit lungs," European Journal of Pharmacology (1995) 277: 243-250; Dimitriadou, et al., "Functional relationship between mast cells and C-sensitive nerve fibres evidenced by histamine $H_3$-receptor modulation in rat lung and spleen," Clinical Science (1994), 87: 151-163.

The ability of the compounds of the invention, including, but not limited to, those specified in the examples, to treat motion sickness, dizziness, Meniere's disease, vestibular disorders, and vertigo, may be demonstrated by Pan, et al. Methods and Findings in Clinical Pharmacology (1998), 20(9), 771-777; O'Neill, et al. Methods and Findings in Clinical Pharmacology (1999) 21(4), 285-289; and by R. Leurs, R. C.

Volling a and H. Timmerman, "The medicinal chemistry and therapeutic potential of ligands of the histamine H$_3$ receptor," Progress in Drug Research (1995), 45: 170-165, Lozada, et al. "Plasticity of histamine H$_3$ receptor expression and binding in the vestibular nuclei after labyrinthectomy in rat" BioMed-Central Neuroscience 2004, 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A. A. "Antiobesity effects of A-331440, a novel non-imidazole histamine H3 receptor antagonist "European Journal of Pharmacology (2004) 487, 183-197; Hancock, A. A., et al." Histamine H$_3$ antagonists in models of obesity" Inflamm. res. (2004) 53, *Supplement* 1 S47-S48; as well as by E. Itoh, M. Fujimiay, and A. Inui, "Thioperamide, A histamine H$_3$ receptor antagonist, powerfully suppresses peptide YY-induced food intake in rats," Biol. Psych. (1999) 45(4): 475-481; S. I. Yates, et al., "Effects of a novel histamine H$_3$ receptor antagonist, GT-2394, on food intake and weight gain in Sprague-Dawley rats," Abstracts, Society for Neuroscience, 102.10:219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000); Sakata T; et al. "Hypothalamic neuronal histamine modulates ad libitum feeding by rats." Brain research (1990 Dec. 24), 537(1-2), 303-6.

The ability of the compounds of the invention, including, but not limited to, those specified in the examples, to treat pain, including neuropathic pain and neuropathy, may be demonstrated by Malmberg-Aiello, Petra; Lamberti, Claudia; Ghelardini, Carla; Giotti, Alberto; Bartolini, Alessandro. British Journal of Pharmacology (1994), 111(4), 1269-1279; Hriscu, Anisoara; Gherase, Florenta; Pavelescu, M.; Hriscu, E. "Experimental evaluation of the analgesic efficacy of some antihistamines as proof of the histaminergic receptor involvement in pain." Farmacia, (2001), 49(2), 23-30, 76.

The ability of the compounds of the invention, including, but not limited to, those specified in the examples, to treat sleep disorders, including narcolepsy and pathological sleepiness, and jet lag, may be demonstrated by Barbier, A. J., et al. "Acute wake-promoting actions of JNJ-5207852, a novel, diamine-based H$_3$ antagonist" British Journal of Pharmacology (2004) 1-13; Monti et al., Neuropsychopharmacology (1996) 15, 31-35; Lin et al., Brain Res. (1990) 523: 325-330; Monti, et al., Neuropsychopharmacology (1996) 15: 31-35; Ligneau, et al. Journal of Pharmacology and Experimental Therapeutics (1998), 287, 658-666; Sakai, et al., Life Sci. (1991) 48: 2397-2404; Mazurkiewicz-Kwilecki and Nsonwah, Can. J. Physiol. Pharmacol., (1989) 67: 75-78; P. Panula, et al., Neuroscience (1998) 44, 465-481; Wada, et al., Trends in Neuroscience (1991) 14: 415; and Monti, et al., Eur. J. Pharmacol. (1991), 205: 283; Dvorak, C., et al. "4-Phenoxypiperidines: Potent, Conformationally Restricted, Non-Imidazole Histamine H$_3$ Antagonists" Journal of Medicinal Chemistry (2005) 48, 2229-2238.

The ability of the compounds of the invention, including, but not limited to, those specified in the examples, to treat drug abuse. Amphetamine is an abused stimulant in humans. It, and similar abused drugs stimulate locomotor activity in animals, and it has been found that the H$_3$ antagonist thioperamide suppresses the locomotor stimulation induced by amphetamine; therefore H$_3$ antagonists are likely to be useful for treating drug abuse as may be demonstrated by Clapham J.; Kilpatrick G. J. "Thioperamide, the selective histamine H$_3$ receptor antagonist, attenuates stimulant-induced locomotor activity in the mouse", European journal of pharmacology (1994), 259(2), 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti, et al. British Journal of Pharmacology (1998) 123, 1331-1336; Perez-Garcia C, et. al., Psychopharmacology (Berlin) (1999) 142(2): 215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sánchez-Lemus, E., et al. "Histamine H$_3$ receptor activation inhibits dopamine D$_1$ receptor-induced cAMP accumulation in rat striatal slices" Neuroscience Letters (2004) 364, p. 179-184; Sakai, et al., Life Sci. (1991) 48, 2397-2404; Fox, G. B., et al. "Pharmacological Properties of ABT-239: II. Neurophysiological Characterization and Broad Preclinical Efficacy in Cognition and Schizophrenia of a Potent and Selective Histamine H$_3$ Receptor Antagonist" Journal of Pharmacology and Experimental Therapeutics, 313:176-190, 2005; Chen, Z., et al. "Pharmacological effects of carcinine on histaminergic neurons in the brain" British Journal of Pharmacology (2004) 143, 573-580.

The ability of the compounds of the invention, including, but not limited to, those specified in the examples, to treat medullary thyroid carcinoma, melanoma, polycystic ovary syndrome, may be demonstrated by Polish Med. Sci. Mon. (1998) 4(5): 747; Adam Szelag, "Role of histamine H$_3$-receptors in the proliferation of neoplastic cells in vitro," Med. Sci. Monitor (1998) 4(5):747-755; and C. H. Fitzsimons, et al., "Histamine receptors signalling in epidermal tumor cell lines with H-ras gene alterations," Inflammation Res. (1998) 47 (Suppl 1):S50-S51.

Compounds of the invention are particularly useful for treating and preventing a condition or disorder affecting attention-deficit hyperactivity, Alzheimer's disease, or dementia. Compounds of the invention are particularly useful for treating and preventing a condition or disorder affecting schizophrenia or cognitive deficits of schizophrenia. Compounds of the invention are particularly useful for treating and preventing a condition or disorder affecting narcolepsy, sleep disorders, allergic rhinitis, asthma, or obesity.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.001 to about 30 mg/kg of body weight. For purposes of oral administration, more preferable doses can be in the range of from about 0.001 to about 1 mg/kg body weight. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Example 1

4'-((1S,2S)-2-{[(2S)-2-Methylpyrrolidin-1-yl]methyl}cyclopropyl)-1,1'-biphenyl-4-carbonitrile Example 1A trans-3-(4-Bromophenyl)prop-2-en-1-ol To a solution of ethyl trans-4-bromocinnamate (8 mL, 42.6 mmol) in anhydrous dichloromethane (150 mL) under $N_2$ was added diisobutylaluminum hydride in dichloromethane (128 mL, 1 M, 128 mmol) at −78° C. dropwise. After the addition, the mixture was allowed to warm from −78° C. to −30° C. over two hours. The mixture was then cooled back to −78° C. and aqueous 1 N HCl was added till acidic (pH=2). The organic layer was separated and the aqueous layer was extracted with dichloromethane. The combined organic layers were dried with $MgSO_4$, filtered and concentrated under reduced pressure to provide the title compound. $^1$H NMR (300 MHz, $CDCl_3$): δ 1.44 (t, J=6 Hz, 1H), 4.32 (t, J=4.5 Hz, 2H), 6.37 (dt, J=16.5 Hz, J=6 Hz, 1H), 6.57 (dt, J=15 Hz, J=3 Hz, 1H), 7.25 (d, J=9 Hz, 2H), 7.45 (d, J=9 Hz, 2H). MS ($DCl—NH_3$) m/z 214 (M+H)+.

Example 1B (1S,2S)-[2-(4-Bromophenyl)cyclopropyl]methanol

The title compound was prepared by the method of A. B. Charette and H. Lebel (Organic Synthesis, 1998, 76, 86-96) substituting trans-3-(4-bromophenyl)prop-2-en-1-ol (the product of Example 1A) for 3-phenyl-prop-2-en-1-ol. $^1$H NMR (300 MHz, $CDCl_3$): δ 0.92-1.0 (m, 2H), 1.45-1.48 (m, 2H), 1.76-1.85 (m, 1H), 3.61 (d, J=7.5 Hz, 2H), 6.95 (d, J=9 Hz, 2H), 7.37 (d, J=9 Hz, 2H). MS ($DCl—NH_3$) m/z 228 (M+H)+.

Example 1C (1S,2S)-2-(4-Bromophenyl)cyclopropanecarbaldehyde

DMSO (0.8 mL, 3 equivalents) was added dropwise to a solution of oxalyl chloride (0.48 mL) in anhydrous dichloromethane (50 mL) under $N_2$ at −78° C. A solution of (1S,2S)-[2-(4-bromophenyl)cyclopropyl]methanol (the product from Example 1B, 823 mg) in dichloromethane (20 mL) was then added dropwise at −78° C. Stirring at this temperature was continued for 30 minutes, then triethylamine (2 mL, 4 equivalents) was added, and the dry ice bath was removed. After stirring for 1 hour, the mixture was treated with saturated aqueous $NH_4Cl$. The mixture was extracted with diethyl ether twice. The combined organic extracts were dried ($MgSO_4$) and filtered. The filtrate was concentrated under reduced pressure. The residue was purified by elution through a pad of silica gel with hexane to provide the title compound. $^1$H NMR (300 MHz, $CDCl_3$): δ 1.48 (m, 1H), 1.65 (dt, J=9 Hz, J=6 Hz, 1H), 2.15 (m, 1H), 2.57 (m, 1H), 6.98 (d, J=9 Hz, 2H), 7.45 (d, J=9 Hz, 2H), 9.46 (d, J=4.5 Hz, 1H). MS ($DCl—NH_3$) m/z 226 (M+H)+.

Example 1D

1-[(1S,2S)-2-(4-Bromo-phenyl)-cyclopropylmethyl]-2(S)-methyl-pyrrolidine

A solution of (1S,2S)-2-(4-bromophenyl)cyclopropanecarbaldehyde (the product of Example 1C, 820 mg, 3.64 mmol) and (S)-2-methylpyrrolidine tartaric acid salt (1.12 g, 4.73 mmol) in ethanol (30 mL) was treated with sodium cyanoborohydride (345 mg 5.46 mmol). The mixture was stirred at room temperature for two hours. The mixture was basified to pH=10-12 with NaOH (10%) and partitioned between ethyl acetate and water. The aqueous layer was extracted with ethyl acetate (2×). The combined organic layers were dried ($MgSO_4$) and filtered. The filtrate was concentrated under reduced pressure and the residue was purified on silica gel eluting with 1% to 2% methanol (containing 10% concentrated $NH_4OH$) in dichloromethane to provide the title compound. $^1$H NMR (300 MHz, $CDCl_3$): δ 0.87-0.92(m, 1H), 0.97-1.02 (m, 1H), 1.16 (d, J=6 Hz, 2H), 1.22 (m, 1H), 1.39-1.49 (m, 1H), 1.73-1.81 (m, 3H), 2.0 (m, 2H), 2.36 (q, J=6 Hz, 1H), 2.45 (m, 1H), 3.13 (dd, J=12 Hz, J=6 Hz, 1H), 3.25 (m, 1H), 7.00 (d, J=6 Hz, 2H), 7.37 (d, J=6 Hz, 2H). MS ($DCl—NH_3$) m/z 294 (M+H)+.

(S)-2-methylpyrrolidine and its salts are available commercially from a number of sources including; (S)-2-methylpyrrolidine (Chemical abstracts registry number 59335-84-1) from Sigma-Aldrich Chemical Company, P.O. Box 14508 St. Louis, Mo., 63178 USA, and (S)-2-methylpyrrolidine hydrochloride (Chemical abstracts registry number 174500-74-4) from AstaTech, Inc. Keystone Business Park 2525 Pearl Buck Road Bristol, Pa., 19007 USA. Methods of obtaining (S)-2-methylpyrrolidine by enantioselective recrystallization with tartaric acid have been described for example in Sakurai, et al. Crystal Growth & Design (2006) vol. 6(7) pages 1606-1610. (S)-2-Methylpyrrolidine L-tartaric acid salt (313 grams) was recrystallized from a mixture of 4.8 Liters of ethanol and 1.2 liters of methanol heated at 60° C. and allowed to cool to deposit (S)-2-methylpyrrolidine L-tartaric acid salt.

Example 1E

4'-((1S,2S)-2-{[(2S)-2-Methylpyrrolidin-1-yl]methyl}cyclopropyl)-1,1'-biphenyl-4-carbonitrile To a solution of 1-[(1S,2S)-2-(4-bromo-phenyl)-cyclopropylmethyl]-2(S)-methyl-pyrrolidine (the product of Example 1D, 50 mg, 0.17 mmol) in isopropyl alcohol (4 mL) under an atmosphere of nitrogen was added 4-cyanophenylboronic acid (30 mg, 0.2 mmol), dichlorobis(triphenylphosphine)palladium(II) (6 mg, 8.5 µmol) and potassium carbonate (59 mg, 0.43 mmol). The mixture was heated to 90° C. for 5 hours, cooled to ambient temperature and partitioned between ethyl acetate (25 mL) and $H_2O$ (10 mL). The separated organic layer was washed with brine, dried ($MgSO_4$), filtered, concentrated under reduced pressure and chromatographed on silica gel eluting with 3% methanol (containing 10% concentrated $NH_4OH$) in dichloromethane to provide the title compound. $^1H$ NMR (300 MHz, $CD_3OD$) δ 1.01 (m, 1H), 1.13 (m, 1H), 1.25 (d, J=6 Hz, 3H), 1.36 (m, 1H), 1.54 (m, 1H), 1.89 (m, 3H), 2.11 (m, 1H), 2.30 (m, 1H), 2.65 (m, 1H), 2.79 (m, 1H), 3.27 (dd, J=12 Hz, J=6 Hz, 1H), 3.40 (m, 1H), 7.22 (d, J=9 Hz, 2H), 7.59 (d, J=6 Hz, 2H), 7.78 (s, 4H). MS (DCl—$NH_3$) m/z 317 (M+H)$^+$.

Example 2

4'-((1S,2S)-2-{[(2R)-2-Methylpyrrolidin-1-yl]methyl}cyclopropyl)-1,1'-biphenyl-4-carbonitrile

Example 2A

1-[2-(4-Bromo-phenyl)-(1S,2S)-cyclopropylmethyl]-(2R)-2-methyl-pyrrolidine

The title compound was prepared using the procedure described in Example 1D, substituting (R)-2-methylpyrrolidine for (S)-2-methylpyrrolidine. $^1H$ NMR (300 MHz, $CD_3OD$): δ 0.92(m, 1H), 0.99 (m, 1H), 1.13 (d, J=6 Hz, 3H), 1.24 (m, 1H), 1.43(m, 1H), 1.77(m, 3H), 1.98 (m, 2H), 2.13 (dd, J=12 Hz, J=6 Hz, 1H), 2.30 (q, J=9 Hz, 1H), 2.41 (m, 1H), 2.94 (dd, J=12 Hz, J=6 Hz, 1H), 3.25 (m, 1H), 7.00 (d, J=9 Hz, 2H), 7.36 (d, J=9 Hz, 2H). MS (DCl—$NH_3$) m/z 294 (M+H)$^+$.

(R)-2-methylpyrrolidine and its salts are available commercially from a number of sources, including; (R)-2-methylpyrrolidine (Chemical abstracts registry number 41720-98-3) from Sigma-Aldrich Chemical Company, P.O. Box 14508 St. Louis, Mo., 63178 USA, and (R)-2-methylpyrrolidine hydrochloride (Chemical abstracts registry number 135324-85-5) from AstaTech, Inc. Keystone Business Park 2525 Pearl Buck Road Bristol, Pa., 19007 USA. Methods of obtaining (R)-2-methylpyrrolidine by enantioselective recrystallization with tartaric acid have been described for example in Sakurai, et al. Crystal Growth & Design (2006) vol. 6(7) pages 1606-1610 and in Pu, et al. Organic Process Research & Development 2005, 9, 45-50.

Example 2B

4'-((1S,2S)-2-{[(2R)-2-Methylpyrrolidin-1-yl]methyl}cyclopropyl)-1,1'-biphenyl-4-carbonitrile The title compound was prepared using the procedure described in Example 1E substituting 1-[2-(4-bromo-phenyl)-(1S,2S)-cyclopropylmethyl]-(2R)-2-methyl-pyrrolidine (the product from Example 2A) for 1-[(1S,2S)-2-(4-bromo-phenyl)-cyclopropylmethyl]-2(S)-methyl-pyrrolidine (the product from 1D). $^1H$ NMR (300 MHz, $CD_3OD$): δ 0.92(m, 1H), 0.99 (m, 1H), 1.13 (d, J=6 Hz, 2H), 1.24 (m, 1H), 1.43(m, 1H), 1.77(m, 3H), 1.98 (m, 2H), 2.13 (dd, J=12 Hz, J=6 Hz, 1H), 2.30 (q, J=9 Hz, 1H), 2.41 (m, 1H), 2.94 (dd, J=12 Hz, J=6 Hz, 1H), 3.25 (m, 1H), 7.00 (d, J=9 Hz, 2H), 7.36 (d, J=9 Hz, 2H). MS (DCl—$NH_3$) m/z 294 (M+H)$^+$.

Example 3

4'-((1R,2R)-2-{[(2R)-2-Methylpyrrolidin-1-yl]methyl}cyclopropyl)-1,1'-biphenyl-4-carbonitrile

Example 3A (1R,2R)-[2-(4-Bromophenyl)cyclopropyl]methanol

The title compound was prepared by the method of A. B. Charette and H. Lebel (Organic Synthesis, 1998, 76, 86-96) substituting trans-3-(4-Bromophenyl)prop-2-en-1-ol (the product from Example 1A) for 3-Phenyl-prop-2-en-1-ol. $^1H$ NMR (300 MHz, $CDCl_3$): δ 0.92-1.0 (m, 2H), 1.45-1.48 (m, 2H), 1.76-1.85 (m, 1H), 3.61 (d, J=7.5 Hz, 2H), 6.95 (d, J=9 Hz, 2H), 7.37 (d, J=9 Hz, 2H). MS (DCl—$NH_3$) m/z 228 (M+H)$^+$.

Example 3B (1R,2R)-2-(4-Bromophenyl)cyclopropanecarbaldehyde

DMSO (0.8 mL, 3 equivalents) was added dropwise to a solution of oxalyl chloride (0.48 mL) in an hydrous dichloromethane (50 mL) under $N_2$ at −78° C. A solution of (1R,2R)-[2-(4-bromophenyl)cyclopropyl]methanol (the product of Example 3A, 823 mg) in dichloromethane (20 mL) was then added dropwise at −78° C. Stirring at this temperature was continued for 30 minutes, then triethylamine (2 mL, 4 equivalents) was added and the dry ice bath was removed. After stirring for 1 hour, the mixture was treated with saturated aqueous $NH_4Cl$. The mixture was extracted with diethyl ether. The combined organic extracts were dried ($MgSO_4$) and filtered. The filtrate was concentrated under reduced pressure. The residue was purified by elution through a pad of silica gel with hexane to provide the title compound. $^1H$ NMR (300 MHz, $CDCl_3$): δ 1.48 (m, 1H), 1.65 (dt, J=9 Hz, J=6 Hz, 1H), 2.15 (m, 1H), 2.57 (m, 1H), 6.98 (d, J=9 Hz, 2H), 7.45 (d, J=9 Hz, 2H), 9.46 (d, J=4.5 Hz, 1H). MS (DCl—$NH_3$) m/z 226 (M+H)$^+$.

Example 3C

1-[2-(4-Bromo-phenyl)-(1R,2R)-cyclopropylmethyl]-(2R)-2-methyl-pyrrolidine

A solution of (1R,2R)-2-(4-bromophenyl)cyclopropanecarbaldehyde (the product of Example 3B, 600 mg, 2.67 mmol) and (R)-2-methylpyrrolidine tartaric acid salt (0.82 g, 3.47 mmol) in ethanol (30 mL) was treated with sodium cyanoborohydride (252 mg 4 mmol). The mixture was stirred at room temperature for two hours. The mixture was quenched with HCl (1N) and then basified to pH=10-12 with NaOH (10%) and partitioned between ethyl acetate and water. The aqueous layer was extracted with ethyl acetate. The combined organic layers were dried ($MgSO_4$) and filtered. The filtrate was concentrated under reduced pressure and the residue was purified on silica gel with 1% to 2% methanol (containing 10% concentrated NH₄OH) in dichloromethane to provide the title compound. ¹H NMR (300 MHz, CD₃OD): δ 0.89 (m, 1H), 0.98 (m, 1H), 1.14 (d, J=6 Hz, 2H), 1.19 (m, 1H), 1.43 (m, 1H), 1.75 (m, 3H), 1.95 (m, 2H), 2.30 (q, J=9 Hz, 1H), 2.37 (m, 1H), 3.14 (dd, J=12 Hz, J=6 Hz, 1H), 3.22 (m, 1H), 7.00 (d, J=9 Hz, 2H), 7.36 (d, J=9 Hz, 2H). MS (DCl—NH₃) m/z 294 (M+H)⁺.

Example 3D

4'-((1R,2R)-2-{[(2R)-2-Methylpyrrolidin-1-yl]methyl}cyclopropyl)-1,1'-biphenyl-4-carbonitrile To a solution of 1-[2-(4-bromo-phenyl)-(1R,2R)-cyclopropylmethyl]-(2R)-2-methylpyrrolidine (product of Example 3C, 50 mg, 0.17 mmol) in isopropyl alcohol (4 mL) under an atmosphere of nitrogen was added 4-cyanophenylboronic acid (30 mg, 0.2 mmol), dichlorobis(triphenylphosphine)palladium(II) (6 mg, 8.5 μmol) and potassium carbonate (59 mg, 0.43 mmol). The mixture was heated to 90° C. for 5 hours, cooled to ambient temperature and partitioned between ethyl acetate (25 mL) and H₂O (10 mL). The organic extraction was washed with brine, dried (MgSO₄), filtered, concentrated under reduced pressure and chromatographed on silica gel eluting with methanol (containing 10% concentrated NH₄OH) in dichloromethane to provide the title compound. ¹H NMR (300 MHz, CD₃OD) δ 1.08 (m, 1H), 1.19 (m, 1H), 1.32 (d, J=6 Hz, 3H), 1.42 (m, 1H), 1.63 (m, 1H), 1.99 (m, 3H), 2.20 (m, 1H), 2.65 (m, 1H), 2.94 (m, 1H), 3.07 (m, 1H), 3.34 (dd, J=9 Hz, J=6 Hz, 1H), 3.51 (m, 1H), 7.24 (d, J=9 Hz, 2H), 7.60 (d, J=6 Hz, 2H), 7.78 (s, 4H). MS (DCl—NH₃) m/z 317 (M+H)⁺.

Example 4

4'-((1R,2R)-2-{[(2S)-2-Methylpyrrolidin-1-yl]methyl}cyclopropyl)-1,1'-biphenyl-4-carbonitrile Example 4A 1-[2-(4-Bromo-phenyl)-(1R,2R)-cyclopropylmethyl]-(2S)-2-methyl-pyrrolidine The title compound was prepared using the procedure described in Example 3C substituting (S)-2-methylpyrrolidine tartaric acid salt for (R)-2-methylpyrrolidine tartaric acid salt. ¹H NMR (300 MHz, CD₃OD): δ 0.93 (m, 1H), 0.99 (m, 1H), 1.13 (d, J=6 Hz, 3H), 1.24 (m, 1H), 1.44 (m, 1H), 1.76 (m, 3H), 1.98 (m, 1H), 2.14 (dd, J=12 Hz, J=6 Hz, 1H), 2.32 (q, J=9 Hz, 1H), 2.43 (m, 1H), 2.94 (dd, J=12 Hz, J=6 Hz, 1H), 3.26 (m, 1H), 7.00 (d, J=9 Hz, 2H), 7.36 (d, J=9 Hz, 2H). MS (DCl—NH₃) m/z 294 (M+H)⁺.

Example 4B

4'-((1R,2R)-2-{[(2S)-2-Methylpyrrolidin-1-yl]methyl}cyclopropyl)-1,1'-biphenyl-4-carbonitrile The title compound was prepared using the procedure described in Example 3D substituting 1-[2-(4-bromo-phenyl)-(1R,2R)-cyclopropylmethyl]-(2S)-2-methyl-pyrrolidine (the product from Example 4A) for 1-[2-(4-bromo-phenyl)-(1R,2R)-cyclopropylmethyl]-(2R)-2-methyl-pyrrolidine (the product from Example 3C). ¹H NMR (300 MHz, CD₃OD) δ 1.22 (m, 2H), 1.42 (d, J=6 Hz, 3H), 1.53 (m, 1H), 1.76 (m, 1H), 2.08 (m, 3H), 2.31 (m, 1H), 3.09 (dd, J=12 Hz, J=6 Hz, 1H), 3.23 (m, 1H), 3.39 (dd, J=12 Hz, J=6 Hz, 1H), 3.50 (m, 1H), 3.67 (m, 1H), 7.27 (d, J=9 Hz, 2H), 7.61 (d, J=6 Hz, 2H), 7.78 (s, 4H). MS (DCl—NH₃) m/z 317 (M+H)⁺.

Example 5

4'-{(1S,2S)-2-[(2-Methylpyrrolidin-1-yl)methyl]cyclopropyl}-1,1'-biphenyl-4-carbonitrile Example 5A 1-[2-(4-Bromo-phenyl)-(1S,2S)-cyclopropylmethyl]-2-methyl-pyrrolidine The title compound was prepared using the procedure described in Example 1D substituting racemic 2-methylpyrrolidine for (S)-2-methylpyrrolidine. ¹H NMR (300 MHz, CDCl₃): δ 0.87-0.92 (m, 1H), 0.97-1.02 (m, 1H), 1.16 (d, J=6 Hz, 2H), 1.22 (m, 1H), 1.39-1.49 (m, 1H), 1.73-1.81 (m, 3H), 2.0 (m, 2H), 2.36 (q, J=6 Hz, 1H), 2.45 (m, 1H), 3.13 (dd, J=12 Hz, J=6 Hz, 1H), 3.25 (m, 1H), 7.00 (d, J=6 Hz, 2H), 7.37 (d, J=6 Hz, 2H). MS (DCl—NH₃) m/z 294 (M+H)⁺.

Example 5B

4'-{(1S,2S)-2-[(2-Methylpyrrolidin-1-yl)methyl]cyclopropyl}-1,1'-biphenyl-4-carbonitrile The title compound was prepared using the procedure described in Example 1E substituting 1-[2-(4-bromo-phenyl)-(1S,2S)-cyclopropylmethyl]-2-methyl-pyrrolidine (the product from Example 5A) for 1-[(1S,2S)-2-(4-bromo-phenyl)-cyclopropylmethyl]-2(S)-methyl-pyrrolidine (the product from Example 1D). ¹H NMR (300 MHz, CD₃OD) δ 0.98 (m, 1H), 1.1 (m, 1H), 1.20 (d, J=6 Hz, 2H), 1.34 (m, 1H), 1.49 (m, 1H), 1.84 (m, 3H), 2.06 (m, 2H), 2.51 (m, 1H), 2.61 (m, 1H), 3.06 (dd, J=12 Hz, J=6 Hz, 0.5H), 3.22 (dd, J=12 Hz, J=6 Hz, 0.5H), 3.34 (m, 1H), 7.22 (dd, J=12 Hz, J=6 Hz, 2H), 7.59 (d, J=9 Hz, 2H), 7.77 (s, 4H). MS (DCl—NH₃) m/z 317 (M+H)⁺.

Example 6

5-[4-((1S,2S)-2-{[(2S)-2-Methylpyrrolidin-1-yl]methyl}cyclopropyl)phenyl]pyrimidine The title compound was prepared using the procedure described in Example 1E substituting 5-pyrimidineboronic acid for 4-cyanophenylboronic acid. ¹H NMR (300 MHz, CD₃OD) δ 0.96 (m, 1H), 1.09 (m, 1H), 1.16 (d, J=6 Hz, 3H), 1.31 (m, 1H), 1.44 (m, 1H), 1.76 (m, 2H), 1.86 (m, 1H), 1.99 (m, 2H), 2.35 (m, 1H), 2.41 (m, 1H), 3.29 (dd, J=12 Hz, J=6 Hz, 1H), 3.58 (m, 1H), 7.26 (dd, J=12 Hz, J=6 Hz, 2H), 7.60 (d, J=9 Hz, 2H), 7.77 (s, 4H). MS (DCl—NH₃) m/z 317 (M+H)⁺.

Example 7

2-Methoxy-5-[4-((1S,2S)-2-{[(2S)-2-methylpyrrolidin-1-yl]methyl}cyclopropyl)phenyl]pyrimidine The title compound was prepared using the procedure described in Example 1E substituting 2-methoxy-5-pyrimidineboronic acid for 4-cyanophenylboronic acid. ¹H NMR (300 MHz, CD₃OD) δ 0.94 (m, 1H), 1.05 (m, 1H), 1.15 (d, J=6 Hz, 3H), 1.26 (m, 1H), 1.43 (m, 1H), 1.77 (m, 3H), 1.94

(m, 2H), 2.32 (m, 2H), 3.21 (m, 2H), 4.04 (s, 1H), 7.21 (d, J=9 Hz, 2H), 7.52 (d, J=9 Hz, 2H), 8.78 (s, 2H). MS (DCl—NH$_3$) m/z 324 (M+H)$^+$.

Example 8

2,6-Dimethyl-3-[4-((1S,2S)-2-{[(2R)-2-methylpyrrolidin-1-yl]methyl}cyclopropyl)phenyl]pyridine The title compound was prepared using the procedure described in Example 2B substituting 2,6-dimethyl-3-(4,4,5,5-tetramethyl-[1,3,2]dioxaborolan-2-yl)-pyridine (prepared according to the procedure described in J. Org. Chem. 67:7541-7543 (2002)) for 4-cyanophenylboronic acid. $^1$H NMR (300 MHz, CD$_3$OD) δ 0.95 (m, 1H), 1.06 (m, 1H), 1.16 (d, J=6 Hz, 3H), 1.33 (m, 1H), 1.47 (m, 1H), 1.80(m, 3H), 2.00(m, 1H), 2.20 (dd, J=12 Hz, J=6 Hz, 1H), 2.37(m, 2H), 2.41 (s, 3H), 2.48 (m, 1H), 2.52 (s, 3H), 3.0 (dd, J=12 Hz, J=6 Hz, 1H), 7.19 (m, 5H), 7.51 (d, J=9 Hz, 1H). MS (DCl—NH$_3$) m/z 321 (M+H)$^+$.

Example 9

2-Methoxy-5-[4-((1S,2S)-2-{[(2R)-2-methylpyrrolidin-1-yl]methyl}cyclopropyl)phenyl]pyridine The title compound was prepared using the procedure described in Example 2B substituting 2-methoxy-5-pyridineboronic acid for 4-cyanophenylboronic acid. $^1$H NMR (300 MHz, CD$_3$OD) δ 1.21 (m, 2H), 1.45 (d, J=6 Hz, 3H), 1.50 (m, 1H), 1.76 (m, 1H), 2.00(m, 3H), 2.34(m, 1H), 3.14 (dd, J=12 Hz, J=6 Hz, 1H), 3.27(m, 1H), 3.44 (dd, J=12 Hz, J=6 Hz, 1H), 3.54 (m, 1H), 3.73(m, 1H), 3.95 (s, 3H), 6.88 (d, J=9 Hz, 1H), 7.21 (d, J=9 Hz, 2H), 7.51 (d, J=9 Hz, 2H), 7.93 (dd, J=12 Hz, J=6 Hz, 1H), 8.33 (d, J=3 Hz, 1H). MS (DCl—NH$_3$) m/z 323 (M+H)$^+$.

Example 10

5-[4-((1S,2S)-2-{[(2R)-2-Methylpyrrolidin-1-yl]methyl}cyclopropyl)phenyl]pyrimidine The title compound was prepared using the procedure described in Example 2B substituting 5-pyrimidineboronic acid for 4-cyanophenylboronic acid. $^1$H NMR (300 MHz, CD$_3$OD) δ 1.26 (m, 2H), 1.45 (d, J=6 Hz, 3H), 1.56 (m, 1H), 1.76 (m, 1H), 2.09(m, 3H), 2.35 (m, 1H), 3.12 (dd, J=12 Hz, J=6 Hz, 1H), 3.26 (m, 1H), 3.46 (dd, J=12 Hz, J=6 Hz, 1H), 3.55 (m, 1H), 3.73 (m, 1H), 7.32 (d, J=9 Hz, 2H), 7.66 (d, J=9 Hz, 2H), 9.04 (s, 2H), 9.12 (s, 1H). MS (DCl—NH$_3$) m/z 317 (M+H)$^+$.

Example 11

5-[4-((1R,2R)-2-{[(2S)-2-Methylpyrrolidin-1-yl]methyl}cyclopropyl)phenyl]pyrimidine The title compound was prepared using the procedure described in Example 4B substituting 5-pyrimidineboronic acid for 4-cyanophenylboronic acid. $^1$H NMR (300 MHz, CD$_3$OD) δ 1.09 (m, 1H), 1.17 (m, 1H), 1.29 (d, J=6 Hz, 3H), 1.45 (m, 1H), 1.61 (m, 1H), 1.95 (m, 3H), 2.16 (m, 1H), 2.66 (dd, J=12 Hz, J=6 Hz, 1H), 2.79 (q, J=9 Hz, 1H), 2.99 (m, 1H), 3.20 (dd, J=12 Hz, J=6 Hz, 1H), 3.49 (m, 1H), 7.29 (d, J=9 Hz, 2H), 7.63 (d, J=9 Hz, 2H), 9.03 (s, 2H), 9.10 (s, 1H). MS (DCl—NH$_3$) m/z 317 (M+H)$^+$.

Example 12

5-[4-((1R,2R)-2-{[(2R)-2-Methylpyrrolidin-1-yl]methyl}cyclopropyl)phenyl]pyrimidine The title compound was prepared using the procedure described in Example 3D substituting 5-pyrimidineboronic acid for 4-cyanophenylboronic acid. $^1$H NMR (300 MHz, CD$_3$OD) δ 1.00 (m, 1H), 1.11 (m, 1H), 1.21 (d, J=6 Hz, 3H), 1.34 (m, 1H), 1.51 (m, 1H), 1.82(m, 2H), 1.90(m, 1H), 2.08 (m, 1H), 2.18(m, 1H), 2.53 (q, J=9 Hz, 1H), 2.62 (m, 1H), 3.23 (dd, J=12 Hz, J=6 Hz, 1H), 3.34 (m, 1H), 7.27 (d, J=9 Hz, 2H), 7.62 (d, J=9 Hz, 2H), 9.03 (s, 2H), 9.10 (s, 1H). MS (DCl—NH$_3$) m/z 317 (M+H)$^+$.

Example 13

2,4-Dimethoxy-5-[4-((1R,2R)-2-{[(2S)-2-methylpyrrolidin-1-yl]methyl}cyclopropyl)phenyl]pyrimidine The title compound was prepared using the procedure described in Example 4B substituting 2,6-dimethoxy-5-pyrimidineboronic acid for 4-cyanophenylboronic acid. $^1$H NMR (300 MHz, CD$_3$OD) δ 1.03 (m, 1H), 1.11 (m, 1H), 1.27 (d, J=6 Hz, 3H), 1.39 (m, 1H), 1.59 (m, 1H), 1.93(m, 3H), 2.15 (m, 1H), 2.58 (dd, J=12 Hz, J=6 Hz, 1H), 2.73 (q, J=9 Hz, 1H), 2.91 (m, 1H), 3.15 (dd, J=12 Hz, J=6 Hz, 1H), 3.45 (m, 1H), 4.03 (s, 6H), 7.16 (d, J=9 Hz, 2H), 7.40 (d, J=9 Hz, 2H), 8.22 (s, 1H). MS (DCl—NH$_3$) m/z 354 (M+H)$^+$.

Example 14

2,4-Dimethoxy-5-[4-((1R,2R)-2-{[(2R)-2-methylpyrrolidin-1-yl]methyl}cyclopropyl)phenyl]pyrimidine The title compound was prepared using the procedure described in Example 3D substituting 2,6-dimethoxy-5-pyrimidineboronic acid for 4-cyanophenylboronic acid. $^1$H NMR (300 MHz, CD$_3$OD) δ 1.04 (m, 1H), 1.15 (m, 1H), 1.31 (d, J=6 Hz, 3H), 1.38 (m, 1H), 1.62 (m, 1H), 1.97(m, 3H), 2.18 (m, 1H), 2.57 (dd, J=12 Hz, J=6 Hz, 1H), 2.87 (q, J=9 Hz, 1H), 3.02 (m, 1H), 3.34 (dd, J=12 Hz, J=6 Hz, 1H), 3.50 (m, 1H), 4.03 (s, 6H), 7.16 (d, J=9 Hz, 2H), 7.41 (d, J=9 Hz, 2H), 8.22 (s, 1H). MS (DCl—NH$_3$) m/z 354 (M+H)$^+$.

Example 15

2,4-Dimethoxy-5-[4-((1S,2S)-2-{[(2R)-2-methylpyrrolidin-1-yl]methyl}cyclopropyl)phenyl]pyrimidine The title compound was prepared using the procedure described in Example 2B substituting 2,6-dimethoxy-5-pyrimidineboronic acid for 4-cyanophenylboronic acid. $^1$H NMR (300 MHz, CD$_3$OD) δ 1.04 (m, 1H), 1.12 (m, 1H), 1.28 (d, J=6 Hz, 3H), 1.39 (m, 1H), 1.60 (m, 1H), 1.94(m, 3H), 2.15 (m, 1H), 2.65 (dd, J=12 Hz, J=6 Hz, 1H), 2.78 (q, J=9 Hz, 1H), 2.98 (m, 1H), 3.17 (dd, J=12 Hz, J=6 Hz, 1H), 3.47 (m, 1H), 4.03 (s, 6H), 7.17 (d, J=9 Hz, 2H), 7.41 (d, J=9 Hz, 2H), 8.22 (s, 1H). MS (DCl—NH$_3$) m/z 354 (M+H)$^+$.

Example 16

2,4-Dimethoxy-5-[4-((1S,2S)-2-{[(2S)-2-methylpyrrolidin-1-yl]methyl}cyclopropyl)phenyl]pyrimidine The title compound was prepared using the procedure described in Example 1E substituting 2,6-dimethoxy-5-pyrimidineboronic acid for 4-cyanophenylboronic acid. $^1$H NMR (300 MHz, CD$_3$OD) δ 1.04 (m, 1H), 1.12 (m, 1H), 1.28 (d, J=6 Hz, 3H), 1.39 (m, 1H), 1.60 (m, 1H), 1.94 (m, 3H), 2.15 (m, 1H), 2.65 (dd, J=12 Hz, J=6 Hz, 1H), 2.78 (q, J=9 Hz, 1H), 2.98 (m, 1H), 3.17 (dd, J=12 Hz, J=6 Hz, 1H), 3.47 (m, 1H), 4.03 (s, 6H), 7.17 (d, J=9 Hz, 2H), 7.41 (d, J=9 Hz, 2H), 8.22 (s, 1H). MS (DCl—NH$_3$) m/z 354 (M+H)$^+$.

Example 17

2-[4-((1R,2R)-2-{[(2S)-2-Methylpyrrolidin-1-yl]methyl}cyclopropyl)phenyl]pyridazin-3(2H)-one A solution of the product from Example 4A (47 mg, 0.16 mmol; 1-[2-(4-bromophenyl)-(1R,2R)-cyclopropylmethyl]-(2S)-2-methyl-pyrrolidine), 3(2H)-pyridazinone (CAS # 504-30-3, 20 mg, 0.2 mmol), copper iodide (1.5 mg, 0.008 mmol), N,N'-trans-dimethyl-cyclohexane-1,2-diamine (2.3 mg, 0.016 mmol) and potassium phosphate (75 mg, 0.35 mmol) in a mixture of toluene and isopropanol (4 ml, 1:1) was heated to 110° C. in a screw capped vial for 16 hours. The mixture was cooled to ambient temperature, treated with H$_2$O and extracted with ethyl acetate (2×25 mL). The organic layer was separated, washed with brine and dried with magnesium sulfate. After filtration, the organic layer was concentrated under reduced pressure and the resulting oil was purified on silica gel with 1% to 3% methanol (containing 10% concentrated NH$_4$OH) in dichloromethane to provide the title compound. $^1$H NMR (300 MHz, CD$_3$OD) δ 1.07 (m, 1H), 1.14 (m, 1H), 1.26 (d, J=6 Hz, 3H), 1.40 (m, 1H), 1.58 (m, 1H), 1.90 (m, 3H), 2.13 (m, 1H), 2.58 (m, 1H), 2.70 (q, J=9 Hz, 1H), 2.89 (m, 1H), 3.14 (dd, J=12 Hz, J=6 Hz, 1H), 3.44 (m, 1H), 7.07 (d, J=9 Hz, 1H), 7.24 (d, J=9 Hz, 2H), 7.44 (d, J=9 Hz, 2H), 7.47 (m, 1H), 8.03 (m, 1H). MS (DCl—NH$_3$) m/z 310 (M+H)$^+$.

Example 18

2-[4-((1S,2S)-2-{[(2S)-2-Methylpyrrolidin-1-yl]methyl}cyclopropyl)phenyl]pyridazin-3(2H)-one The title compound was prepared using the procedure described in Example 17 substituting the product from Example 1D 1-[(1S,2S)-2-(4-bromo-phenyl)-cyclopropylmethyl]-2(S)-methyl-pyrrolidine as starting material in place of the 1-[2-(4-Bromo-phenyl)-(1R,2R)-cyclopropylmethyl]-(2S)-2-methyl-pyrrolidine. $^1$H NMR (300 MHz, CD$_3$OD) δ 0.97 (m, 1H), 1.13 (m, 1H), 1.23 (d, J=6 Hz, 3H), 1.34 (m, 1H), 1.51 (m, 1H), 1.85 (m, 3H), 1.93 (m, 1H), 2.01 (m, 1H), 2.68 (q, J=9 Hz, 1H), 2.85 (m, 1H), 3.08 (m, 1H), 3.23 (m, 1H), 7.07 (d, J=9 Hz, 1H), 7.22 (d, J=9 Hz, 2H), 7.44 (d, J=9 Hz, 2H), 7.47 (m, 1H), 8.03 (m, 1H). MS (DCl—NH$_3$) m/z 310 (M+H)$^+$.

Example 18A

2-[4-((1S,2S)-2-{[(2S)-2-Methylpyrrolidin-1-yl]methyl}cyclopropyl)phenyl]pyridazin-3(2H)-one L-bitartrate monohydrate Example 18 freebase (9.9 g in 270 mL 2-propanol) was combined with L-tartaric acid (4.8 g in 30 mL water) in a round-bottom flask. This suspension was heated to about 70° C. A solution was obtained while heating. The solution was then slowly cooled to 10° C. Crystallization was observed upon cooling. Crystals were collected and analyzed by PXRD, which indicated that the solid was of crystalline 2-[4-((1S,2S)-2-{[(2S)-2-Methylpyrrolidin-1-yl]methyl}cyclopropyl)phenyl]pyridazin-3(2H)-one L-bitartrate monohydrate (FIG. 1).

Example 18B

Figure 2:
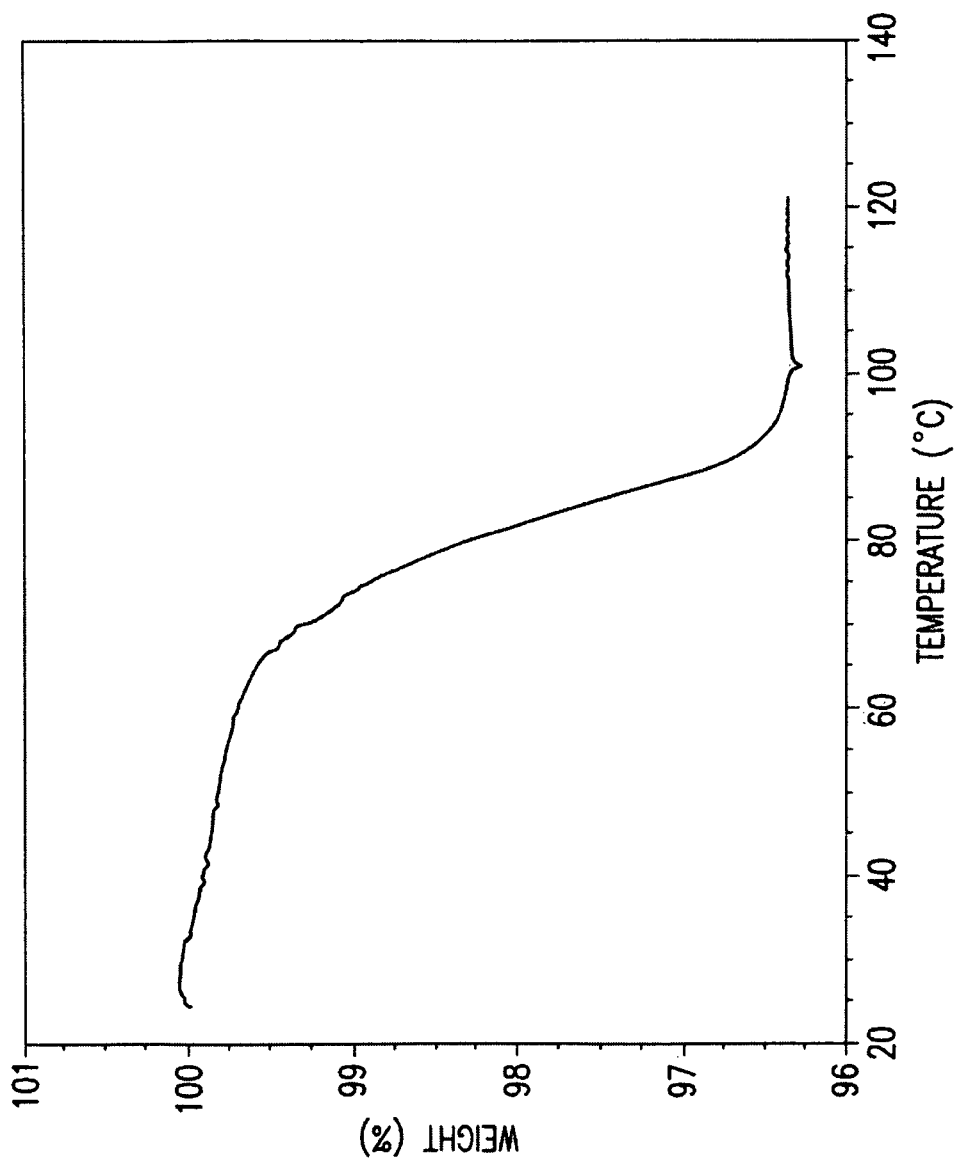
FIG. 2 is a thermogram of 2-{4-[(1S,2S)-2-((S)-2-Methyl-pyrrolidin-1-ylmethyl)-cyclopropyl]-phenyl}-2H-pyridazin-3-one L-bitartrate monohydrate obtained by thermal gravimetric analysis (TGA).

2-[4-((1S,2S)-2-{[(2S)-2-Methylpyrrolidin-1-yl]methyl}cyclopropyl)phenyl]pyridazin-3(2H)-one L-bitartrate monohydrate Example 18 freebase (2.50 g) and L-tartaric acid (1.34 g) solids were added to a solvent mixture consisting of 2-propanol and water at 9/1 volume ratio (50 mL). This suspension was heated to about 65° C. A clear solution was obtained while heating. The solution was then slowly cooled to 20° C. over a time not longer than 16 hours. Crystallization was observed upon cooling. Crystals were harvested by filtration. The filtrate was washed three times with 10 mL of solvent mixture (90:10 2-propanol:water v/v). Drying was achieved at 55° C. in a vacuum oven overnight. The crystals were analyzed by PXRD, which indicated that the solid was of crystalline 2-[4-((1S,2S)-2-{[(2S)-2-Methylpyrrolidin-1-yl]methyl}cyclopropyl)phenyl]pyridazin-3(2H)-one L-bitartrate monohydrate (FIG. 1). The solid was also analyzed by thermal gravimetric analysis and was found to have a weight loss. (FIG. 2)

Example 18C

2-[4-((1S,2S)-2-{[(2S)-2-Methylpyrrolidin-1-yl]methyl}cyclopropyl)phenyl]pyridazin-3(2H)-one L-bitartrate anhydrate Example 18 freebase (0.99 g in 10 mL 200 proof ethanol) was combined with L-tartaric acid (0.48 g in 20 mL 2-propanol) in a 50 mL roundbottom flask. The suspension was stirred and heated to 70° C. to obtain a clear solution. The solution was then slowly cooled to room temperature. Crystallization was observed upon cooling. The crystals were collected and dried at 50° C. in a vacuum oven. The solid was analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one L-bitartrate anhydrate (FIG. 3).

Example 18D

2-[4-((1S,2S)-2-{[(2S)-2-Methylpyrrolidin-1-yl]methyl}cyclopropyl)phenyl]pyridazin-3(2H)-one L-bitartrate anhydrate Example 18 freebase (148 mg) was dissolved in 0.2 mL 200 proof ethanol at 50° C. with stirring. L-tartaric acid (73.5 mg) was dissolved in 0.6 mL 200 proof ethanol at 50° C. with stirring. The L-tartaric acid solution was then added dropwise to the freebase solution at 50° C. with stirring. After the addition of L-tartartic acid solution, the combined solution was allowed to slowly cool to ambient temperatures. Crystallization was observed upon cooling. The solid was collected and dried at 50° C. in a vacuum oven. The solid was analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one L-bitartrate anhydrate (FIG. 3).

Example 18E

Figure 5:
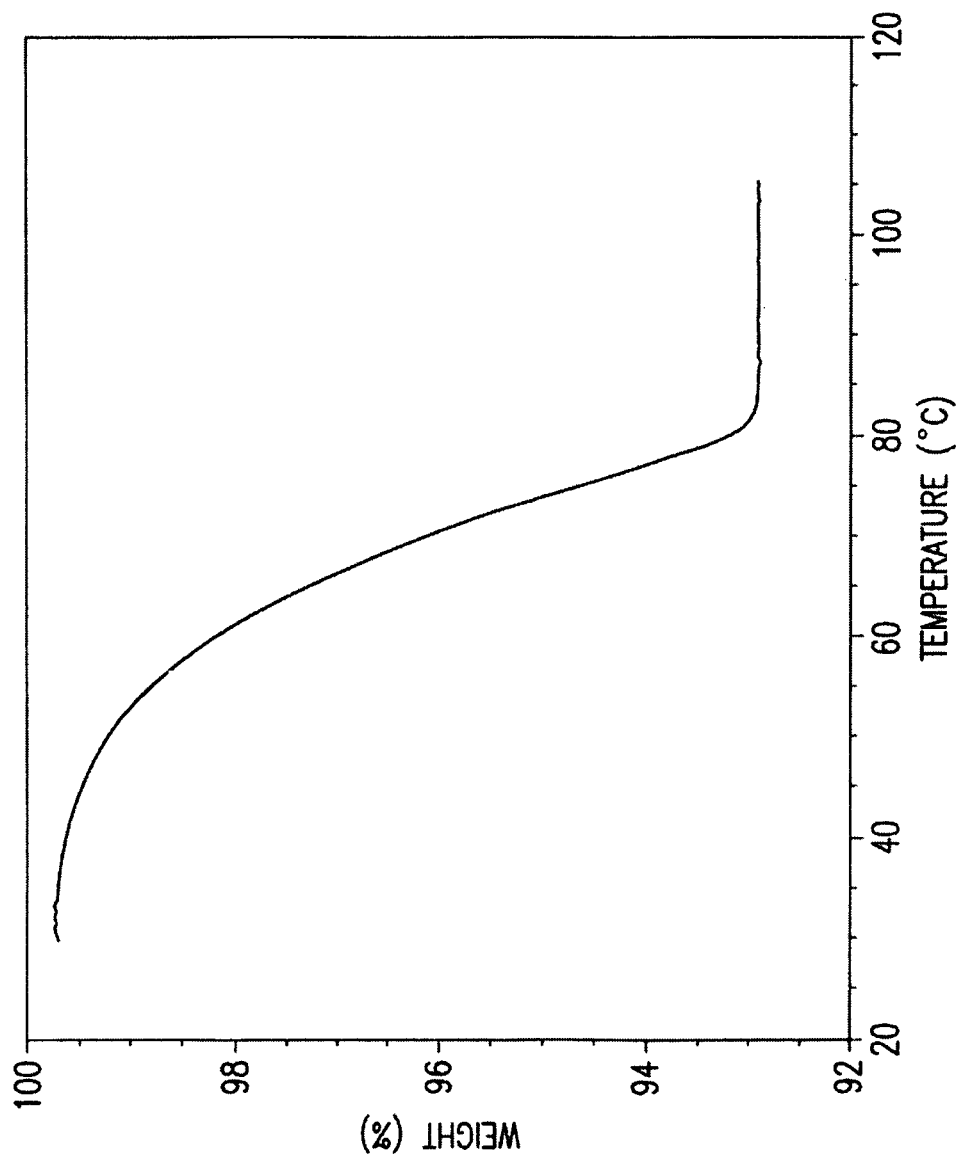
FIG. 5 is a thermogram of 2-{4-[(1S,2S)-2-((S)-2-Methyl-pyrrolidin-1-ylmethyl)-cyclopropyl]-phenyl}-2H-pyridazin-3-one D-bitartrate dihydrate obtained by thermal gravimetric analysis (TGA).

2-[4-((1S,2S)-2-{[(2S)-2-Methylpyrrolidin-1-yl] methyl}cyclopropyl)phenyl]pyridazin-3(2H)-one D-bitartrate dihydrate Example 18 freebase (250 mg) was dissolved in 1.0 mL 2-propanol. D-tartaric acid (124 mg) was dissolved in 2.0 mL 2-propanol. The acid and base solutions were mixed together while stirring. Precipitation was observed upon mixing the two solutions. Water (0.15 mL) was then added to the suspension. The suspension was heated to about 50° C., and was then slowly cooled to ambient temperatures. The solid was collected and analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one_D-bitartrate dihydrate (FIG. 4). The solid was also analyzed by thermal gravimetric analysis and was found to have a weight loss (FIG. 5).

Example 18F

2-[4-((1S,2S)-2-{[2S]-2-Methylpyrrolidin-1-yl] methyl}cyclopropyl)phenyl]pyridazin-3(2H)-one D-bitartrate dihydrate Example 18 freebase (250 mg) was dissolved in 0.5 mL 2-propanol. D-tartaric acid (129 mg) was suspended in 1.0 mL 2-propanol. The base solution was added to the acid suspension at 50° C. with stirring. Water (0.2 mL) was added to the suspension as well. The suspension was then cooled to −15° C. for about one hour. The solid was collected and analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one_D-bitartrate dihydrate (FIG. 4).

Example 18G

2-[4-((1S,2S)-2-{[(2S)-2-Methylpyrrolidin-1-yl] methyl}cyclopropyl)phenyl]pyridazin-3(2H)-one D-bitartrate dihydrate Example 18 freebase (2.5 g) was dissolved in 10.0 mL 2-propanol. D-tartaric acid (1.34 g) was dissolved in 5.0 mL water. The acid and base solutions were combined and heated to 65° C. resulting in a clear solution. 2-propanol (35.0 mL) was added to the solution. Solution was then cooled to 38° C. over about three hours. Additional 2-propanol (35.0 mL) was added during the cooling. Seeds of 2-[4-((1S,2S)-2-{[(2S)-2-Methylpyrrolidin-1-yl]methyl}cyclopropyl)phenyl]pyridazin-3(2H)-one D-bitartrate dihydrate were added and the temperature was held at 38° C. for three hours, during which crystal growth was observed. The suspension was then cooled to 15° C. over about ten hours. The crystals were collected by filtration and the filtrate was washed three times with 15 mL 2-propanol. The solid was analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one_D-bitartrate dihydrate (FIG. 4).

Example 18H

2-[4-((1S,2S)-2-{[(2S)-2-Methylpyrrolidin-1-yl] methyl}cyclopropyl)phenyl]pyridazin-3(2H)-one D-bitartrate anhydrate Crystalline 2-[4-((1S,2S)-2-{[(2S)-2-Methylpyrrolidin-1-yl]methyl}cyclopropyl)phenyl]pyridazin-3(2M)-one_D-bitartrate anhydrate was prepared by dehydrating the title compound D-bitartrate dihydrate, for instance at 55° C. in a vacuum oven. The solid was analyzed by PXRD, which indicated the solid was of crystalline 2-[4-((1S,2S)-2-{[(2S)-2-Methylpyrrolidin-1-yl]methyl}cyclopropyl)phenyl]pyridazin-3(2H)-one D-bitartrate anhydrate (FIG. 6).

Example 19

N-[4-((1S,2S)-2-{[(2S)-2-methylpyrrolidin-1-yl] methyl}cyclopropyl)phenyl]-1H-1,2,4-triazole-3-carboxamide The title compound was prepared using the procedure described in Example 34G substituting 1H-1,2,4-triazole-3-carboxamide for pyridazin-3(2H)-one. $^1$H NMR (300 MHz, CD$_3$OD) δ 1.11-1.18 (m, 1H), 1.22-1.28 (m, 1H), 1.38 (d, J=6 Hz, 3H), 1.47-1.53 (m, 1H), 1.67-1.74 (m, 1H), 2.01-2.15 (m, 3H), 2.24-2.35 (m, 1H), 2.91-2.99 (m, 1H), 3.13-3.23 (m, 1H), 3.33-3.43 (m, 2H), 3.60-3.68 (m, 1H), 7.34 (d, J=9 Hz, 2H), 7.79 (d, J=9 Hz, 2H), 9.05 (s, 1H). MS (DCl—NH$_3$) m/z 326 (M+H)$^+$.

Example 20

2-Methyl-5-[4-((1S,2S)-2-{[(2S)-2-methylpyrrolidin-1-yl]methyl}cyclopropyl)phenyl]-1,3-benzothiazole

Example 20A

2-Methyl-5-(4,4,5,5-tetramethyl-[1,3,2]dioxaborolan-2-yl)-benzothiazole

A solution of 5-bromo-2-methyl-benzothiazole (2 g, 8.8 mmol), 4,4,4',4',5,5,5',5'-octamethyl-2,2'-bi(1,3,2-dioxaborolane) (2.7 g, 10.6 mmol; CAS 73183-34-3), potassium acetate (3.1 g, 31.7 mmol) and Pd(dppf)$_2$Cl$_2$ dichloromethane complex (1:1) (360 mg, 0.51 mmol) in anhydrous tetrahydrofuran (70 mL) under a nitrogen atmosphere was heated to reflux overnight. After cooling to ambient temperature, the mixture was filtered through diatomaceous earth and washed with ethyl acetate. The filtrate was washed with water and brine, dried (MgSO$_4$), filtered and concentrated under reduced pressure. The residue was chromatographed on silica gel eluting with 10% ethyl acetate in hexanes to provide the title compound. $^1$H NMR (300 MHz, CD$_3$Cl$_3$) δ 1.37 (s, 12 H), 2.84 (s, 3 H), 7.75 (d, J=9 Hz, 1 H), 7.82 (d, J=9 Hz, 1 H), 8.38 (s, 1 H); (DCl/NH$_3$) m/z 276 (M+H)$^+$.

Example 20B

2-Methyl-5-[4-((1S,2S)-2-{[(2S)-2-methylpyrrolidin-1-yl]methyl}cyclopropyl)phenyl]-1,3-benzothiazole The title compound was prepared using the procedure described in Example 1E substituting the product from Example 20A for 4-cyanophenylboronic acid. $^1$H NMR (300 MHz, CD$_3$OD) δ 1.01 (m, 1H), 1.14 (m, 1H), 1.26 (d, J=6 Hz, 3H), 1.35 (m, 1H), 1.55 (m, 1H), 1.91(m, 3H), 2.12(m, 1H), 2.34 (m, 1H), 2.67 (m, 1H), 2.75 (m, 1H), 2.85 (s, 3H), 3.26 (m, 2H), 3.41 (m, 1H), 7.21 (d, J=9 Hz, 2H), 7.60 (d, J=9 Hz, 2H), 7.65 (dd, J=9 Hz, J=3 Hz, 1H), 7.96 (d, J=6 Hz, 1H), 8.06 (d, J=3 Hz, 1H). MS (DCl—NH$_3$) m/z 362 (M+H)$^+$.

Example 21

1,3,5-Trimethyl-4-[4-((1S,2S)-2-{[(2S)-2-methylpyrrolidin-1-yl]methyl}cyclopropyl)phenyl]-1H-pyrazole The title compound was prepared using the procedure described in Example 1E substituting 1,3,5-trimethyl-4-(4,4,5,5-tetramethyl-[1,3,2]dioxaborolan-2-yl)-1H-pyrazole (CAS # 844891-04-9) for 4-cyanophenylboronic acid. $^1$H NMR (300 MHz, CD$_3$OD) δ 0.99 (m, 1H), 1.07 (m, 1H), 1.22 (d, J=6 Hz, 3H), 1.29 (m, 1H), 1.51 (m, 1H), 1.86 (m, 3H), 2.08 (m, 1H), 2.15 (s, 3H), 2.18 (m, 1H), 2.21 (s, 3H), 2.56 (m, 1H), 2.65 (m, 1H), 3.24 (m, 1H), 3.38 (m, 1H), 7.14 (s, 4H). MS (DCl—NH$_3$) m/z 324 (M+H)$^+$.

Example 22

2,6-Dimethyl-3-[4-((1S,2S)-2-{[(2S)-2-methylpyrrolidin-1-yl]methyl}cyclopropyl)phenyl]pyridine The title compound was prepared using the procedure described in Example 1E substituting 2,6-dimethylpyridine-3-boronic acid for 4-cyanophenylboronic acid. $^1$H NMR (300 MHz, CD$_3$OD) δ 0.97(m, 1H), 1.09 (m, 1H), 1.22 (d, J=6 Hz, 3H), 1.32 (m, 1H), 1.51 (m, 1H), 1.86 (m, 3H), 2.07 (m, 1H), 2.18 (m, 1H), 2.41 (s, 3H), 2.52 (s, 3H), 2.55 (m, 1H), 2.62 (m, 1H), 3.25 (m, 1H), 3.37 (m, 1H), 7.19 (m, 5H), 7.49 (d, J=9 Hz, 1H). MS (DCl—NH$_3$) m/z 321 (M+H)$^+$.

Example 23

5-[4-((1S,2S)-2-{[(2S)-2-Methylpyrrolidin-1-yl]methyl}cyclopropyl)phenyl]pyrimidine The title compound was prepared using the procedure described in Example 1E substituting pyrimidine-3-boronic acid for 4-cyanophenylboronic acid. $^1$H NMR (300 MHz, CD$_3$OD) δ 0.96(m, 1H), 1.1 (m, 1H), 1.16 (d, J=6 Hz, 3H), 1.31 (m, 1H), 1.45 (m, 1H), 1.77 (m, 2H), 1.86 (m, 1H), 2.0 (m, 2H), 2.4 (m, 2H), 3.18 (m, 1H), 3.27 (m, 1H), 7.26 (d, J=9 Hz, 2H), 7.62 (d, J=9 Hz, 2H), 9.03 (s, 2H), 9.09 (s, 1H). MS (DCl—NH$_3$) m/z 294 (M+H)$^+$.

Example 24

N-Isobutyl-N-[4-((1S,2S)-2-{[(2S)-2-methylpyrrolidin-1-yl]methyl}cyclopropyl)phenyl]amine

Example 24A

4-{2-[(2S)-2-Methyl-pyrrolidin-1-ylmethyl]-(1S,2S)-cyclopropyl}-phenylamine

A solution of the product from Example 1D (640 mg, 2.18 mmol, 1-[(1S,2S)-2-(4-bromo-phenyl)-cyclopropylmethyl]-2(S)-methyl-pyrrolidine), lithium bis(trimethylsilyl)amide (560 mg), Pd$_2$(dba)$_3$ (100 mg) and P(t-Bu)$_3$ (10% in hexane, 530 mg) in toluene (3 mL) was heated in a microwave reactor at 160° C. for 40 minutes. The mixture was diluted with dichloromethane and H$_2$O and partitioned. The aqueous layer was extracted with DCM and the organic layers were combined, dried and concentrated to afford a brownish residue which was purified on silica gel eluting with 3% methanol (containing 10% concentrated NH$_4$OH) in dichloromethane to provide the title compound. $^1$H NMR (300 MHz, CD$_3$OD) δ 0.73(m, 1H), 0.85 (m, 1H), 1.07 (m, 1H), 1.13 (d, J=6 Hz, 3H), 1.41 (m, 1H), 1.63 (m, 1H), 1.76 (m, 3H), 2.0 (m, 1H), 2.28 (m, 2H), 3.12 (m, 1H), 3.27 (m, 1H), 6.65 (d, J=9 Hz, 2H), 6.83 (d, J=9 Hz, 2H). MS (DCl—NH$_3$) m/z 231 (M+H)$^+$.

Example 24B

N-Isobutyl-N-[4-((1S,2S)-2-{[(2)-2-methylpyrrolidin-1-yl]methyl}cyclopropyl)phenyl]amine A solution of the product from Example 24A (35 mg, 0.15 mmol, 4-{2-[(2S)-2-methyl-pyrrolidin-1-ylmethyl]-(1S,2S)-cyclopropyl}-phenylamine) and 2-methyl-propionaldehyde (20 mL, 0.23 mmol) in ethanol (8 mL) was treated with borane-pyridine (30 mL) at room temperature and stirred for 16 hours. The mixture was concentrated and the residue was purified on silica gel eluting with 3% methanol (containing 10% concentrated NH$_4$OH) in dichloromethane to provide the title compound. $^1$H NMR (300 MHz, CD$_3$OD) δ 0.82 (m, 1H), 0.94 (m, 1H), 0.95 (d, J=9 Hz, 6H), 1.17 (m, 1H), 1.26 (d, J=6 Hz, 3H), 1.57 (m, 1H), 1.76 (m, 2H), 1.90 (m, 3H), 2.13 (m, 1H), 2.37 (m, 1H), 2.75 (m, 1H), 2.84 (m, 3H), 3.23 (m, 1H), 3.45 (m, 1H), 6.56 (d, J=9 Hz, 2H), 6.86 (d, J=9 Hz, 2H). MS (DCl—NH$_3$) m/z 287 (M+H)$^+$.

Example 25

N-[4-((1S,2S)-2-{[(2S)-2-Methylpyrrolidin-1-yl]methyl}cyclopropyl)phenyl]pyrimidin-5-amine A solution of the product from Example 24A (300 mg, 1.3 mmol, 4-{2-[(2S)-2-methyl-pyrrolidin-1-ylmethyl]-(1S,2S)-cyclopropyl}-phenylamine), 5-bromopyrimidine (311 mg, 1.95 mmol), tris(dibenzylidineacetone)dipalladium(0)•chloroform (40 mg), Cs$_2$CO$_3$ (1 g), and 1,1'-bis(diphenylphosphino)ferrocene (65 mg) in anhydrous dioxane (8 mL) was heated to 110° C. for 48 hours. The mixture was cooled to room temperature, diluted with EtOAc and washed with water and brine. The organic layer was dried (MgSO$_4$), filtered, concentrated under reduced pressure, and purified on silica gel eluting with 3% methanol (containing 10% concentrated NH$_4$OH) in dichloromethane to provide the title compound. $^1$H NMR (300 MHz, CD$_3$OD) δ 0.84 (m, 1H), 0.96 (m, 1H), 1.14 (d, J=6 Hz, 3H), 1.20 (m, 1H), 1.43 (m, 1H), 1.75 (m, 3H), 1.88 (m, 1H), 2.01 (m, 1H), 2.28 (m, 1H), 2.35 (m, 1H), 3.14 (m, 1H), 3.26 (m, 1H), 7.08 (s, 4H), 8.44(s, 2H), 8.51 (s, 1H). MS (DCl—NH$_3$) m/z 309 (M+H)$^+$.

Example 26

4'-((1R,2S)-2-{2-[(2R)-2-Methylpyrrolidin-1-yl]ethyl}cyclopropyl)-1,1'-biphenyl-4-carbonitrile

Example 26A 3-(4-Bromophenyl)prop-2-ene 1-ol

To a solution of ethyl trans-4-bromocinnamate [CAS 24393-53-1] (8 mL, 42.6 mmol) in anhydrous dichloromethane (150 mL) under N$_2$ was added dropwise diisobutylaluminum hydride in dichloromethane (128 mL, 1M, 128 mmol) at −78° C. Following the addition, the mixture was allowed to warm from −78° C. to −30° C. over two hours. The mixture was then cooled back to −78° C. and aqueous 1 N HCl was added. The organic layer was separated, dried with MgSO$_4$, filtered and concentrated under reduced pressure to provide the title compound. $^1$H NMR (300 MHz, CDCl$_3$): δ 1.44 (t, J=6 Hz, 1H), 4.32 (t, J=4.5 Hz, 2H), 6.37 (dt, J=16.5

Hz, J=6 Hz, 1H), 6.57 (dt, J=15 Hz, J=3 Hz, 1H), 7.25 (d, J=9 Hz, 2H), 7.45 (d, J=9 Hz, 2H). MS (DCl—NH$_3$) m/z 214 (M+H)$^+$.

Example 26B

2-Butyl-[1,3,2]dioxaborolane-(S,S)-4,5-dicarboxylic acid bis-dimethylamide 2-(But-1-yl)-tetrahydro-4H-1,3,6,2-dioxazaborocine [CAS 92527-13-4] was prepared from n-butylboronic acid and 2-(2-hydroxy-ethylamino)-ethanol [CAS 111-42-2] as reported in Organic Synthesis, 1998, 76, 86-96. This dioxazaborocine (3 g, 17.5 mmol) and (2S,3S)-2,3-dihydroxy-N,N,N',N'-tetramethyl-butanediamide [CAS 63126-52-3] (4.65 g) were dissolved in anhydrous dichloromethane (95 mL) under N$_2$. Brine (30 mL) was added. The resulting mixture was stirred at room temperature for 1 hour. The two layers were separated, and the aqueous layer was extracted with dichloromethane (30 mL). The combined organic layers were washed with brine, dried over MgSO$_4$, filtered and concentrated in vacuo to provide the title compound as an oil. $^1$H NMR (300 MHz, CDCl$_3$): δ 0.82-0.9 (m, 5H), 1.25-1.45 (m, 4H), 2.98 (s, 6H), 3.2 (s, 6H), 5.52 (s, 2H). MS (DCl—NH$_3$) m/z 271 (M+H)$^+$.

Example 26C (1R,2R)-[2-(4-Bromophenyl)cyclopropyl]methanol

To a −10° C. solution of dimethoxyethane (1.2 mL, 2 equivalents) in anhydrous dichloromethane (30 mL) under N$_2$ was added dropwise, diethylzinc (12 mL, 1M in dichloromethane) followed by dropwise addition of diiodomethane (1.8 mL) over 15 minutes, maintaining the temperature below −5° C. The mixture was stirred another 10 minutes at −10° C. after the addition, then a solution of the dioxaborolane from Example 26B (1.8 g in 5 mL dichloromethane) was added over 6 minutes at −5° C. A solution of the alkene from Example 26A (1 g in 5 mL dichloromethane) was then added dropwise. The cooling bath was removed and the mixture was stirred overnight. The mixture was quenched with the addition of saturated aqueous NH$_4$Cl, and 10% aqueous HCl. This mixture was extracted with ether twice. The combined organic extracts were treated with aqueous 2N NaOH (40 mL) and 30% aqueous H$_2$O$_2$ (5 mL) and then stirred for 5 minutes. The separated organic layer was then washed sequentially with 10% aqueous HCl, aqueous Na$_2$S$_2$O$_3$, aqueous NaHCO$_3$, and brine. The organic layer was dried (MgSO$_4$) and filtered. The filtrate was concentrated in vacuo. The residue was purified on silica gel eluting with 4:1 hexanes/ethyl acetate to provide the title compound.
$^1$H NMR (300 MHz, CDCl$_3$): δ 0.92-1.0 (m, 2H), 1.45-1.48 (m, 2H), 1.76-1.85 (m, 1H), 3.61 (d, J=7.5 Hz, 2H), 6.95 (d, J=9 Hz, 2H), 7.37 (d, J=9 Hz, 2H). MS (DCl—NH$_3$) m/z 228.(M+H)$^+$.

Example 26D (1R,2R)-2-(4-Bromophenyl)cyclopropanecarbaldehyde

DMSO (0.8 mL, 3 equivalents) was added dropwise to a solution of oxalyl chloride (0.48 mL) in anhydrous dichloromethane (50 mL) under N$_2$ at −78° C. A solution of the alcohol from Example 26C (823 mg) in dichloromethane (20 mL) was then added dropwise at −78° C. Stirring at this temperature was continued for 30 minutes, then triethylamine (2 mL, 4 equivalents) was added, and the dry ice bath was removed. After stirring for 1 hour, the mixture was treated with saturated aqueous NH$_4$Cl. The mixture was extracted with ether. The combined organic extracts was dried (MgSO$_4$) and filtered. The filtrate was concentrated under reduced pressure. The residue was purified by eluting through a pad of silica gel with hexane to provide the title compound. $^1$H NMR (300 MHz, CDCl$_3$): δ 1.48 (m, 1H), 1.65 (dt, J=9 Hz, J=6Hz, 1H), 2.15 (m, 1H), 2.57 (m, 1H), 6.98 (d, J=9 Hz, 2H), 7.45 (d, J=9 Hz, 2H), 9.46 (d, J=4.5 Hz, 1H). MS (DCl—NH$_3$) m/z 226 (M+H)$^+$.

Example 26E

1-Bromo-4-[(1R,2S)-2-vinylcyclopropyl]benzene

A solution of the aldehyde from Example 26D (500 mg, 2.22 mmol) and methyltriphenylphosphonium iodide [CAS 2065-66-9] (1.17 g) in anhydrous dichloromethane (50 mL) was stirred at 0° C. under N$_2$. Potassium t-butoxide (340 mg) was added to this chilled mixture. The ice bath was removed, and the mixture was stirred at room temperature for one hour. The mixture was quenched with saturated aqueous NH$_4$Cl. The mixture was extracted with dichloromethane and the combined organic extracts were dried (MgSO$_4$) and filtered. The filtrate was concentrated under reduced pressure and the residue was purified on silica gel with hexanes to provide the title compound. $^1$H NMR (300 MHz, CDCl$_3$): δ 1.1-1.2 (m, 2H), 1.6-1.7 (m, 1H), 1.84-1.92 (m, 1H), 5.05 (ddd, J=34 Hz, J=9Hz, J=1 Hz, 1H), 5.52 (ddd, J=18 Hz, J=10 Hz, J=9 Hz, 1H), 6.95 (d, J=9 Hz, 2H), 7.45 (d, J=9 Hz, 2H). MS (DCl—NH$_3$) m/z 224 (M+H)$^+$.

Example 26F

2-[(1S,2R)-2-(4-Bromophenyl)cycloprop-1-yl]ethanol

To a solution of the alkene from Example 26E (2.25 g, 10 mmol) in anhydrous THF (50 mL) under N$_2$ was added borane-THF (13 mL, 1M) at 0° C. The mixture was stirred at room temperature for two hours then chilled to 0° C. Aqueous hydrogen peroxide solution (35%, 3.5 mL) was added, the ice bath was removed the mixture was allowed to warm to room temperature and stirring was continued for 10 minutes. The mixture was quenched with saturated aqueous NH$_4$Cl and extracted with ether. The combined organic extracts were dried (MgSO$_4$) and filtered. The filtrate was concentrated under reduced pressure. The residue was purified on silica gel with 4:1 hexanes/ethyl acetate to provide the title compound. $^1$H NMR (300 MHz, CDCl$_3$): δ 0.8-0.92 (m, 2H), 1.02-1.1 (m, 1H), 1.46 (s, 1H), 1.6-1.7 (m, 2H), 3.75 (t, J=6 Hz, 2H), 6.9 (d, J=9 Hz, 2H), 7.45 (d, J=9 Hz, 2H). MS (DCl—NH$_3$) m/z 241 (M+H)$^+$.

Example 26G

4'-[(1R,2S)-2-(2-Hydroxyethyl)cycloprop-1-yl]biphenyl-4-carbonitrile

A solution of Example 26F (1.2 g, 5 mmol), 4-cyanophenylboronic acid [CAS 126747-14-6] (1.46 g, 2 equivalents), Pd(PPh$_3$)$_2$Cl$_2$ (350 mg), and Cs$_2$CO$_3$ (6.5 g) in isopropanol (80 mL) under N$_2$ was stirred at reflux overnight. The mixture was partitioned between ethyl acetate and H$_2$O. The organic layer was washed with saturated aqueous NaHCO$_3$ and then with brine. The organic layer was then dried (MgSO$_4$) and filtered. The filtrate was concentrated in vacuo and the resulting residue was purified by chromatography on silica gel eluted with 4:1 hexanes/ethyl acetate to provide the title compound. $^1$H NMR (300 MHz, CDCl$_3$): δ 0.85-1.03 (m, 2H), 1.12-1.2 (m, 1H), 1.65-1.7 (m, 3H), 3.78 (t, J=6 Hz, 2H), 7.15 (d, J=9 Hz, 2H), 7.48 (d, J=9 Hz, 2H), 7.68 (q, J=9 Hz, 4H). MS (DCl—NH$_3$) m/z 264 (M+H)$^+$.

Example 26H

Methanesulfonic acid 2-[(1S,2R)-2-(4'-cyano-biphenyl-4-yl)-cyclopropyl]-ethyl ester To a solution of Example 26G (560 mg, 2.13 mmol) and methanesulfonyl chloride (0.22 mL, 1.2 equivalents) in dichloromethane (10 mL) under N$_2$ was added triethylamine (0.42 mL, 1.4 equivalents) at 0° C. The mixture was stirred at room temperature for 5 hours. The mixture was treated with H$_2$O, and the organic layer was washed with brine, then dried (MgSO$_4$) and filtered. The filtrate was concentrated in vacuo and the resulting residue was purified by chromatography on silica gel eluted with 4:1 hexanes/ethyl acetate to provide the title compound. $^1$H NMR (300 MHz, CDCl$_3$): δ 0.9-1.08 (m, 2H), 1.18-2.02 (m, 2H), 3.0 (s, 3H), 4.35 (t, J=6 Hz, 2H), 7.15 (d, J=9 Hz, 2H), 7.48 (d, J=9 Hz, 2H), 7.68 (q, J=9 Hz, 2H). MS (DCl—NH$_3$) m/z 342 (M+H)$^+$.

Example 26I

4'-((1R,2S)-2-{2-[(2R)-2-Methylpyrrolidin-1-yl]ethyl}cyclopropyl)-1,1'-biphenyl-4-carbonitrile To a solution of the mesylate from Example 26H (500 mg, 1.47 mmol) and potassium carbonate (0.446 g, 3.24 mmol) in DMF (10 mL) was added (R)-2-methylpyrrolidine hydrobromide [CAS 117607-13-3] (300 mg, 1.81 mmol). The mixture was stirred at 50° C. overnight. The mixture was partitioned between ethyl acetate and H$_2$O. The organic layer was washed with brine, dried (MgSO$_4$), and concentrated in vacuo. The resulting residue was purified by chromatography on silica gel eluted with 7.5/20/70 MeOH/EtOAc/CH$_2$Cl$_2$ to provide the title compound. $^1$H NMR (300 MHz, CDCl$_3$, free base): δ 0.85-0.9 (m, 1H), 1.03-1.0 (m, 1H), 1.14 (d, J=6 Hz, 3H), 1.4-2.4 (m, 11H), 2.9 (m, 1H), 3.15-3.23 (m, 1H), 7.15 (d, J=9Hz, 2H), 7.47 (d, J=9 Hz, 2H), 7.66 (q, J=9 Hz, 4H). MS (DCl—NH$_3$) m/z 331.2 (M+H)$^+$. Anal. Calc. for C$_{23}$H$_{26}$N$_2$C$_4$H$_6$O$_6$ 1.25H$_2$O (L-tartaric acid salt): C, 64.46; H, 6.91; N, 5.57. Found: C, 64.46; H, 6.91; N, 5.57.

Example 27

(2R)-1-{2-[(1S,2R)-2-(4-Bromophenyl)cyclopropyl]ethyl}-2-methylpyrrolidine

Example 27A (1S,2R)-Methanesulfonic acid 2-[2-(4-bromo-phenyl)-cyclopropyl]-ethyl ester The alcohol from Example 26F, 2-[(1S,2R)-2-(4-bromophenyl)cycloprop-1-yl]ethanol, was converted to (1S,2R)-methanesulfonic acid 2-[2-(4-bromo-phenyl)-cyclopropyl]-ethyl ester according to the methods outlined in Example 26H.

Example 27B (2R)-1-{2-[(1S,2R)-2-(4-Bromophenyl)cyclopropyl]ethyl}-2-methylpyrrolidine The title compound was prepared according to the methods outlined in Example 26I substituting the product from Example 27A, (1R,2R)-methanesulfonic acid 2-[2-(4-bromo-phenyl)-cyclopropyl]-ethyl ester, for the product from Example 26H. $^1$H NMR (300 MHz, CDCl$_3$, free base): δ 0.75-0.9 (m, 2H), 0.97-1.04 (m, 1H), 1.15 (d, J=6 Hz, 3H), 1.5-1.65 (m, 8H), 1.85-2.35 (m, 3H), 2.85-2.95 (m, 1H), 3.12-3.20 (m, 1H), 6.9 (d, J=9 Hz, 2H), 7.33 (d, J=9 Hz, 2H). MS (DCl—NH$_3$) m/z 310 (M+H)$^+$.

Example 28

4'-((1S,2R)-2-{2-[(2R)-2-Methylpyrrolidin-1-yl]ethyl}cycloprop-1-yl)-1,1'-biphenyl-4-carbonitrile

Example 28A

2-Butyl-[1,3,2]dioxaborolane-(R,R)-4,5-dicarboxylic acid bis-dimethylamide 2-(But-1-yl)-tetrahydro-4H-1,3,6,2-dioxazaborocine [CAS 92527-13-4] (3 g, 17.5 mmol), which was prepared from n-butylboronic acid and 2-(2-hydroxy-ethylamino)-ethanol [CAS 111-42-2] as reported in Organic Synthesis, 1998, 76, 86-96, and (2R,3R)-2,3-dihydroxy-N,N,N',N'-tetramethyl-butanediamide [CAS 26549-65-5] (9.85 g) were dissolved in anhydrous dichloromethane (160 mL) under N$_2$. Brine (25 mL) was added. The resulting mixture was stirred at room temperature for about 16 hours. The two layers were separated, and the aqueous layer was extracted with dichloromethane. The combined organic layers were washed with 50 mL brine, dried over MgSO$_4$, filtered and concentrated in vacuo to provide the title compound as an oil.

Example 28B (1S,2S)-[2-(4-Bromophenyl)cyclopropyl]methanol

To a −10° C. solution of dimethoxyethane (5.2 mL) in anhydrous dichloromethane (200 mL) under N$_2$ was added dropwise, diethylzinc (62.6 mL, 1M in dichloromethane) followed by dropwise addition of diiodomethane (10.1 mL), maintaining the temperature below −5° C. The mixture was stirred another 10 minutes at −10° C. after the addition, then a solution of the dioxaborolane (2-butyl-[1,3,2]dioxaborolane-(R,R)-4,5-dicarboxylic acid bis-dimethylamide) (8.8 g in 40 mL dichloromethane) was added at −5° C. A solution of the alkene from Example 26A (3-(4-bromophenyl)prop-2-1-ol, 5.3 g in 50 mL dichloromethane) was then added dropwise. The cooling bath was removed and the mixture was stirred overnight. The mixture was quenched with the addition of saturated aqueous NH$_4$Cl, and 10% aqueous HCl. This mixture was extracted with ether twice. The combined organic extracts were treated with aqueous 2N NaOH (250 mL) and 30% aqueous H$_2$O$_2$ (35 mL) and then stirred for 5 minutes. The organic layer was then washed sequentially with 10% aqueous HCl, aqueous Na$_2$S$_2$O$_3$, aqueous NaHCO$_3$, and brine. The organic layer was dried (MgSO$_4$) and filtered. The filtrate was concentrated in vacuo. The residue was purified on silica gel eluting with hexanes/ethyl acetate to provide the title compound.

Example 28C (1S,2S)-2-(4-Bromophenyl)cyclopropanecarbaldehyde

DMSO (3 equivalents) was added dropwise to a solution of oxalyl chloride in anhydrous dichloromethane under $N_2$ at −78° C. A solution of the alcohol from Example 28B ((1S,2S)-[2-(4-bromophenyl)cyclopropyl]methanol) in dichloromethane was then added dropwise at −78° C. Stirring at this temperature was continued for 30 minutes, then triethylamine (4 equivalents) was added and the dry ice bath was removed. After stirring for 1 hour, the mixture was treated with saturated aqueous $NH_4Cl$. The mixture was extracted with ether. The combined organic extracts was dried ($MgSO_4$) and filtered. The filtrate was concentrated under reduced pressure. The residue was purified by eluting through a pad of silica gel with hexane to provide the title compound.

Example 28D

1-Bromo-4-[(1S,2R)-2-vinylcyclopropyl]benzene

A solution of the aldehyde from Example 28C [(1S,2S)-2-(4-bromophenyl)cyclopropanecarbaldehyde] and methyltriphenylphosphonium iodide [CAS 2065-66-9] in anhydrous dichloromethane was stirred at 0° C. under $N_2$. Potassium t-butoxide was added to this chilled mixture. The ice bath was removed and the mixture was stirred at room temperature for one hour. The mixture was quenched with saturated aqueous $NH_4Cl$. The mixture was extracted with dichloromethane and the combined organic extracts were dried ($MgSO_4$) and filtered. The filtrate was concentrated under reduced pressure and the residue was purified on silica gel with hexanes to provide the title compound.

Example 28E

2-[(1R,2S)-2-(4-Bromophenyl)cycloprop-1-yl]ethanol

To a solution of the alkene from Example 28D (1-bromo-4-[(1S,2R)-2-vinylcyclopropyl]benzene) in anhydrous THF (50 mL) under $N_2$ was added borane-THF at 0° C. The mixture was stirred at room temperature for two hours and then chilled to 0° C. Aqueous hydrogen peroxide (30%) solution was added, the ice bath was removed, and the mixture was allowed to warm to room temperature with continued stirring for 10 minutes. The mixture was quenched with saturated aqueous $NH_4Cl$ and extracted with ether. The combined organic extracts were dried ($MgSO_4$) and filtered. The filtrate was concentrated under reduced pressure. The residue was purified on silica gel with 4:1 hexanes/ethyl acetate to provide the title compound.

Example 28F 4'-[(1S,2R)-2-(2-Hydroxyethyl)cycloprop-1-yl]biphenyl-4-carbonitrile A solution of the product of Example 28E (2-[(1R,2S)-2-(4-bromophenyl)cycloprop-1-yl]ethanol), 4-cyanophenylboronic acid [CAS 126747-14-6] (2 equivalents), $Pd(PPh_3)_2Cl_2$, and $Cs_2CO_3$ in isopropanol under $N_2$ was stirred at reflux overnight. The mixture was partitioned between ethyl acetate and $H_2O$. The organic layer was washed with saturated aqueous $NaHCO_3$ and then with brine. The organic layer was then dried ($MgSO_4$) and filtered. The filtrate was concentrated in vacuo and the resulting residue was purified by chromatography on silica gel eluted with 4:1 hexanes/ethyl acetate to provide the title compound.

Example 28G

Methanesulfonic acid, 2-[(1R,2S)-2-(4'-cyano-biphenyl-4-yl)-cyclopropyl]-ethyl ester To a solution of the product of Example 28F (4'-[(1S,2R)-2-(2-hydroxyethyl)cycloprop-1-yl]biphenyl-4-carbonitrile) and methanesulfonyl chloride (1.2 equivalents) in dichloromethane under $N_2$ was added triethylamine (1.4 equivalents) at 0° C. The mixture was stirred at room temperature overnight, and then the mixture was treated with $H_2O$. The separated organic layer was washed with brine, dried ($MgSO_4$) and filtered. The filtrate was concentrated in vacuo and the resulting residue was purified by chromatography on silica gel eluted with 4:1 hexanes/ethyl acetate to provide the title compound.

Example 28H

4'-((1S,2R)-2-{2-[(2R)-2-Methylpyrrolidin-1-yl]ethyl}cyclopropyl)-1,1'-biphenyl-4-carbonitrile To a solution of the mesylate from Example 28G (methanesulfonic acid, 2-[(1R,2S)-2-(4'-cyano-biphenyl-4-yl)-cyclopropyl]-ethyl ester) and potassium carbonate in DMF was added (R)-2-methylpyrrolidine hydrobromide [CAS 117607-13-3]. The mixture was stirred at 50° C. overnight. The mixture was partitioned between ethyl acetate and $H_2O$. The organic layer was washed with brine, dried ($MgSO_4$), and concentrated in vacuo. The resulting residue was purified by chromatography on silica gel eluted with 7.5/20/70 MeOH/EtOAc/$CH_2Cl_2$ to provide the title compound. $^1$H NMR (300 MHz, $CDCl_3$, free base): δ 0.88-1.0 (m, 2H), 1.18 (d, J=6 Hz, 3H), 1.4-2.4 (m, 11H), 2.9 (m, 1H), 3.15-3.23 (m, 1H), 7.15 (d, J=9 Hz, 2H), 7.47 (d, J=9 Hz, 2H), 7.66 (q, J=9 Hz, 4H). MS (DCl—$NH_3$) m/z 331.2 $(M+H)^+$. Anal. Calc. for $C_{23}H_{26}N_2C_4H_6O_6$ 1.25$H_2O$ (L-tartaric acid salt): C, 64.46; H, 6.91; N, 5.57. Found: C, 64.46; H, 6.91; N, 5.57.

Example 29

4'-((1R,2S)-2-{2-[(2R)-2-Methylpyrrolidin-1-yl]ethyl}cyclopropyl)-1,1'-biphenyl-4-carbonitrile

Example 29A 3-(4-Bromophenyl)-N-methoxy-N-methylacrylamide

A solution of oxalyl chloride in dichloromethane (2 M, 100 mL, 200 mmol) was added dropwise to a stirred solution of trans-4-bromocinnamic acid [CAS 1200-07-3] (25.0 g, 110 mmol) and DMF (0.5 mL) in dichloromethane (300 mL) at 0° C. under a dry nitrogen atmosphere. The nitrogen line and cooling bath were removed and the mixture was stirred at room temperature until gas evolution had ceased. Volatiles were removed under reduced pressure, and the residue was redissolved in dichloromethane (200 mL). The resulting solution was added dropwise to a stirred solution of N,O-dimethylhydroxylamine hydrochloride (21.5 g, 220 mmol) and triethylamine (61.4 mL, 440 mmol) in dichloromethane (150 mL) at 0° C. When the addition was complete, the cooling bath was removed and the mixture was stirred overnight at room temperature. Insoluble material was removed by filtration and the filtrate was concentrated under reduced pressure.

The residue was partitioned between ethyl acetate and aqueous 10% citric acid. The organic layer was successively washed with aqueous 10% citric acid, aqueous 3 N sodium hydroxide, and brine. The ethyl acetate solution was then dried (MgSO$_4$) and filtered. The filtrate was concentrated under reduced pressure, and the residue was purified by column chromatography (65:35 hexane/ethyl acetate) to provide the title compound. $^1$H NMR (300 MHz, CDCl$_3$): δ 3.31 (s, 3H), 3.76 (s, 3H), 7.02 (d, J=15 Hz, 1H), 7.43 (d, J=9 Hz, 2H), 7.51 (d, J=9 Hz, 2H), 7.67 (d, J=9 Hz, 1H). MS (DCl—NH$_3$) m/z 270 (M+H)$^+$, m/z 287 (M+NH$_4$)$^+$.

Example 29B 2-(4-Bromo-phenyl)-trans-cyclopropanecarboxylic acid, N-methoxy-N-methyl-amide (racemic)

A stirred solution of trimethylsulfoxonium iodide (26.78 g, 119 mmol) in DMSO (100 mL) at 0° C. was treated with sodium hydride (60% oil dispersion, 4.57 g, 114 mmol) in small portions. When the addition was complete, the ice bath was removed and the mixture was stirred at room temperature for 45 minutes. A solution of the alkene intermediate from Example 29A (26.85 g, 99 mmol) in DMSO (100 mL) was added dropwise to the mixture and stirring was continued overnight. The mixture was diluted with saturated aqueous ammonium chloride and the mixture was extracted with diethyl ether (4×100 mL). The combined extracts were dried (MgSO$_4$) and filtered. The filtrate was concentrated under reduced pressure to provide an oil that was purified by column chromatography (70:30 hexane/ethyl acetate) to provide the title compound. $^1$H NMR (300 MHz, CDCl$_3$): δ 1.23-1.31 (m, 1H), 1.60-1.67 (m, 1H), 2.32-2.42 (m, 1H), 2.42-2.50 (m, 1H), 3.23 (s, 3H), 3.69 (s, 3H), 7.00 (d, J=9 Hz, 2H), 7.39 (d, J=9 Hz, 2H). MS (DCl—NH$_3$) m/z 284 (M+H)$^+$, m/z 301 (M+NH$_4$)$^+$.

Example 29C 2-(4-Bromo-phenyl)-trans-cyclopropanecarboxylic acid (racemic)

A solution of the product from Example 29B (24.3 g, 86 mmol) and potassium t-butoxide (80.8 g, 684 mmol) in diethyl ether (900 mL) and water (10 mL) was stirred at room temperature for three days. The mixture was then slowly acidified by the addition of concentrated hydrochloric acid. The ether layer was washed with brine and the acidic aqueous layer was extracted with ethyl acetate (2×100 mL). The ether layer and the ethyl acetate extracts were combined, dried (MgSO$_4$), and filtered. The filtrate was concentrated under reduced pressure to provide the title compound. $^1$H NMR (300 MHz, CDCl$_3$): δ 1.33-1.42 (m, 1H), 1.63-1.71 (m, 1H), 1.84-1.91 (m, 1H), 2.51-2.60 (m, 1H), 6.98 (d, J=9 Hz, 2H), 7.41 (d, J=9 Hz, 2H), 11.08 (br s, 1H). MS (DCl—NH$_3$) m/z 258 (M+NH$_4$)$^+$.

Example 29D

[(1R,2R)-2-(4-Bromophenyl)cyclopropyl]-{(1S,5R,7R)-(10,10-dimethyl-3,3-dioxo-3λ$^6$-thia-4-azatricyclo[5.2.1.0$^{1.5}$]dec-4-yl)}methanone and

[(1S,2S)-2-(4-Bromophenyl)cyclopropyl]-{(1S,5R,7R)-(10,10-dimethyl-3,3-dioxo-3λ$^6$-thia-4-azatricyclo[5.2.1.0$^{1.5}$]dec-4-yl)}methanone A stirred solution of the racemic, trans-cyclopropyl intermediate in Example 29C (20.5 g, 85 mmol) in DMF (100 mL) was treated with 1,1'-carbonyldiimidazole (15.2 g, 94 mmol) under a dry nitrogen atmosphere. The mixture was stirred at 40° C. for 1 hour and then (1S)-(−)-2,10-camphorsultam ([CAS 94594-90-8], Aldrich catalog number 29, 835-2) (25.82 g, 120 mmol) and DBU (12.7 mL, 85 mmol) were added. The mixture was stirred at 40° C. for 6 hours and then at room temperature overnight. The mixture was then partitioned between ethyl acetate and aqueous 2 N hydrochloric acid. The organic layer was washed with saturated aqueous sodium bicarbonate and then with brine. The ethyl acetate solution was then dried (MgSO$_4$), and filtered. The filtrate was concentrated under reduced pressure, and the residue was purified by column chromatography (90:5:5 hexane/dichloromethane/isopropanol). Drying under high vacuum supplied a mixture of diastereomers. The diastereomers were separated by elution through a chiral column (Chiralcel OJ®, 90:10 hexane/ethanol). The first diastereomer to elute (retention time: 11.8 minutes) was identified by x-ray crystallography as possessing the S, S absolute configuration at the cyclopropyl carbons. The later-eluting diastereomer (retention time: 19 minutes was assigned the R,R absolute configuration at the cyclopropyl carbons.

Early-eluting diastereomer (S,S-cyclopropyl), [(1S,2S)-2-(4-bromophenyl)cyclopropyl]-{(1S,5R,7R)-(10,10-dimethyl-3,3-dioxo-3λ$^6$-thia-4-azatricyclo[5.2.1.0$^{1.5}$]dec-4-yl)}methanone: $^1$H NMR (300 MHz, CDCl$_3$): δ 0.97 (s, 3H), 1.17 (s, 3H), 1.30-1.47 (m, 3H), 1.61-1.69 (m, 1H), 1.83-1.99 (m, 3H), 2.01-2.19 (m, 2H), 2.53-2.61 (m, 1H), 2.63-2.71 (m, 1H), 3.42-3.56 (m, 2H), 3.86-3.92 (m, 1H), 7.10 (d, J=9 Hz, 2H), 7.40 (d, J=9 Hz, 2H). MS (DCl—NH$_3$) m/z 455 (M+NH$_4$)$^+$.

Late-eluting diastereomer (R,R-cyclopropyl), [(1R,2R)-2-(4-bromophenyl)cyclopropyl]-{(1S,5R,7R)-(10,10-dimethyl-3,3-dioxo-3λ$^6$-thia-4-azatricyclo[5.2.1.0$^{1.5}$]dec-4-yl)}methanone: $^1$H NMR (300 MHz, CDCl$_3$): δ 0.98 (s, 3H), 1.20 (s, 3H), 1.29-1.47 (m, 3H), 1.1.73-1.83 (m, 1H), 1.83-2.00 (m, 3H), 2.00-2.18 (m, 2H), 2.46-2.59 (m, 2H), 3.39-3.56 (m, 2H), 3.86-4.96 (m, 1H), 7.09 (d, J=9 Hz, 2H), 7.39 (d, J=9 Hz, 2H). MS (DCl—NH$_3$) m/z 455 (M+NH$_4$)$^+$.

Example 29E (1R,2R)-2-(4-Bromophenyl)cyclopropanecarbaldehyde

A solution of the later-eluting, R,R-diastereomer ([(1R,2R)-2-(4-bromophenyl)cyclopropyl]-{(1S,5R,7R)-(10,10-dimethyl-3,3-dioxo-3λ$^6$-thia-4-azatricyclo[5.2.1.0$^{1.5}$]dec-4-yl)}methanone) described in Example 29D (5.2 g, 11.86 mmol) in dichloromethane (100 mL) was stirred under a dry nitrogen atmosphere at −78° C. A 1 M solution of diisobutylaluminum hydride in dichloromethane (26.1 mL, 26.1 mmol) was added dropwise to the mixture. When the addition was complete, the mixture was stirred at −78° C. for 3 hour. Methanol (27 mL) was then added dropwise at −78° C. The dry ice bath was then replaced with an ice water bath and saturated aqueous ammonium chloride was added to quench the mixture. After 10 minutes, the insoluble material was removed by filtration and the organic layer was isolated, dried (MgSO$_4$), and filtered. The filtrate was concentrated under reduced pressure to provide a colorless oil that was purified by column chromatography (9:1 hexane/ethyl acetate). Fractions containing product were combined and concentrated under reduced pressure to provide the title compound. $^1$H NMR (300 MHz, CDCl$_3$): δ 1.45-1.57 (m, 1H), 1.70-1.78 (m, 1H), 2.11-2.19 (m, 1H), 2.55-2.63 (m, 1H), 6.99 (d, J=9 Hz, 2H), 7.42 (d, J=9 Hz, 2H), 9.35 (d, J=4.5 Hz, 1H). MS (DCl—NH₃) m/z 225 (M+H)⁺, m/z 242 (M+NH₄)⁺.

Example 29F

1-Bromo-4-[(1R,2S)-2-vinyl-cycloprop-1-yl]benzene

The aldehyde intermediate from Example 29E (2.35 g, 10.44 mmol) was converted to the alkene by the methods outlined in Example 26E, followed by chromatography (100% hexane) provided the title compound. ¹H NMR (300 MHz, CDCl₃): δ 1.07-1.19 (m, 2H), 1.60-1.71 (m, 1H), 1.83-1.91 (m, 1H), 4.91-4.97 (m, 1H), 5.05-5.14 (m, 1H), 5.45-5.59 (m, 1H), 6.93 (d, J=9 Hz, 2H), 7.36 (d, J=9 Hz, 2H). MS (DCl—NH₃) m/z 241 (M+NH₄)⁺.

Example 29G

2-[(1S,2R)-2-(4-Bromophenyl)cycloprop-1-yl]ethanol

The alkene intermediate from Example 29F (1.64 g, 7.35 mmol) was converted to the alcohol by the method of Example 26F, followed by chromatography (7:3 hexane/ethyl acetate) provided the title compound. ¹H NMR (300 MHz, CDCl₃): δ 0.96-0.79 (m, 2H), 1.00-1.14 (m, 1H), 1.54-1.76 (m, 3H), 4.91-4.97 (m, 1H), 3.76 (t, J=6 Hz, 2H), 6.92 (d, J=9 Hz, 2H), 7.35 (d, J=9 Hz, 2H). MS (DCl—NH₃) m/z 258 (M+NH₄)⁺.

Example 29H

4'-[(1R,2S)-2-(2-Hydroxyethyl)cycloprop-1-yl]biphenyl-4-carbonitrile

The bromophenyl intermediate from Example 29G (0.83 g, 3.44 mmol) was converted to the biphenyl intermediate by the method of Example 26G, but with a total reaction time of 45 minutes, followed by chromatography (7:3 hexane/ethyl acetate) provided the title compound. ¹H NMR (300 MHz, CDCl₃): δ 0.87-0.95 (m, 1H), 0.97-1.04 (m, 1H), 1.11-1.24 (m, 1H), 1.61-1.79 (m, 3H), 3.79 (t, J=6 Hz, 2H), 7.15 (d, J=9 Hz, 2H), 7.48 (d, J=9 Hz, 2H), 7.67 (q, J=9 Hz, 4H). MS (DCl—NH₃) m/z 281 (M+NH₄)⁺.

Example 29I

Methanesulfonic acid, 2-[(1S,2R)-2-(4'-cyano-biphenyl-4-yl)-cyclopropyl]-ethyl ester The alcohol intermediate from Example 29H (0.31 g, 1.18 mmol) was converted to the mesylate intermediate by the method of Example 26H to provide the title compound. ¹H NMR (300 MHz, CDCl₃): δ 0.89-0.96 (m, 1H), 1.00-1.08 (m, 1H), 1.13-1.24 (m, 1H), 1.76-1.93 (m, 3H), 2.98 (s, 3H), 4.35 (t, J=6 Hz, 2H), 7.16 (d, J=9 Hz, 2H), 7.49 (d, J=9 Hz, 2H), 7.68 (q, J=9 Hz, 4H). MS (DCl—NH₃) m/z 359 (M+NH₄)⁺.

Example 29J

4'-((1R,2S)-2-{2-[(2R)-2-Methylpyrrolidin-1-yl]ethyl}cyclopropyl)-1,1'-biphenyl-4-carbonitrile The mesylate intermediate from Example 29I (0.37 g, 1.08 mmol) was converted to the final product by the method of Example 26I. The title compound was obtained after column chromatography (95:5:trace dichloromethane/methanol/ammonium hydroxide). The title compound was dissolved in methanol. To this stirred solution was added a solution of one equivalent of L-tartaric acid in methanol. After stirring for 15 minutes, the solution was concentrated to half volume and treated with ethyl ether to induce crystallization of the title compound as the mono L-tartaric acid salt. ¹H NMR (300 MHz, CD₃OD, L-tartaric acid salt): δ 0.93-1.10 (m, 2H), 1.13-1.24 (m, 1H), 1.44 (d, J=6 Hz, 3H), 1.71-1.85 (m, 2H), 1.85-1.99 (m, 2H), 2.02-2.15 (m, 2H), 2.25-2.49 (m, 1H), 3.06-3.19 (m, 2H), 3.41-3.56 (m, 2H), 3.59-3.72 (m, 1H), 4.39 (s, 2H), 7.21 (d, J=9 Hz, 2H), 7.58 (d, J=9 Hz, 2H), 7.77 (s, 4H). MS (DCl—NH₃) m/z 331 (M+H)⁺.

Example 30

4'-((1S,2R)-2-{2-[(2R)-2-Methylpyrrolidin-1-yl]ethyl}cyclopropyl)-1,1'-biphenyl-4-carbonitrile

Example 30A (1S,2S)-2-(4-Bromophenyl)cyclopropanecarbaldehyde

A solution of the early-eluting, S,S-diastereomer ([(1S,2S)-2-(4-bromophenyl)cyclopropyl]-{(1S,5R,7R)-(10,10-dimethyl-3,3-dioxo-3λ⁶-thia-4-azatricyclo[5.2.1.0¹·⁵]dec-4-yl)}methanone) described in Example 29D in dichloromethane was stirred under a dry nitrogen atmosphere at −78° C. A 1 M solution of diisobutylaluminum hydride in dichloromethane was added dropwise to the mixture. When the addition was complete, the mixture was stirred at −78° C. for 3 hours. Methanol was then added dropwise at −78° C. The dry ice bath was then replaced with an ice water bath and saturated aqueous ammonium chloride was added to quench the mixture. After 10 minutes, the insoluble material was removed by filtration and the organic layer was separated, dried (MgSO₄), and filtered. The filtrate was concentrated under reduced pressure, and the residue was purified by column chromatography (9:1 hexane/ethyl acetate). Fractions containing product were combined and concentrated under reduced pressure to provide the title compound.

Example 30B

1-Bromo-4-[(1S,2R)-2-vinyl-cycloprop-1-yl]benzene

The product from Example 30A was subjected to the conditions outlined in Example 26E, followed by chromatography (100% hexane) to provide the title compound.

Example 30C

2-[(1R,2S)-2-(4-Bromophenyl)cycloprop-1-yl]ethanol

The product from Example 30B was subjected to the conditions outlined in Example 26F, followed by chromatography (7:3 hexane/ethyl acetate) to provide the title compound.

Example 30D

4'-[(1S,2R)-2-(2-Hydroxyethyl)cycloprop-1-yl]biphenyl-4-carbonitrile

The product from Example 30C was subjected to the conditions outline in Example 26G, followed by chromatography (7:3 hexane/ethyl acetate) to provide the title compound.

Example 30E

Methanesulfonic acid, 2-[(1R,2S)-2-(4'-cyano-biphenyl-4-yl)-cyclopropyl]-ethyl ester The product from Example 30D was subjected to the conditions outlined in Example 26H to provide the title compound.

Example 30F

4'-((1S,2R)-2-{2-[(2R)-2-methylpyrrolidin-1-yl]ethyl}cyclopropyl)-1,1'-biphenyl-4-carbonitrile The product from Example 30E (methanesulfonic acid, 2-[(1R,2S)-2-(4'-cyano-biphenyl-4-yl)-cyclopropyl]-ethyl ester), 0.40 g, 1.17 mmol) was further converted to 4'-((1S,2R)-2-{2-[(2R)-2-methylpyrrolidin-1-yl]ethyl}cyclopropyl)-1,1'-biphenyl-4-carbonitrile through the procedure described in Example 29J. Column chromatography (96:4:trace dichloromethane/methanol/ammonium hydroxide) provided the title compound. The title compound was dissolved in ethyl ether and anhydrous HCl gas was bubbled into the solution to provide the hydrochloride salt of the title compound that was crystallized from methanol/ethyl ether. $^1$H NMR (300 MHz, CD$_3$OD, hydrochloride salt): δ 0.95-1.12 (m, 2H), 1.14-1.24 (m, 1H), 1.45 (d, J=6 Hz, 3H), 1.66-1.81 (m, 1H), 1.81-1.93 (m, 3H), 2.00-2.17 (m, 2H), 2.27-2.41 (m, 1H), 3.07-3.26 (m, 2H), 3.43-3.56 (m, 2H), 3.64-3.75 (m, 1H), 7.21 (d, J=9 Hz, 2H), 7.58 (d, J=9 Hz, 2H), 7.77 (s, 4H). MS (DCl—NH$_3$) m/z 331 (M+H)$^+$.

Example 31

4'-[(trans)-2-(2-Pyrrolidin-1-ylethyl)cyclopropyl]-1,1'-biphenyl-4-carbonitrile

Example 31A tert-Butyl(but-3-ynyloxy)dimethylsilane

A stirred, 0° C. solution of homopropargyl alcohol (10 g, 0.14 mol) and tert-butyldimethylsilyl chloride (21.5 g, 0.14 mol) in dichloromethane (50 mL) was treated with triethylamine (22.8 mL, 0.168 mol). The mixture was then stirred overnight at room temperature. The mixture was washed with water and the organic layer was dried (MgSO$_4$) and filtered. The filtrate was concentrated under reduced pressure, and the residue was purified by chromatography (95:5 hexane/ethyl acetate) to provide the title compound. $^1$H NMR (300 MHz, CDCl$_3$): δ 0.08 (s, 6H), 0.90 (s, 9H), 1.96 (t, J=3 Hz, 1H), 2.41 (dt, J=6 Hz, J=3 Hz, 2H), 3.75 (d, J=6 Hz, 2H).

Example 31B

Tert-butyl-dimethyl-(4-tributylstannanyl-but-3-enyloxy)-silane

A solution of Example 31A (1.08 g, 5.87 mmol), tri-(n-butyl)tin hydride (1.43 mL, 5.31 mmol), and AIBN (cat.) in benzene (10 mL) was stirred at 80° C. for 3 hours. Volatiles were removed under reduced pressure to provide the title compound as a colorless oil (>95% E-isomer). $^1$H NMR (300 MHz, CDCl$_3$): δ 0.05 (s, 6H), 0.80-0.98 (m, 15H), 0.90 (s, 9H), 1.23-1.38 (m, 6H), 1.42-1.53 (m, 6H), 2.34-2.40 (m, 2H), 3.66 (d, J=6 Hz, 2H), 5.94-5.98 (m, 2H).

Example 31C

4'-[4-(Tert-butyl-dimethyl-silanyloxy)-but-1-enyl]-biphenyl-4-carbonitrile

A solution of Example 31B (4.95 g, 10.4 mmol), 4'-cyanobiphenyl triflate (3.1 g, 9.48 mmol, prepared from 4'-hydroxybiphenyl-4-carbonitrile by standard methods), and Pd(PPh$_3$)$_2$Cl$_2$ (0.332 g, 0.47 mmol) in DMF (20 mL) was stirred at 80° C. overnight. The mixture was cooled to room temperature and partitioned between ethyl acetate and water. The organic layer was dried (MgSO$_4$) and filtered. The filtrate was concentrated under reduced pressure and the residue was purified by column chromatography (97.5:2.5 hexane/ethyl acetate) to provide the title compound. $^1$H NMR (300 MHz, CDCl$_3$): δ 0.07 (s, 6H), 0.91 (s, 9H), 2.46 (q, J=6 Hz, 2H), 3.75 (t, J=6 Hz, 2H), 6.32 (d, J=16 Hz, 1H), 6.48 (d, J=16 Hz, 1H), 7.44 (d, J=9 Hz, 2H), 7.54 (d, J=9 Hz, 2H), 7.65-7.74 (m, 4H). MS (DCl—NH$_3$) m/z 364 (M+H)$^+$, m/z 359 (M+NH$_4$)$^+$.

Example 31D

Trans-4'{2-[2-(tert-butyldimethylsilanyloxy)ethyl]cyclopropyl}biphenyl-4-carbonitrile (racemic)

The cyclopropanation reaction was conducted according to the procedure in Tetrahedron Letters 1998, 39, 8621-8624. A stirred solution of diethyl zinc (1 M in hexane, 4.1 mL, 4.1 mmol) in dichloromethane (10 mL) was chilled to 0° C. A solution of trifluoroacetic acid (0.32 mL, 4.1 mmol) in dichloromethane (2 mL) was added dropwise to the cold mixture. Stirring at 0° C. was continued for 20 minutes, and then a solution of diiodomethane (0.4 mL, 4.9 mmol) in dichloromethane (2 mL) was added dropwise to the cold mixture. After 20 minutes, a solution of Example 31C (0.6 g, 1.65 mmol) in dichloromethane (5 mL) was added to the mixture and the ice bath was removed. The mixture was stirred at room temperature for 3 hours, diluted with 0.1 N aqueous HCl and extracted with hexane. The crude product was purified by preparative thin layer chromatography (97:3 hexane/ethyl acetate) to provide the title compound. $^1$H NMR (300 MHz, CDCl$_3$): δ 0.04 (s, 3H), 0.05 (s, 3H), 0.84-0.97 (m, 2H), 0.89 (s 3H), 1.56-1.75 (m, 3H), 3.74 (t, J=6 Hz, 2H), 7.14 (d, J=9 Hz, 2H), 7.48 (d, J=9 Hz, 2H), 7.65 (d, J=9 Hz, 2H), 7.71 (d, J=9 Hz, 2H). MS (DCl—NH$_3$) m/z 378 (M+H)$^+$, m/z 359 (M+NH$_4$)$^+$

Example 31E

Trans-4'-{2-[2-(tert-butyl-dimethyl-silanyloxy)-ethyl]-cyclopropyl}-biphenyl-4-carbonitrile (racemic)

A 1 M solution of tetrabutylammonium fluoride in THF (3.1 mL, 3.1 mmol) was added to a stirred, room temperature solution of Example 31D (0.585 g, 1.55 mmol) in THF (5 mL). The mixture was stirred for 2 hours, partitioned between ethyl acetate and water. The organic layer was dried (MgSO$_4$) and filtered. The filtrate was concentrated under reduced pressure, and the residue was purified by column chromatography (65:35 hexane/ethyl acetate) to provide the title compound. $^1$H NMR (300 MHz, CDCl$_3$): δ 0.87-0.97 (m, 1H), 0.97-1.05 (m, 1H), 1.12-1.21 (m, 1H), 1.64-1.79 (m, 2H), 3.76-3.84 (m, 2H), 7.15 (d, J=9 Hz, 2H), 7.48 (d, J=9 Hz, 2H), 7.68 (q, J=9 Hz, 4H). MS (DCl—NH$_3$) m/z 281 (M+H)$^+$.

Example 31F

Methanesulfonic acid, trans-2-[2-(4'-cyano-biphenyl-4-yl)-cyclopropyl]-ethyl ester (racemic)

Triethylamine (0.18 mL, 1.29 mmol) was added to a stirred, room temperature solution of Example 31E (0.24 g, 0.91 mmol) and methanesulfonyl chloride (0.092 mL, 1.19 mmol) in dichloromethane (10 mL). After stirring for 30 minutes, the mixture was washed with water. The organic layer was dried (MgSO$_4$), and filtered. The filtrate was concentrated under reduced pressure to provide the crude title compound. $^1$H NMR (300 MHz, CDCl$_3$): δ 0.89-0.96 (m, 1H), 1.01-1.08 (m, 1H), 1.13-1.23 (m, 1H), 1.76-1.83 (m, 1H), 1.83-1.93 (m, 2H), 2.99 (s, 3H), 4.35 (t, J=6 Hz, 2H), 7.16 (d, J=9 Hz, 2H), 7.49 (d, J=9 Hz, 2H), 7.68 (q, J=9 Hz, 4H). MS (DCl—NH$_3$) m/z 359 (M+NH$_4$)$^+$.

Example 31G

4'-[(trans)-2-(2-Pyrrolidin-1-ylethyl)cyclopropyl]-1,1'-biphenyl-4-carbonitrile

A solution of Example 31F (0.054 g, 0.158 mmol) in pyrrolidine (5 mL) was stirred at reflux overnight. Volatiles were removed under reduced pressure, and the residue was purified by column chromatography (95:5 dichloromethane/methanol) to provide the title compound. $^1$H NMR (300 MHz, CDCl$_3$): δ 0.84-0.91 (m, 1H), 0.92-1.0 (m, 1H), 1.05-1.16 (m, 1H), 1.5-1.9 (m, 8H), 2.48-2.75 (m, 5H), 7.14 (d, J=9 Hz, 2H), 7.48 (d, J=9 Hz, 2H), 7.65 (q, J=9 Hz, 4H). MS (DCl—NH$_3$) m/z 317 (M+H)$^+$.

Example 32

N-[4-((1S,2S)-2-{[(2S)-2-methylpyrrolidin-1-yl]methyl}cyclopropyl)phenyl]-5-(trifluoromethyl)thieno[3,2-b]pyridine-6-carboxamide

Example 32A 4-((1S,2S)-2-(((S)-2-methylpyrrolidin-1-yl)methyl)cyclopropyl)aniline A solution of the product from Example 1D (1.72 g, 5.85 mmol), lithium bis(trimethylsilyl)amide (1.51 g, 8.78 mmol), Pd$_2$(dba)$_3$ (268 mg, 0.29 mmol) and tri-t-butylphosphine (1.42 g, 10% in hexane, 0.702 mmol) in anhydrous toluene (10 mL) was heated to 120° C. in a sealed tube for 16 hours. The mixture was cooled to ambient temperature, treated with HCl (1 M) and extracted with ethyl acetate (2×75 mL). The organic layers were combined, washed with H$_2$O and brine, and dried with magnesium sulfate. After filtration, the organic layer was concentrated under reduced pressure and the resulting oil was purified on silica gel with 1% to 3% methanol (containing 10% concentrated NH$_4$OH) in dichloromethane to provide the title compound. $^1$H NMR (300 MHz, CD$_3$OD) δ 0.70-0.76 (m, 1H), 0.82-0.88 (m, 1H), 1.13 (d, J=6 Hz, 3H), 1.03-1.11 (m, 1H), 1.35-1.48 (m, 1H), 1.60-1.66 (m, 1H), 1.69-1.87 (m, 3H), 1.92-2.04 (m, 1H), 2.27 (dd, J=12 Hz, J=9 Hz, 1H), 2.32-2.40 (m, 1H), 3.12 (dd, J=12 Hz, J=3 Hz, 1H), 3.23-3.29 (m, 1H), 6.64 (d, J=9 Hz, 2H), 6.84 (d, J=9 Hz, 2H). MS (DCl—NH$_3$) m/z 231 (M+H)$^+$.

Example 32B

N-[4-((1S,2S)-2-{[(2S)-2-methylpyrrolidin-1-yl]methyl}cyclopropyl)phenyl]-5-(trifluoromethyl)thieno[3,2-b]pyridine-6-carboxamide A solution of the product from Example 32A (50 mg, 0.22 mmol), 5-(trifluoromethyl)thieno[3,2-b]pyridine-6-carboxylic acid (110 mg, 0.44 mmol), and N-(3-dimethylaminopropyl)-N'-ethylcarbodiimide hydrochloride (55 mg, 0.28 mmol) in DCM (10 mL) was treated with triethylamine (0.061 mL, 0.44 mmol), and stirred at ambient temperature for 16 hours. The mixture was concentrated under reduced pressure and the residue was purified on silica gel with 1% to 3% methanol (containing 10% concentrated NH$_4$OH) in dichloromethane to provide the title compound. $^1$H NMR (300 MHz, CD$_3$OD) δ 0.86-1.92 (m, 1H), 0.99-1.05 (m, 1H), 1.17 (d, J=6 Hz, 3H), 1.20-1.29 (m, 1H), 1.42-1.52 (m, 1H), 1.73-1.83 (m, 3H), 1.94-2.08 (m, 2H), 2.32-2.51 (m, 2H), 3.17 (dd, J=12 Hz, J=3 Hz, 1H), 3.26-3.30 (m, 1H), 7.10 (d, J=9 Hz, 1H), 7.55 (d, J=9 Hz, 2H), 7.70 (d, J=6 Hz, 2H), 8.30 (d, J=6 Hz, 1H), 8.74 (s, 1H). MS (DCl—NH$_3$) m/z 460 (M+H)$^+$.

Example 33

N-(4-[(1S,2S)-2-{[(2S)-2-methylpyrrolidin-1-yl]methyl}cyclopropyl]phenyl)isonicotinamide A solution of the product from Example 32A (50 mg, 0.22 mmol) isonicotinoyl chloride hydrochloride (62 mg, 0.31 mmol), and 4-dimethylaminopyridine (5 mg, 0.04 mmol) in DCM (10 mL) was treated with triethylamine (0.12 mL, 0.86 mmol) and stirred at ambient temperature for 16 hours. The mixture was concentrated under reduced pressure and the residue was purified on silica gel with 1% to 3% methanol (containing 10% concentrated NH$_4$OH) in dichloromethane to provide the title compound. $^1$H NMR (300 MHz, CD$_3$OD) δ 1.04-1.10 (m, 1H), 1.16-1.23 (m, 1H), 1.39 (d, J=6 Hz, 3H), 1.37-1.42 (m, 1H), 1.66-1.77 (m, 1H), 2.01-2.08 (m, 3H), 2.25-2.36 (m, 1H), 2.94 (dd, J=6 Hz, J=3 Hz, 1H), 3.15-3.21 (m, 1H), 3.40 (dd, J=6 Hz, J=3 Hz, 1H), 3.61-3.70 (m, 1H), 7.16 (d, J=9 Hz, 1H), 7.63 (d, J=9 Hz, 2H), 7.86 (d, J=6 Hz, 2H), 8.73 (d, J=3 Hz, 1H), 8.03 (m, 1H). MS (DCl—NH$_3$) m/z 336 (M+H)$^+$.

Example 34

2-[4-((1S,2S)-2-{[(2S)-2-Methylpyrrolidin-1-yl]methyl}cyclopropyl)phenyl]pyridazin-3(2H)-one

Example 34A (E)-3-(4-bromophenyl)prop-2-en-1-ol

To a solution of (E)-ethyl 3-(4-bromophenyl)acrylate (25 g, 96 mmol) in DCM (300 ml) under nitrogen and cooled to −78° C. was added dropwise DIBAL-H (240 ml, 1M in DCM, 240 mmol) in about 20 minutes. The mixture was stirred at −78° C. for 2 hours. Then, the dry ice bath was removed. The reaction was diluted with DCM (500 mL), quenched with HCl (1N), and partitioned. The combined organic phases were washed with H$_2$O, dried and concentrated under reduced pressure to provide the title compound. $^1$H NMR (300 MHz, CDCl$_3$): 1.43 (t, J=6 Hz, 1H), 4.32 (t, J=4.5 Hz, 2H), 6.37 (dt, J=16.5 Hz, J=6 Hz, 1H), 6.57 (d, J=15 Hz, 1H), 7.25 (d, J=9 Hz, 2H), 7.45 (d, J=9 Hz, 2H). MS (DCl—NH$_3$) m/z 214 (M+H)$^+$.

Example 34B 2-butyl-1,3,6,2-dioxazaborocane

To a solution of 2,2'-azanediyldiethanol (26.12 g, 246 mmol) in DCM (250 ml) and ether (500 mL) was added n-butylboronic acid (25.4 g, 242 mmol) and molecular sieves (3A, 4-6 mesh, 65 g). It was stirred at ambient temperature for 2 hours. The mixture was filtered, and the filtrate was concentrated under reduced pressure. The resulting white solid was recrystallized with DCM/ether to provide white crystals as the title product. NMR (300 MHz, CDCl$_3$): δ 0.47 (t, J=9 Hz, 2H), 0.88 (t, J=6 Hz, 3H), 1.20-1.37 (m, 4H), 2.82 (br, 2H), 3.24 (br, 2H), 3.95 (br, 4H), 4.27 (br, 1H). MS (DCl—NH$_3$) m/z 172 (M+H)$^+$.

Example 34C (4R,5R)-2-butyl-N4, N4, N5, N5-tetramethyl-1,3,2-dioxaborolane-4,5-dicarboxamide A solution of the product from Example 34B (31.3 g, 183 mmol) and (2R,3R)-2,3-dihydroxy-N1,N1,N4,N4-tetramethylsuccinamide (31 g, 149 mmol) in DCM (600 mL) was treated with brine (120 mL) and stirred at ambient temperature for 30 minutes. The organic layer was separated, and the aqueous layer was extracted with additional DCM. The organic layers were combined and washed with brine (700 mL), dried with MgSO$_4$, and concentrated under reduced pressure to provide the title product. NMR (300 MHz, CDCl$_3$): δ 0.83-0.90 (m, 6H), 1.26-1.42 (m, 5H), 2.98 (s, 6H), 3.20 (s, 6H). MS (DCl—NH$_3$) m/z 205 (M+H)$^+$.

Example 34D (1S,2S)-[2-(4-Bromophenyl)cyclopropyl]methanol

A solution of DME (24.39 mL, 235 mmol) in DCM (700 mL) under nitrogen atmosphere was cooled to –10° C., and diethylzinc (235 mL, 1M in hexane, 235 mmol) was added over 5-10 minutes followed by diiodomethane (37.9 mL, 469 mmol). The product from Example 34C (33.0 g, 122 mmol) in 100 mL DCM was added in 5-10 minutes. The temperature was maintained from –5° to –10° C. throughout the additions. The product from Example 34A, (E)-3-(4-bromophenyl)prop-2-en-1-ol (20 g, 94 mmol) in DCM (150 mL) was added dropwise, and the reaction mixture was stirred at ambient temperature for 16 hours. It was quenched with saturated aqueous NH$_4$Cl (300 mL), HCl (1N, 480 mL) and diluted with ether (900 mL). The organic layer was separated. The aqueous layer was extracted with additional ether. The organic layers were combined and treated with NaOH (2N, 880 mL). To the solution, H$_2$O$_2$ (30%, 136 mL) was added dropwise while the reaction was cooled with an ice bath. The solution was stirred for 5-10 minutes. The organic layer was separated, washed with HCl (1N), saturated aqueous Na$_2$S$_2$O$_3$, saturated aqueous NaHCO$_3$, and brine, dried and concentrated. The residue was chromatographed on silica gel eluting with 5-15% EtOAc/Hexane to provide the title compound. $^1$H NMR (300 MHz, CDCl$_3$): δ 0.92-1.0 (m, 2H), 1.45-1.48 (m, 2H), 1.76-1.85 (m, 1H), 3.61 (d, J=7.5 Hz, 2H), 6.95 (d, J=9 Hz, 2H), 7.37 (d, J=9 Hz, 2H). MS (DCl—NH$_3$) m/z 228 (M+H)$^+$. (ee 94%).

Example 34E (1S,2S)-2-(4-Bromophenyl)cyclopropanecarbaldehyde

To a solution of oxalyl chloride (17.50 mL, 2 M in DCM, 35.0 mmol) in DCM (150 mL) under nitrogen atmosphere and cooled to –78° C. was added dropwise DMSO (4.97 mL, 70.0 mmol), followed with the dropwise addition of a solution of the product from Example 34D, ((1S,2S)-2-(4-bromophenyl)cyclopropyl)methanol (5.3 g, 23.34 mmol) in DCM (100 mL). The mixture was stirred 30 minutes at –78° C. Then the mixture was treated with triethylamine (13.01 mL, 93 mmol), and then the reaction temperature was raised to ambient temperature. The mixture was partitioned between DCM (400 mL) and H$_2$O (400 mL). The organic layer was separated, washed with water, dried and concentrated under reduced pressure to provide the title product. $^1$H NMR (300 MHz, CDCl$_3$): δ 1.48 (m, 1H), 1.65 (dt, J=9 Hz, J=6 Hz, 1H), 2.15 (m, 1H), 2.57 (m, 1H), 6.98 (d, J=9 Hz, 2H), 7.45 (d, J=9 Hz, 2H), 9.46 (d, J=4.5 Hz, 1H). MS (DCl—NH$_3$) m/z 226 (M+H)$^+$.

Example 34F

1-{[(1S,2S)-2-(4-bromophenyl)cyclopropyl]methyl}-(2S)-2-methylpyrrolidine

A solution of the product from Example 34E, (1S,2S)-2-(4-bromophenyl)cyclopropanecarbaldehyde (5.7 g, 25.3 mmol) in DCM (20 ml) and MeOH (300 mL) was treated with (S)-2-methylpyrrolidine tartrate (8.94 g, 38.0 mmol) at ambient temperature, and the mixture was stirred for 5-10 minutes. Then, the mixture was cooled to 0° C., and a solution of NaCNBH$_3$ (2.51 g, 38.0 mmol) in MeOH (50 mL) was added dropwise. After addition, the reaction mixture was raised to room temperature and stirred overnight. The reaction mixture was treated with NaOH (1N) till basic, extracted with DCM thrice (500 mL×3), dried and concentrated under reduced pressure. The crude product was loaded onto a silica gel column and eluted with 1% to 3% methanol (containing 10% concentrated NH$_4$OH) in dichloromethane to provide the title product. $^1$H NMR (300 MHz, CDCl$_3$): δ 0.87-0.92(m, 1H), 0.97-1.02 (m, 1H), 1.16 (d, J=6 Hz, 2H), 1.22 (m, 1H), 1.39-1.49(m, 1H), 1.73-1.81(m, 3H), 2.0 (m, 2H), 2.36 (q, J=6 Hz, 1H), 2.45 (m, 1H), 3.13 (dd, J=12 Hz, J=6 Hz, 1H), 3.25 (m, 1H), 7.00 (d, J=6 Hz, 2H), 7.37 (d, J=6 Hz, 2H). MS (DCl—NH$_3$) m/z 294 (M+H)$^+$.

Example 34G

2-[4-((1S,2S)-2-{[(2S)-2-Methylpyrrolidin-1-yl]methyl}cyclopropyl)phenyl]pyridazin-3(2H-one A solution of the product from Example 34F, 1-{[(1S,2S)-2-(4-bromophenyl)cyclopropyl]methyl}-(2S)-2-methylpyrrolidine (100 mg, 0.340 mmol), pyridazin-3(2H)-one (52.3 mg, 0.544 mmol), N1,N2-dimethylethane-1,2-diamine (0.088 mL, 0.816 mmol) and copper(I) iodide (78 mg, 0.408 mmol) in pyridine (2 mL) under a nitrogen atmosphere in a sealed vial was heated in an oil bath to 135° C. for 16 hours. The reaction mixture was cooled and diluted with DCM (10 mL), filtered through diatomaceous earth and washed with DCM. The filtrate was washed sequentially with H$_2$O, 28-30% NH$_4$OH (10 mL×2), and H$_2$O, dried with MgSO$_4$ and concentrated under reduced pressure. The residue was chromatographed on silica gel eluting with concentrated NH$_4$OH/MeOH/DCM (0.4/4/96) to provide the title compound. $^1$H NMR (300 MHz, CD₃OD) δ 0.90-0.97 (m, 1H), 1.03-1.09 (m, 1H), 1.15 (d, J=6 Hz, 3H), 1.23-1.33 (m, 1H), 1.39-1.49 (m, 1H), 1.70-1.80 (m, 2H), 1.82-2.05 (m, 3H), 2.26-2.42 (m, 2H), 3.16 (dd, J=12 Hz, J=6 Hz, 1H), 3.21-3.28 (m, 1H), 7.07 (d, J=6 Hz, 2H), 7.21 (dd, J=6 Hz, J=1.5 Hz, 2H), 7.43 (d, J=6 Hz, 2H), 7.47 (dd, J=9 Hz, J=3 Hz, 1H), 8.02 (dd, J=6 Hz, J=1.5 Hz, 1H). MS (DCl—NH₃) m/z 310 (M+H)⁺.

Example 34H

2-[4-((1S,2S)-2-{[(2S)-2-Methylpyrrolidin-1-yl]methyl}cyclopropyl)phenyl]pyridazin-3(2H)-one (2R,3R)-2,3-dihydroxysuccinate A solution of the product from Example 34G (3.25 g, 10.5 mmol) in methanol (20 mL) was treated with L-tartaric acid (1.577 g, 10.5 mmol) and stirred at ambient temperature for 1 hour. The mixture was concentrated under reduced pressure, and the resulting solid was recrystallized from isopropyl alcohol/acetone to provide the titled compound as the L-tartrate. ¹H NMR (300 MHz, CD₃OD) δ 1.12-1.19 (m, 1H), 1.23-1.30 (m, 1H), 1.43 (d, J=6 Hz, 3H), 1.47-1.56 (m, 1H), 1.72-1.81 (m, 1H), 2.02-2.19 (m, 3H), 2.28-2.39 (m, 1H), 3.04-3.11 (m, 1H), 3.43-3.55 (m, 2H), 3.64-3.75 (m, 2H), 4.38 (s, 2H), 7.08 (dd, J=6 Hz, J=2 Hz, 1H), 7.28 (d, J=6 Hz, 2H), 7.44-7.50 (m, 3H), 8.03 (m, 1H). MS (DCl—NH₃) m/z 310 (M+H)⁺. Anal. Calcd. For C23H29N3O7: C, 60.12; 6.36; N, 9.14. Found: 60.07; 5.76; N, 8.82.

Example 35

2-[4-((1S,2S)-2-{[(2R)-2-methylpyrrolidin-1-yl]methyl}cyclopropyl)phenyl]pyridazin-3(2H)-one

Example 35A (R)-1-(((1S,2S)-2-(4-bromophenyl)cyclopropyl)methyl)-2-methylpyrrolidine The title compound was prepared using the procedure described in Example 34F substituting (R)-2-methylpyrrolidine tartrate for (S)-2-methylpyrrolidine tartrate. ¹H NMR (300 MHz, CDCl₃): δ 0.88-0.94(m, 1H), 0.95-1.02 (m, 1H), 1.12 (d, J=6 Hz, 2H), 1.19-1.29 (m, 1H), 1.37-1.49(m, 1H), 1.71-1.81(m, 3H), 1.93-2.05 (m, 1H), 2.12 (dd, J=12 Hz, J=6 Hz, 1H), 2.29 (q, J=6 Hz, 1H), 2.36-2.45 (m, 1H), 2.93 (dd, J=12 Hz, J=6 Hz, 1H), 3.25 (m, 1H), 7.00 (d, J=6 Hz, 2H), 7.37 (d, J=6 Hz, 2H). MS (DCl—NH₃) m/z 294 (M+H)⁺.

Example 35B

2-[4-((1S,2S)-2-{[(2R)-2-methylpyrrolidin-1-yl]methyl}cyclopropyl)phenyl]pyridazin-3(2H)-one The title compound was prepared using the procedure described in Example 34G substituting the product from Example 35A for the product from Example 34F, 1-{[(1S,2S)-2-(4-bromophenyl)cyclopropyl]methyl}-(2S)-2-methylpyrrolidine. ¹H NMR (300 MHz, CD₃OD) δ 0.94-0.98 (m, 1H), 1.05-1.09 (m, 1H), 1.13 (d, J=3 Hz, 3H), 1.30-1.36 (m, 1H), 1.4-1.48 (m, 1H), 1.72-1.81 (m, 2H), 1.84-1.88 (m, 1H), 2.16 (dd, J=6 Hz, J=3 Hz, 1H), 2.31 (q, J=6 Hz, 1H), 2.41-2.45 (m, 1H), 2.94-2.98 (q, J=3 Hz, 1H), 3.25-3.29 (m, 1H), 7.07 (d, J=6 Hz, 2H), 7.21 (d, J=6 Hz, 2H), 7.41 (d, J=6 Hz, 2H), 7.46 (dd, J=6 Hz, J=3 Hz, 1H), 8.02-8.03 (m, 1H). MS (DCl—NH₃) m/z 310 (M+H)⁺.

Example 36

1-[4-((1S,2S)-2-{[(2R)-2-methylpyrrolidin-1-yl]methyl}cyclopropyl)phenyl]piperidin-2-one The title compound was prepared using the procedure described in Example 34G substituting piperidin-2-one for pyridazin-3(2H)-one and substituting the product from Example 35A for the product from Example 34F. ¹H NMR (300 MHz, CD₃OD) δ 1.08-1.21 (m, 2H), 1.39 (d, J=6 Hz, 3H), 1.43-1.48 (m, 1H), 1.68-1.78 (m, 1H), 1.92-1.96 (m, 3H), 2.01-2.08 (m, 3H), 2.23-2.35 (m, 1H), 2.50 (t, J=6 Hz, 2H), 3.03 (dd, J=12 Hz, J=6 Hz, 1H), 3.13-3.22 (m, 1H), 3.32-3.36 (m, 1H), 3.39-3.47 (m, 1H), 3.58-3.67 (m, 3H), 7.17 (d, J=3 Hz, 4H). MS (DCl—NH₃) m/z 313 (M+H)⁺.

Example 37

1-[4-((1S,2S)-2-{[(2R)-2-methylpyrrolidin-1-yl]methyl}cyclopropyl)phenyl]azepan-2-one The title compound was prepared using the procedure described in Example 35B substituting azepan-2-one for pyridazin-3(2H)-one and substituting the product from Example 35A for the product from Example 34F. ¹H NMR (300 MHz, CD₃OD) δ 1.02-1.08 (m, 1H), 1.13-1.19 (m, 1H), 1.36 (d, J=6 Hz, 3H), 1.35-1.38 (m, 1H), 1.64-1.71 (m, 1H), 1.84 (broad, 6H), 1.97-2.05 (m, 3H), 2.21-2.32 (m, 1H), 2.67-2.71 (m, 2H), 2.78-2.85 (m, 1H), 3.05-3.15 (m, 1H), 3.23-3.28 (m, 1H), 3.35-3.41 (m, 1H), 3.54-3.63 (m, 1H), 3.75-3.78 (m, 1H), 7.13 (d, J=3 Hz, 4H). MS (DCl—NH₃) m/z 327 (M+H)⁺.

Example 38

1-[4-((1S,2S)-2-{[(2R)-2-methylpyrrolidin-1-yl]methyl}cyclopropyl)phenyl]pyrrolidin-2-one The title compound was prepared using the procedure described in Example 35B substituting pyrrolidin-2-one for pyridazin-3(2H)-one and substituting the product from Example 35A for the product from Example 34F. ¹H NMR (300 MHz, CD₃OD) δ 0.89-0.96 (m, 1H), 1.01-1.08 (m, 1H), 1.22 (d, J=6 Hz, 3H), 1.25-1.30 (m, 1H), 1.48-1.55 (m, 1H), 1.8-1.89 (m, 4H), 2.03-2.27 (m, 4H), 2.57 (t, J=6 Hz, 2H), 2.65-2.74 (m, 1H), 3.22 (q, J=6 Hz, 1H), 3.33-3.40 (m, 1H), 3.89 (t, J=6 Hz, 2H), 7.10 (d, J=9 Hz, 2H), 7.46 (d, J=9 Hz, 2H). MS (DCl—NH₃) m/z 299 (M+H)⁺.

Example 39

1-[4-((1S,2S)-2-{[(2R)-2-methylpyrrolidin-1-yl]methyl}cyclopropyl)phenyl]azetidin-2-one The title compound was prepared using the procedure described in Example 35B substituting azetidin-2-one for pyridazin-3(2H)-one and substituting the product from Example 35A for the product from Example 34F. ¹H NMR (300 MHz, CD₃OD) δ 0.98-1.04 (m, 1H), 1.08-1.15 (m, 1H), 1.34 (d, J=6 Hz, 3H), 1.35 (m, 1H), 1.59-1.72 (m, 1H), 1.94-2.04 (m, 3H), 2.18-2.29 (m, 1H), 2.75 (q, J=6 Hz, 1H), 2.98-3.07 (m, 1H), 3.08 (t, J=6 Hz, 2H), 3.16-3.26 (m, 1H), 3.32-3.36 (m, 1H), 3.52-3.62 (m, 1H), 3.65 (t, J=6 Hz, 2H), 7.11 (d, J=9 Hz, 2H), 7.30 (d, J=9 Hz, 2H). MS (DCl—NH₃) m/z 299 (M+H)⁺.

Example 40

1-[4-((1S,2S)-2-{[(2S)-2-methylpyrrolidin-1-yl]methyl}cyclopropyl)phenyl]azetidin-2-one The title compound was prepared using the procedure described in Example 34G substituting azetidin-2-one for pyridazin-3(2H)-one. $^1$H NMR (300 MHz, CD$_3$OD) δ 0.97-1.03 (m, 1H), 1.08-1.14 (m, 1H), 1.33 (d, J=6 Hz, 3H), 1.35 (m, 1H), 1.60-1.68 (m, 1H), 1.94-2.04 (m, 3H), 2.17-2.29 (m, 1H), 2.71 (q, J=6 Hz, 1H), 2.96-3.03 (m, 1H), 3.08 (t, J=6 Hz, 2H), 3.13-3.22 (m, 1H), 3.51-3.59 (m, 1H), 3.66 (t, J=6 Hz, 2H), 7.11 (d, J=9 Hz, 2H), 7.30 (d, J=9 Hz, 2H). MS (DCl—NH$_3$) m/z 285 (M+H)$^+$.

Example 41

1-[4-((1S,2S)-2-{[(2S)-2-methylpyrrolidin-1-yl]methyl}cyclopropyl)phenyl]azepan-2-one The title compound was prepared using the procedure described in Example 34G substituting azepan-2-one for pyridazin-3(2H)-one. $^1$H NMR (300 MHz, CD$_3$OD) δ 0.98-1.05 (m, 1H), 1.09-1.16 (m, 1H), 1.32 (d, J=6 Hz, 3H), 1.36-1.39 (m, 1H), 1.59-1.69 (m, 1H), 1.83 (broad, 6H), 1.94-2.0 (m, 3H), 2.16-2.27 (m, 1H), 2.61-2.71 (m, 2H), 2.90-2.98 (m, 1H), 3.07-3.14 (m, 1H), 3.32-3.37 (m, 1H), 3.48-3.58 (m, 1H), 3.75-3.78 (m, 1H), 7.13 (d, J=3 Hz, 4H). MS (DCl—NH$_3$) m/z 327 (M+H)$^+$.

Example 42

1-[4-((1S,2S)-2-{[(2S)-2-methylpyrrolidin-1-yl]methyl}cyclopropyl)phenyl]piperidin-2-one The title compound was prepared using the procedure described in Example 34G substituting piperidin-2-one for pyridazin-3(2H)-one. $^1$H NMR (300 MHz, CD$_3$OD) δ 0.97-1.03 (m, 1H), 1.08-1.15 (m, 1H), 1.30 (d, J=6 Hz, 3H), 1.31-1.38 (m, 1H), 1.56-1.63 (m, 1H), 1.92-1.99 (m, 3H), 2.14-2.24 (m, 3H), 2.49 (t, J=6 Hz, 2H), 2.52-2.59 (m, 1H), 2.81-2.90 (m, 1H), 2.96-3.04 (m, 1H), 3.44-3.54 (m, 1H), 3.61-3.65 (m, 2H), 7.17 (d, J=3 Hz, 4H). MS (DCl—NH$_3$) m/z 313 (M+H)$^+$.

Example 43

1-[4-((1S,2S)-2-{[(2S)-2-methylpyrrolidin-1-yl]methyl}cyclopropyl)phenyl]pyrrolidin-2-one The title compound was prepared using the procedure described in Example 34G substituting pyrrolidin-2-one for pyridazin-3(2H)-one. $^1$H NMR (300 MHz, CD$_3$OD) δ 0.99-1.05 (m, 1H), 1.10-1.16 (m, 1H), 1.34 (d, J=6 Hz, 3H), 1.35-1.40 (m, 1H), 1.59-1.71 (m, 1H), 1.95-2.04 (m, 3H), 2.12-2.27 (m, 3H), 2.58 (t, J=6 Hz, 2H), 2.67-2.76 (m, 1H), 3.02 (q, J=6 Hz, 1H), 3.15-3.22 (m, 1H), 3.31-3.37 (m, 1H), 3.51-3.59 (m, 1H), 3.89 (t, J=6 Hz, 2H), 7.13 (d, J=9 Hz, 2H), 7.49 (d, J=9 Hz, 2H). MS (DCl—NH$_3$) m/z 299 (M+H)$^+$.

Example 44

N-[4-((1S,2S)-2-{[(2S)-2-methylpyrrolidin-1-yl]methyl}cyclopropyl)phenyl]acetamide The title compound was prepared using the procedure described in Example 34G substituting acetamide for pyridazin-3(2H)-one. $^1$H NMR (300 MHz, CD$_3$OD) δ 0.98-1.04 (m, 1H), 1.09-1.16 (m, 1H), 1.36 (d, J=6 Hz, 3H), 1.29-1.40 (m, 1H), 1.61-1.74 (m, 1H), 1.94-2.06 (m, 3H), 2.10 (s, 3H), 2.20-2.32 (m, 1H), 2.77-2.84 (m, 1H), 3.04-3.14 (m, 1H), 3.21-3.27 (m, 1H), 3.33-3.39 (m, 1H), 3.55-3.63 (m, 1H), 7.06 (d, J=9 Hz, 2H), 7.44 (d, J=9 Hz, 2H). MS (DCl—NH$_3$) m/z 273 (M+H)$^+$.

Example 45

(S)-3-hydroxy-1-(4-((1S,2S)-2-(((S)-2-methylpyrrolidin-1-yl)methyl)cyclopropyl)phenyl)pyrrolidin-2-one The title compound was prepared using the procedure described in Example 34G substituting (S)-3-hydroxypyrrolidin-2-one (CAS# 34368-52-0) for pyridazin-3(2H)-one. 1H NMR (300 MHz, CHLOROFORM-D) d ppm 0.80-0.88 (m, 1 H) 0.89-0.96 (m, 1 H) 1.11 (t, 3 H) 1.19-1.31 (m, 1 H) 1.35-1.50 (m, 1 H) 1.61-1.73 (m, 3 H) 1.83-1.95 (m, 2 H) 2.03-2.18 (m, 2 H) 2.19-2.31 (m, 1 H) 2.53-2.66 (m, 1 H) 3.00-3.14 (m, 2 H) 3.25 (dd, 1 H) 3.76 (dd, 2 H) 4.45 (dd, 1 H) 7.06 (d, 2 H) 7.51 (d, 2 H). MS (DCl—NH$_3$) m/z 315 (M+H)$^+$.

Example 46

2-{4-[(1S,2S)-2-((S)-2-Methyl-pyrrolidin-1-ylmethyl)-cyclopropyl]-phenyl}-2H-pyridazin-3-one (2S,3S)-2,3-dihydroxy-succinic acid A solution of the product from the Example 34G, 2-(4-((1S,2S)-2-(((S)-2-methylpyrrolidin-1-yl)methyl)cyclopropyl)phenyl)pyridazin-3(2H)-one, (615 mg, 0.5 mmol) in methanol (10 mL) was treated with D-tartaric acid (350 mg) and stirred at ambient temperature for 30 minutes. The mixture was concentrated under the reduced pressure and the residue was crystallized in 2-propanol/acetone to provide the title product as white crystalline solid. M.P. 145-147.1° C. Anal. Calc. for $C_{23}H_{26}N_2 \cdot C_4H_6O_6$: C, 60.12; H, 6.36; N, 9.14. Found: C, 59.94; H, 6.57; N, 9.17.

Determination of Biological A

To determine the effectiveness of representative compounds of this invention as histamine-3 receptor ligands (H$_3$ receptor ligands), the following tests were conducted according to methods previously described (European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid N$_2$ and stored at –70° C. until used in assays. Rat cortical membranes (12 mg wet weight/tube) were incubated with (3H)—N-α-methylhistamine (~0.6 nM) with or without H$_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 µM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and $K_i$ values were determined using the Cheng-Prusoff equation.

As an alternative to the use of cortical membranes from rats as a source of histamine $H_3$ receptors, membranes prepared from cells expressing $H_3$ receptors are also suitable. For this, the rat histamine $H_3$ receptor, cloned and expressed in cells was used, and subsequently competition binding assays were carried out according to methods previously described (see Esbenshade, et al. Journal of Pharmacology and Experimental Therapeutics, vol. 313:165-175, 2005; Esbenshade et al., Biochemical Pharmacology vol. 68 (2004) 933-945; Krueger, et al. Journal of Pharmacology and Experimental Therapeutics, vol. 314:271-281, 2005.) Membranes were prepared from C6 or HEK293 cells, expressing the rat histamine $H_3$ receptor, by homogenization on ice in TE buffer (50 mM Tris-HCl buffer, pH 7.4, containing 5 mM EDTA), 1 mM benzamidine, 2 pg/ml aprotinin, 1 µg/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with [$^3$H]—N-α-methylhistamine (0.5-1.0 nM) in the presence or absence of increasing concentrations of ligands for $H_3$ receptor competition binding. The binding incubations were conducted in a final volume of 0.5 ml TE buffer at 25° C. and were terminated after 30 minutes. Thioperamide (30 µM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 ml of ice-cold TE buffer. Bound radiolabel was determined by liquid scintillation counting. For all of the radioligand competition binding assays, $IC_{50}$ values and Hill slopes were determined by Hill transformation of the data and $pK_i$ values were determined by the Cheng-Prusoff equation.

Generally, representative compounds of the invention demonstrated binding affinities in the above assays from about 0.05 nM to about 1000 nM. Preferred compounds of the invention bound to histamine-3 receptors with binding affinities from about 0.05 nM to about 250 nM. More preferred compounds of the invention bound to histamine-3 receptors with binding affinities from about 0.05 nM to about 10 nM.

In addition to the utility of in vitro methods for characterizing the $H_3$ binding affinity of compounds, there are animal models of human disease available which demonstrate the utility of compounds of the invention for treating human disease. One animal model of the human disease ADHD (attention deficit hyperactivity disorder) and related human disorders of attention is an inhibitory avoidance test in SHR rat pups (a Spontaneously Hypertensive strain of rat pups). This model has also been alternatively termed a PAR (passive avoidance response) model. The methodology and utility of this test has been described in the literature, for example in Komater, V. A., et al. Psychopharmacology (Berlin, Germany) (2003), 167(4), 363-372; in "Two novel and selective nonimidazole $H_3$ receptor antagonists A-304121 and A-317920: II. In vivo behavioral and neurophysiological characterization." Fox, G. B., et al. Journal of Pharmacology and Experimental Therapeutics (2003), 305(3), 897-908; in Cowart, et al. *J. Med. Chem.* 2005, 48, 38-55; in Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; in "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161. Representative compounds are active in this model, with preferred compounds of the invention active in the model at doses of ranging about 0.001-3 mg/kg of body weight.

Compounds of the invention are histamine-3 receptor ligands that modulate the function of the histamine-3 receptor. The compounds may be inverse agonists that inhibit the basal activity of the receptor or they may be antagonists that block the action of receptor-activating agonists.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound having the structure of 2-[4-((1S,2S)-2-{[(2S)-2-methylpyrrolidin-1-yl]methyl}cyclopropyl)phenyl]pyridazin-3(2H)-one L-bitartrate monohydrate.

2. A crystalline salt of 2-[4-((1S,2S)-2-{[(2S)-2-methylpyrrolidin-1-yl]methyl}cyclopropyl)phenyl]-pyridazin-3(2H)-one, identified by powder X-ray diffraction (PXRD) wherein the salt is:
   crystalline 2-{4-[(1S,2S)-2-((S)-2-methyl-pyrrolidin-1-ylmethyl)-cyclopropyl]-phenyl}-2H-pyridazin-3-one L-bitartrate monohydrate demonstrating at least one characteristic peak in the PXRD at values of two-theta of 7.157±0.20, 10.064±0.20, 14.356±0.20, 16.727±0.20, 19.198±0.20, 20.119±0.20, 21.222±0.20, 22.146±0.20, 24.048±0.20, and 24.574±0.20.

3. A compound having the structure of 2-[4-((1S,2S)-2-{[(2S)-2-methylpyrrolidin-1-yl]methyl}cyclopropyl)phenyl]pyridazin-3(2H)-one L-bitartrate anhydrate.

4. A compound having the structure of 2-[4-((1S,2S)-2-{[(2S)-2-methylpyrrolidin-1-yl]methyl}cyclopropyl)phenyl]pyridazin-3(2H)-one D-bitartrate dihydrate.

5. A compound having the structure of 2-[4-((1S,2S)-2-{[(2S)-2-methylpyrrolidin-1-yl]methyl}cyclopropyl)phenyl]pyridazin-3(2H)-one D-bitartrate anhydrate.

6. A crystalline salt of 2-[4-((1S,2S)-2-{[(2S)-2-methylpyrrolidin-1-yl]methyl}cyclopropyl)phenyl]pyridazin-3(2H)-one, identified by powder X-ray diffraction (PXRD) wherein the salt is:
   crystalline 2-{4-[(1S,2S)-2-((S)-2-methyl-pyrrolidin-1-ylmethyl)-cyclopropyl]-phenyl}-2H-pyridazin-3-one L-bitartrate anhydrate demonstrating at least one characteristic peak in the PXRD at values of two-theta of 4.589±0.20, 9.206±0.20, 13.85±0.20, 14.335±0.20, 15.824±0.20, 16.272±0.20, 16.825±0.20, 18.083±0.20, 18.514±0.20, 19.588±0.20, and 20.551±0.20.

7. A crystalline salt of 2-[4-((1S,2S)-2-{[(2S)-2-methylpyrrolidin-1-yl]methyl}cyclopropyl)phenyl]pyridazin-3(2H)-one, identified by powder X-ray diffraction (PXRD) wherein the salt is:

crystalline 2-{4-[(1S,2S)-2-((S)-2-methyl-pyrrolidin-1-ylmethyl)-cyclopropyl]-phenyl}-2H-pyridazin-3-one D-bitartrate dihydrate demonstrating at least one characteristic peak in the PXRD at values of two-theta of 4.387±0.20, 8.788±0.20, 10.326±0.20, 12.056±0.20, 13.192±0.20, 14.089±0.20, 16.194±0.20, 19.502±0.20, 19.877±0.20, 20.271±0.20, 20.736±0.20, 21.313±0.20, 23.103±0.20, and 23.937±0.20.

8. A crystalline salt of 2-[4-((1S,2S)-2-{[(2S)-2-methylpyrrolidin-1-yl]methyl}cyclopropyl)phenyl]pyridazin-3(2H)-one, identified by powder X-ray diffraction (PXRD) wherein the salt is:

crystalline 2-{4-[(1S,2S)-2-((S)-2-methyl-pyrrolidin-1-ylmethyl)-cyclopropyl]-phenyl}-2H-pyridazin-3-one D-bitartrate anhydrate demonstrating at least one characteristic peak in the PXRD at values of two-theta of 5.004±0.20, 10.590±0.20, 13.548±0.20, 14.219±0.20, 15.279±0.20, 15.723±0.20, 16.990±0.20, 18.723±0.20, 19.052 ±0.20, 20.827±0.20, 21.293±0.20, and 22.826±0.20.

9. A pharmaceutical composition comprising a therapeutically effective amount of a compound of claim 1, 2, 3, 4, 5, 6, 7, or 8 in combination with a pharmaceutically acceptable carrier.

* * * * *